"(12) United States Patent
Lafarge et al.

US010538780B1

(10) Patent No.: US 10,538,780 B1
(45) Date of Patent: Jan. 21, 2020

(54) METHOD OF PLANT IMPROVEMENT USING ASPARTATE KINASE-HOMOSERINE DEHYDROGENASE

(71) Applicant: BIOGEMMA, Paris (FR)

(72) Inventors: Stéphane Lafarge, Chappes (FR); Jacques Rouster, Chappes (FR); Francois Torney, Chappes (FR); Jerome Martin, Chappes (FR)

(73) Assignee: BIOGEMMA, Paris (FR)

( * ) Notice: Subject to any disclaimer, the term of this patent is extended or adjusted under 35 U.S.C. 154(b) by 5 days.

(21) Appl. No.: 15/561,749

(22) PCT Filed: Mar. 30, 2016

(86) PCT No.: PCT/EP2016/056948
§ 371 (c)(1),
(2) Date: Sep. 26, 2017

(87) PCT Pub. No.: WO2016/156421
PCT Pub. Date: Oct. 6, 2016

(30) Foreign Application Priority Data

Mar. 31, 2015 (EP) .................................... 15305470

(51) Int. Cl.
| | | |
|---|---|---|
| *C12N 15/82* | (2006.01) |
| *A01H 5/00* | (2018.01) |
| *C12N 9/04* | (2006.01) |
| *C07K 14/415* | (2006.01) |
| *A01H 4/00* | (2006.01) |
| *C12N 9/12* | (2006.01) |

(52) U.S. Cl.
CPC ........... *C12N 15/8271* (2013.01); *A01H 4/00* (2013.01); *A01H 5/00* (2013.01); *C07K 14/415* (2013.01); *C12N 9/0006* (2013.01); *C12N 9/1217* (2013.01); *C12N 15/8225* (2013.01); *C12N 15/8226* (2013.01); *C12N 15/8227* (2013.01); *C12Y 101/01003* (2013.01)

(58) Field of Classification Search
CPC ........ C12N 15/8261; C12Y 207/02004; C12Y 101/01003
See application file for complete search history.

(56) References Cited

U.S. PATENT DOCUMENTS

| | | |
|---|---|---|
| 2006/0123505 A1 | 6/2006 | Kikuchi et al. |
| 2007/0028327 A1 | 2/2007 | Perez et al. |
| 2009/0307795 A1 | 12/2009 | Perez et al. |
| 2010/0306876 A1 | 12/2010 | Perez et al. |
| 2011/0226267 A1 | 9/2011 | Jones et al. |
| 2012/0011621 A1 | 1/2012 | Perez et al. |
| 2012/0199144 A2* | 8/2012 | Jones ............... C12N 9/0004 131/275 |
| 2015/0007360 A1 | 1/2015 | Biogemma |

FOREIGN PATENT DOCUMENTS

| | | | |
|---|---|---|---|
| WO | WO-00/63398 A1 | 10/2000 | |
| WO | WO-02/088301 A2 | 11/2002 | |
| WO | WO-2010/002876 A2 | 1/2010 | |
| WO | WO-2014/102773 A1 | 7/2014 | |
| WO | WO-2014102773 A1 * | 7/2014 | ........... C07K 14/415 |
| WO | WO-2014/164014 A1 | 10/2014 | |

OTHER PUBLICATIONS

Millner, J. P., R. Vill Aver, and A. K. Hardacre. "The yield and nutritive value of maize hybrids grown for silage." New Zealand Journal of Agricultural Research 48.1 (2005): 101-108. (Year: 2005).*
Muehlbauer, Gary J., et al. "Molecular genetics of the maize (*Zea mays* L.) aspartate kinase-homoserine dehydrogenase gene family." Plant physiology 106.4 (1994): 1303-1312. (Year: 1994).*
Mazur, Barbara, Enno Krebbers, and Scott Tingey. "Gene discovery and product development for grain quality traits." Science 285.5426 (1999): 372-375. (Year: 1999).*
Falco, S. C., et al. "Transgenic canola and soybean seeds with increased lysine." Nature Biotechnology 13.6 (1995): 577. (Year: 1995).*
Brinch-Pedersen, Henrik, et al. "Engineering of the aspartate family biosynthetic pathway in barley (*Hordeum vulgare* L.) by transformation with heterologous genes encoding feed-back-insensitive aspartate kinase and dihydrodipicolinate synthase." Plant molecular biology 32.4 (1996): 611-620 (Year: 1996).*
Brinch-Pedersen, Henrik et al., "Engineering of the aspartate family biosynthetic pathway in barley (*Hordeum vulgare* L.) by transformation with heterologous genes encoding feed-back-insensitive aspartate kinase and dihydrodipicolinate synthase," Plant Molecular Biology, vol. 32, 1996, pp. 611-620.
Paris, Stephane et al., "Overproduction, Purification, and Characterization of Recombinant Bifunctional Threonine-Sensitive Aspartate Kinase-Homoserine Dehydrogenase from *Arabidopsis thaliana*," Protein Expression and Purification, vol. 24, 2002, pp. 105-110.
International Search Report dated Jun. 2, 2016 for corresponding Application No. PCT/EP2016/056948.
Altschul, Stephen F. et al., "Gapped BLAST and PSI-BLAST: a new generation of protein database search programs," Nucleic Acids Research, vol. 25, No. 17, 1997, pp. 3389-3402.
Altschul, Stephen F. et al., "Protein database searches using compositionally adjusted substitution matrices," The FEBS Journal, vol. 272, 2005, pp. 5101-5109.
An, G. et al., "Transformation of Tobacco, Tomato, Potato, and *Arabidopsis thaliana* Using a Binary Ti Vector System," Plant Physiol., vol. 81, 1986, pp. 301-305.
An, G., "Development of Plant Promoter Expression Vectors and Their Use for Analysis of Differential Activity of Nopaline Synthase Promoter in Transformed Tobacco Cells," Plant Physiol., vol. 81, 1986, pp. 86-91.
Anderson, O. D. et al., "The characterization and comparative analysis of high-molecular-weight glutenin genes from genomes A and B of a hexaploid bread wheat," Theor. Appl. Genet., vol. 77, 1989, pp. 689-700.

(Continued)

*Primary Examiner* — Weihua Fan
(74) *Attorney, Agent, or Firm* — Polsinelli PC

(57) ABSTRACT

The invention relates to the field of plant improvement, in particular of the improvement of yield for plants, by transforming plants with a transgene containing a promoter driving expression of a AK-HSDH protein.

13 Claims, 2 Drawing Sheets

Specification includes a Sequence Listing.

(56) References Cited

OTHER PUBLICATIONS

Bonner, P. et al, "Enzymes of Lysine Synthesis," Methods in Plant Biochemistry, vol. 3, United Kingdom, 1990, pp. 297-313.
Brennecke, K. et al., "Aspartate Kinase in the Maize Mutants *ASK1-LT19* and *Opaque-2*," Phytochemistry, vol. 41, No. 3, 1996, Great Britain, pp. 707-712.
Bryan, P.A. et al., "Isolation and Characterization of a Lysine-Sensitive Aspartokinase from a Multicellular Plant," Biochemical and Biophysical Research Communications, vol. 41, No. 5, 1970, New York, pp. 1211-1217.
Cassan, M. et al., "Nucleotide Sequence of lysC Gene Encoding the Lysine-sensitive Aspartokinase III of *Escherichia coli* K12," The Journal of Biological Chemistry, vol. 261, No. 3, 1986, pp. 1052-1057.
Christensen, A. et al., "Ubiquitin promoter-based vectors for high-level expression of selectable and/or screenable marker genes in monocotyledonous plants," Transgenic Research, vol. 5, 1996, pp. 213-218.
Christian, M. et al., "Targeting DNA Double-Strand Breaks with TAL Effector Nucleases," Genetics, vol. 186, Oct. 2010, pp. 757-761.
Depicker, A., et al., "Nopaline Synthase: Transcript Mapping and DNA Sequence," Journal of Molecular and Applied Genetics, New York, 1982, pp. 561-573.
Depigny-This, D. et al., "The cruciferin gene family in radish," Plant Molecular Biology, vol. 20, Belgium, 1992, pp. 467-479.
Ferreira, R. et al., "Isolation of enzymes involved in threonine biosynthesis from sorghum seeds," Braz. J. Plant Physiol., vol. 16, No. 2, 2004, pp. 95-104.
Ferreira, R. et al., "Determination of Aspartate Kinase Activity in Maize Tissues," Sci. Agric. (Piracicaba, Braz.), vol. 62, No. 2, 2005, pp. 184-189.
Firek, S. et al., "A wound-induced promoter driving *npt-ll* expression limited to dedifferentiated cells at wound sites is sufficient to allow selection of transgenic shoots," Plant Molecular Biology, vol. 22, Belgium, 1993, pp. 129-142.
Flintham, J.E. et al., "Optimizing wheat grain yield: effects of Rht (gibberellin-insensitive) dwarfing genes," The Journal of Agriculture Science, vol. 128, Feb. 1997, pp. 11-25.
Ghislain, M. et al., "Molecular analysis of the aspartate kinase-homoserine dehydrogenase gene from *Arabidopsis thaliana*," Plant Molecular Biology, vol. 24, Belgium, 1994, pp. 835-851.
Ishida, Y. et al., "High efficiency transformation of maize (*Zea mays* L.) mediated by *Agrobacterium tumefaciens*," Nature Biotechnology, vol. 14, Jun. 1996, pp. 745-750.
Jouanin, L. et al., "Structure of T-DNA in plants regenerated from roots transformed by *Agrobacterium rhizogenes* strain A4," Mol. Gen. Genet., vol. 206, 1987, pp. 387-392.
Jouanin, L. et al., "Transfer of a 4.3-kb fragment of the TL-DNA of *Agrobacterium rhizogenes* strain A4 confers the pRi transformed phenotype to regenerated tobacco plants," Plant Science, vol. 53, 1987, pp. 53-63.
Katinka, M. et al., "Nucleotide sequence of the *thrA* gene of *Escherichia coli*," Proc. Natl. Acad. Sci., vol. 77, No. 10, 1980, pp. 5730-5733.

Kay, R. et al., "Duplication of CaMV 35S Promoter Sequences Creates a Strong Enhancer for Plant Genes," Science, vol. 236, 1987, pp. 1299-1302.
Komari, T. et al, "Vectors carrying two separate T-DNAs for co-transformation of higher plants mediated by *Agrobacterium tumefaciens* and segregation of transformants free from selection markers," The Plant Journal, vol. 10, No. 1, 1996, pp. 165-174.
McElroy, D. et al., "Isolation of an Efficient Actin Promoter for Use in Rice Transformation," American Society of Plant Physiologists, The Plant Cell, vol. 2, 1990, pp. 163-171.
Muehlbauer, G. et al., "Molecular Genetics of the Maize (*Zea mays* L.) Aspartate Kinase-Homoserine Dehydrogenase Gene Family," Plant Physiol., vol. 106, 1994, pp. 1303-1312.
Paris, S. et al., "Mechanism of Control of *Arabidopsis thaliana* Aspartate Kinase-Homoserine Dehydrogenase by Threonine," The Journal of Biological Chemistry, vol. 278, No. 7, 2003, pp. 5361-5366.
Peng, J. et al., "<Green revolution> genes encode mutant gibberellin response modulators," Nature, vol. 400, 1999, pp. 256-261.
Rafalski, J. et al., "Structure of the Yeast *HOM3* Gene Which Encodes Aspartokinase," The Journal of Biological Chemistry, vol. 263, No. 5, 1988, pp. 2146-2151.
Robert, L. et al., "Tissue-Specific Expression of a Wheat High Molecular Weight Glutenin Gene in Transgenic Tobacco," American Society of Plant Physiologists, The Plant Cell, vol. 1, 1989, pp. 569-578.
Rodrigues Ferreira, R. et al., "Determination of Aspartate Kinase Activity in Maize Tissues," Sci. Agric. (Piracicaba, Braz.), vol. 62, No. 2, 2005, pp. 184-189.
Rodrigues Ferreira, R. et al., "Isolation of enzymes involved in threonine biosynthesis from sorghum seeds," Braz. J. Plant Physiol., vol. 16, No. 2, 2004, pp. 95-104.
Shukla, V. et al., "Precise genome modification in the crop species *Zea mays* using zinc-finger nucleases," Nature Letters, vol. 459, 2009, pp. 437-442.
Teixeira, C. et al., "Isolation, Partial Purification and Characterization of Isoenzymes of Aspartate Kinase from Rice Seeds," Journal of Plant Physiology, vol. 153, 1998, pp. 281-289.
Thomas, D. et al., "Evolutionary relationships between yeast and bacterial homoserine dehydrogenases," Elsevier Science Publishers B.V., vol. 323, No. 3, 1993, pp. 289-293.
Verdaguer, B. et al, "Functional organization of the cassava vein mosaic virus (CsVMV)," Plant Molecular Biology, vol. 37, Belgium, 1998, pp. 1055-1067.
Zakin, M. et al., "Nucleotide Sequence of the metL Gene of *Escherichia coli*," The Journal of Biological Chemistry, vol. 258, No. 5, 1983, pp. 3028-3031.
Zhu-Shimoni, J. et al., "Expression of an *Arabidopsis* Aspartate Kinase/Homoserine Dehydrogenase Gene Is Metabolically Regulated by Photosynthesis-Related Signals but Not by Nitrogenous Compounds," Plant Physiol., vol. 116, 1998, pp. 1023-1028.
Zhu-Shimoni, J. et al., "Expression of an Aspartate Kinase Homoserine Dehydrogenase Gene Is Subject to Specific Spatial and Temporal Regulation in Vegetative Tissues, Flowers, and Developing Seeds," Plant Physiol., vol. 113, 1997, pp. 695-706.

* cited by examiner

| Construct | Stress intensity on site | Location | Year | Phenotype | Number of replicates | Control Yield (Qx/ha) | Construct Yield (Qx/ha) | % Yield of control | Avg(Prob.>f constrast) |
|---|---|---|---|---|---|---|---|---|---|
| T01789 | Low N stress | Location 1 | 2013 | Yield | 4 | 34.2 | 35.6 | 104 | 3.50E-01 |
| T01789 | Moderate N stress | Location 2 | 2013 | Yield | 4 | 41.5 | 44.3 | 106.7 | 3.00E-02 |
| T01789 | Low N stress | Location 2 | 2014 | Yield | 4 | 47 | 50.4 | 107.4 | 1.50E-03 |
| T01789 | Moderate N stress | Location 3 | 2014 | Yield | 4 | 51.3 | 52.2 | 101.9 | 4.90E-01 |
| T01789 | No stress | Location 1 | 2014 | Yield | 4 | 74.5 | 77.2 | 103.6 | 1.20E-01 |
| T01789 | No stress | Location 2 | 2014 | Yield | 4 | 55 | 57.8 | 105.2 | 8.70E-06 |

| Construct | Stress intensity on site | Location | Year | Phenotype | Number of replicates | Control Moisture | Transformed grains moisture | Moisture compared to control | Avg(Prob.>f constrast) |
|---|---|---|---|---|---|---|---|---|---|
| T01789 | Low N stress | Location 1 | 2013 | Moisture | 4 | 9 | 9.2 | 102.4 | 3.40E-01 |
| T01789 | Moderate N stress | Location 2 | 2013 | Moisture | 4 | 17.6 | 17.6 | 100.1 | 8.00E-01 |
| T01789 | Low N stress | Location 2 | 2014 | Moisture | 4 | 13.3 | 13.6 | 101.8 | 7.20E-02 |
| T01789 | Moderate N stress | Location 3 | 2014 | Moisture | 4 | 7.6 | 7.8 | 102 | 5.50E-01 |
| T01789 | No stress | Location 1 | 2014 | Moisture | 4 | 9.5 | 9.5 | 100.2 | 7.40E-01 |
| T01789 | No stress | Location 2 | 2014 | Moisture | 4 | 15.2 | 15.1 | 99.6 | 6.90E-01 |

| | Controls | Yield lost | Full N (kg/ha) | N stress conditions (kg/ha) | N stress application/Full N |
|---|---|---|---|---|---|
| 2013 | location 1 | Low N Stress | 13% | 90 | 28 | 30% |
| 2013 | location 2 | Moderate | 19% | 95 | 34 | 30% |
| 2014 | location 2 | Low N Stress | 8% | 78 | 11 | 15% |
| 2014 | location 3 | Moderate | 22% | 146 | 45 | 30% |

Figure 2

METHOD OF PLANT IMPROVEMENT USING ASPARTATE KINASE-HOMOSERINE DEHYDROGENASE

RELATED APPLICATIONS

This application is a national stage application (under 35 U.S.C. § 371) of PCT/EP2016/056948, filed Mar. 30, 2016, which claims benefit of European application EP 15305470.5, filed Mar. 31, 2015, both of which are incorporated herein by reference in their entirety.

The invention relates to the field of plant improvement, in particular of the improvement of yield for plants.

Aspartate Kinase (AK) and Homoserine Dehydrogenase (HSDH) are key regulatory enzymes in the aspartate amino acid pathway. They either function as monofunctional or bifunctional enzymes in bacteria, yeast and plants.

AK-HSDH is a bifunctional protein that contains both aspartate kinase and homoserine dehydrogenase activities.

This bifunctional enzyme is involved in the biosynthesis of aspartate-family amino acids. Indeed, AK-HSDH catalyzes the first and the third steps toward the synthesis of the essential amino acids threonine, isoleucine and methionine.

The bifunctional protein exists in *Escherichia coli* as AK I-HSDH I and AK II-HSDH II (Katinka et al. 1980 and Zakin et al. 1983). A monofunctional aspartate kinase called AK III also exists in *E. coli* (Cassan et al. 1986).

In yeast, the enzymes only exist in their monofunctional form. Thomas et al. (1993) described HOME, the gene encoding HSDH in *Saccharomyces cerevisiae* and Rafalski et al. (1988) revealed the structure of HOM3, the gene coding for aspartate kinase (AK) in yeast.

It has been shown that the bifunctional enzyme is present in many plant species such as *Arabidopsis thaliana* (Ghislain et al. 1994) or maize (Muehlbauer et al. 1994).

To study the spatial and temporal regulation of AK-HSDH, the GUS gene was placed downstream of the AK-HSDH promoter from *Arabidopsis thaliana* and the construct was transformed in tobacco by Zhu-Shimoni et al. (J. X. Zhu-Shimoni et al. 1997)(Zhu-Shimoni et Galili 1998). This gene was found to be retro-inhibited by threonine.

In US20060123505, one of the listed protein sequences SEQIDN® 46382 has similarity with the rice AK-HSDH protein but this sequence was not linked to any specific trait. In the description, it is mentioned that aspartate kinase is involved in the nitrogen metabolic system and has a possible use in breed improvement, without specifying in detail what this means and which trait would be improved. It is to be noted that, in the present invention, the protein has both aspartate kinase and homoserine dehydrogenase activities.

In US20120199144, the applicant used a modified AK-HSDH enzyme under the control of a senescence specific promoter to improve tobacco and more specifically the taste of tobacco. In particular, the AK-HSDH protein from *Arabidopsis thaliana* was modified using site directed mutagenesis to obtain a threonine insensitive aspartate kinase. The purpose of this patent application is clearly not to increase yield, which is the goal pursued in this patent application.

WO 2014/102773 describes a rice protein (SEQ ID NO: 6850) and indicates that it can be (as the other disclosed proteins) used to obtain plants presenting improved properties, amongst which increased yield.

The proteins disclosed in WO 2014/102773 have been identified through computer analysis, or are putative homologs of proteins identified by computer analysis. This patent application actually acknowledges that the data presented therein only suggests that the genes could lead to increased agronomic properties of plants (page 22, lines 20-25).

The rice protein as mentioned above is said to be a homolog of protein 321 (WNU81), and presents less than 85% identity with this protein. The results obtained with WNU81 are shown in Tables 37 and 38.

When using WNU81 as a transgene in *Arabidopsis*, this document only reports that there is increased biomass such as increased leaf area and root coverage (page 387, lines 20-25, pages 392 and 394), and potential better nitrogen absorption, but is silent with regards to increased yield, as defined in the present application. These data are confirmed in Tables 80, 81 and 84.

As a matter of fact, one of ordinary skill in the art knows that a biomass increase does not necessarily imply an increased yield or an increase of the production of grains and conversely, a biomass decrease does not necessarily imply a decrease in yield. For example, the article by Flintham et al. (J. Agric. Sci. 128 11-25, 1997) presents the creation of dwarf wheat varieties showing a better yield or better yield related characteristics (the number of grains for instance) than tall wheat varieties.

There is no direct correlation between biomass and yield or yield related characteristics. Peng et al. (Nature. 1999 Jul. 15; 400(6741):256-61) also note that the new wheat varieties are shorter because of an increased yield at the expense of straw biomass (abstract). Peng et al. also indicate that the height diminution is often associated with an increase in yield in several different crops (page 260 left column lines 13-14).

Consequently, WO 2014/102773 discloses some interesting data obtained with a protein that is said to be an homolog of SEQ ID NO: 2, but doesn't present any data making it possible to conclude that SEQ ID NO: 2 can actually be used to increase yield in plants, and in particular cereals such as demonstrated in the present application.

The applicant has shown that it is possible to increase yield by overexpressing an AK-HSDH enzyme, in particular, by using a constitutive promoter. Notably, the plants overexpressing AK-HSDH exhibit an increased yield even when the culture conditions present a nitrogen deficiency.

In agriculture, yield is the amount of product harvested from a given acreage (eg weight of seeds per unit area). It is often expressed in metric quintals (1 q=100 kg) per hectare in the case of cereals. It is becoming increasingly important to improve the yield of seed crops to feed an expanding population and, more recently, for biofuel production.

In the context of the present invention a cereal shall mean in particular maize, rice, wheat, barley, sorghum, millet, oats, rye, triticale (hybrid of wheat and rye), fonio, as well as two pseudocereals, namely buckwheat and *quinoa*.

Wheat is the preferred cereal according to the invention.

The invention provides constructs which can be used as a transgene for obtaining transgenic plants that have an increased yield with regards to isogenic plants that do not contain said transgene. In particular, the purpose is to have an increased yield, for the transgenic plants.

methods for obtaining a plant presenting increased yield by transforming plants with such construct, in order to obtain transgenic plants (yield is increased with regards to isogenic plants which do not bear the transgene)

transgenic plants containing such constructs as a transgene in their genome

Using the construct described herein, yield will be improved in plants, in particular wheat. Increase of yield is performed by overexpressing a nucleic acid sequence coding for an aspartate kinase-homoserine dehydrogenase (AK-HSDH) in a plant under the control of a plant promoter.

As intended herein, two plants are said to be "isogenic" with regards to a transgene when they differ at very few loci (less than 20, more preferably less than 10), and when one does carry the transgene, while the other does not. These plants can also be called "virtually isogenic" or "nearly-isogenic".

In a preferred embodiment, the present invention consists in overexpressing AK-HSDH (i.e. a protein presenting aspartate kinase-homoserine dehydrogenase activity) by transforming a plant with a T-DNA construct able to overexpress AK-HSDH under the control of a constitutive promoter. The rice Actin promoter was chosen for the experiments but other suitable promoters are available in the literature.

The present invention also comprise overexpressing an AK-HSDH in a plant after integration of a gene coding for such AK-HSDH within the genome of the plant, by gene targeting techniques. The gene encoding the AK-HSDH is inserted downstream an endogenous promoter of interest.

Techniques for performing targeted gene integration in plants are known by the person skilled in the art, and comprises the use of tools such as meganucleases, Zinc-Finger Nucleases (Shukla et al., Nature. 2009 May 21; 459(7245):437-41) and Transcription Activator-Like Effector Nucleases (Christian et al., Genetics. 2010 October; 186(2):757-61).

It is possible to use methods known in the art to determine the activity of a protein. In particular, the prior art has disclosed different methods to measure aspartate kinase-homoserine dehydrogenase enzymatic activity, all of which can be used in the context of the present application.

In particular, Paris et al. (J. Biol. Chem, Vol. 278, No. 7, pp. 5361-5366, 2003) disclose in vitro assays of AK activity in the forward direction by the hydroxamate method (Bryan et al (1970) Biochem. Biophys. Res. Commun. 41, 1211-1217). HSDH activity assays are also disclosed, in the reverse and forward directions (including methods to produce aspartate semi-aldehyde to conduct the forward assay).

Ferreira et al. (Sci. Agric. (Piracicaba, Braz.), v. 62, n. 2, p. 184-189, March/April 2005) disclose an assay to measure AK activity with reference to the method of Bonner & Lea (Enzymes of lysine synthesis. In: LEA, P. J. (Ed.) Methods in plant biochemistry: Enzymes of primary metabolism. London: Academic Press, 1990. v. 3, p. 297-315).

Ferreira et al. (Braz. J. Plant Physiol., 16(2):95-104, 2004) disclose an assay to measure AK activity with reference to the method of Brennecke et al. (Phytochemistry 41:707-712., 1996) as well as an assay to measure HSDH activity with reference to the method of Teixeira et al. (1998, J. Plant Physiol. 153:281-289).

In summary, there are multiple ways to measure the AK and the HSDH activity of a protein.

The invention thus relates to a nucleic acid construct comprising:
 a) a promoter active in plants, operatively linked to
 b) a nucleic acid coding for an aspartate kinase-homoserine dehydrogenase (AK-HSDH) protein.

In a preferred embodiment, said promoter is not a promoter that drives the expression of said AK-HSDH in nature.

In order to determine whether a promoter drives expression of said AK-HSDH in nature, it is sufficient to sequence the nucleic acid naturally present in 5' of the sequence of the AK-HSDH used and to determine said sequence. It is sufficient to sequence between 500 and 700 bases upstream from the ATG, but one can also sequence up to 1700 or 1000 bases upstream from the ATG.

The term "operably linked" as used herein means that the promoter and the AK-HSDH coding sequence are oriented such that the promoter directs expression of the AK-HSDH enzyme coding sequence, generally in the 5' to 3' direction.

The constructs may also contain enhancers (such as introns) and polyadenylation sites at the 3' end of the AK-HSDH coding sequence.

A promoter "active in plants" is a promoter that is able to drive expression of a gene operably linked thereto in a plant cell.

For being expressed, a sequence coding for the AK-HSDH may be present under the control of a constitutive, tissue specific, developmentally regulated, inducible or meiosis promoter.

Promoters may come from the same species or from another species (heterologous promoters). Although some promoters may have the same pattern of regulation when there are used in different species, it is often preferable to use monocotyledonous promoters in monocotyledons and dicotyledonous promoters in dicotyledonous plants.

In a preferred embodiment, said construct is under the control of a constitutive promoter.

Examples of constitutive promoters useful for expression include the 35S promoter or the 19S promoter (Kay et al., 1987, Science, 236:1299-1302), the rice actin promoter (McElroy et al., 1990, Plant Cell, 2:163-171), the pCRV promoter (Depigny—This et al., 1992, Plant Molecular Biology, 20:467-479), the CsVMV promoter (Verdaguer et al., 1998, Plant Mol Biol. 6:1129-39), the ubiquitin 1 promoter of maize (Christensen et al., 1996, Transgenic. Res., 5: 213), the regulatory sequences of the T-DNA of *Agrobacterium tumefaciens*, including mannopine synthase, nopaline synthase, octopine synthase.

The rice actin promoter depicted as SEQ ID NO: 3 is a preferred promoter usable in the context of the present invention.

Other suitable promoters could be used. It could be an inducible promoter, a developmentally regulated promoted or a tissue-specific promoter such as a leaf-specific promoter, a seed-specific, a BETL specific promoter and the like. Numerous tissue-specific promoters are described in the literature and any one of them can be used. One can cite the promoters disclosed in US 20130024998.

One can also cite the promoters regulated during seed development such as the HMWG promoter (High Molecular Weight Glutenin) of wheat (Anderson 0. D. et al., 1989, Theor Appl Genet, 77: 689-700; Roberts et al., 1989, Plant cell, 1: 569-578), the waxy, zein or bronze promoters of maize, or the promoters disclosed in US 20150007360, US 20120011621, US 20100306876, US 20090307795 or US 20070028327.

The invention also encompasses a vector containing the expression cassette (nucleic acid construct) of the invention.

A vector, such as a plasmid, can thus be used for transforming host cells. The construction of vectors for transformation of host cells is within the capability of one skilled in the art following standard techniques.

The decision as to whether to use a vector for transforming a cell, or which vector to use, is guided by the method of transformation selected, and by the host cell selected.

Where a naked nucleic acid introduction method is used, then the vector can be the minimal nucleic acid sequences necessary to confer the desired phenotype, without the need for additional sequences.

Possible vectors include the Ti plasmid vectors, shuttle vectors designed merely to maximally yield high numbers of copies, episomal vectors containing minimal sequences necessary for ultimate replication once transformation has occurred, transposon vectors, including the possibility of RNA forms of the gene sequences. The selection of vectors and methods to construct them are commonly known to persons of ordinary skill in the art and are described in general technical references (Mullis, K B (1987), Methods in Enzymology).

For other transformation methods requiring a vector, selection of an appropriate vector is relatively simple, as the constraints are minimal. The apparent minimal traits of the vector are that the desired nucleic acid sequence be introduced in a relatively intact state. Thus, any vector which produces a plant carrying the introduced DNA sequence should be sufficient. Also, any vector which introduces a substantially intact RNA which can ultimately be converted into a stably maintained DNA sequence should be acceptable.

For transformation methods within a plant cell, one can cite methods of direct transfer of genes such as direct micro-injection into plant embryos, vacuum infiltration or electroporation, direct precipitation by means of PEG or the bombardment by gun of particles covered with the plasmidic DNA of interest.

It is preferred to transform the plant cell with a bacterial strain, in particular *Agrobacterium*, in particular *Agrobacterium tumefaciens*. In particular, it is possible to use the method described by Ishida et al. (Nature Biotechnology, 14, 745-750, 1996) for the transformation of Monocotyledons.

However, any additional attached vector sequences which confer resistance to degradation of the nucleic acid fragment to be introduced, which assists in the process of genomic integration or provides a means to easily select for those cells or plants which are actually, in fact, transformed are advantageous and greatly decrease the difficulty of selecting useable transgenic plants.

The vector can exist, for example, in the form of a phage, a plasmid or a cosmid. The construction of such expression vectors for transformation is well known in the art and uses standard techniques. Mention may be made of the methods described by Sambrook et al. (1989).

For transforming bacteria, a vector is generally defined as being a nucleic acid molecule that possesses elements that allows it to be maintained within said host cell (such as an origin of replication that works in this bacterial host cell).

The invention also encompasses a host cell containing the expression cassette as described above.

The decision as to whether to use a given host cell, or which host cell to use, is guided by the method of transformation.

The host cell can be any prokaryotic or eukaryotic cell. Any of a large number of available and well-known host cells may be used in the practice of this invention. The selection of a particular host is dependent upon a number of factors recognized by the art. These include, for example, compatibility with the chosen expression vector, bio-safety and costs. Useful hosts include bacteria such as *E. coli* sp. or *Agrobacterium*. A plant host cell, may be also used, notably an Angiosperm plant cell, Monocotyledon as Dicotyledon plant cell, particularly a cereal or oily plant cell, selected in particular from the group consisting of maize, wheat, barley, rice, rape and sunflower, preferentially wheat.

More particularly, the host cell used in carrying out the invention is *Agrobacterium tumefaciens*, according to the method described in the article of An et al., 1986, or *Agrobacterium rhizogenes*, according to the method described in the article of Jouanin et al., 1987.

In a specific embodiment, said expression cassette is stably integrated within the genome of said host cell. This embodiment is particularly interesting for plant host cells. Stable integration within the genome means that the expression cassette can be transmitted to the progeny of said host cell upon division.

The invention also encompasses a plant containing at least one cell containing the expression cassette as defined above, preferably stably integrated within its genome.

A part of a transgenic plant, in particular fruit, seed, grain or pollen, comprising such a cell or generated from such a cell is also encompassed by the invention.

It is reminded that a whole plant can be regenerated from a single transformed plant cell. Thus, in a further aspect the present invention provides transgenic plants (or parts of them) including the expression cassette according to the invention. The regeneration can proceed by known methods.

The seeds which grow by fertilization from this plant, also contain this transgene in their genome.

Said plant or part of a plant according to the invention can be a plant or a part of it from various species, notably an Angiosperm, Monocotyledons as Dicotyledons.

It is preferably a cereal or oily plant. As used herein, the term "oily plant" denotes a plant that is capable of producing oil, and preferably that is cultivated for oil production.

Said plant is preferably selected from the group consisting of maize, rice, wheat, barley, rape and sunflower. In a preferred embodiment, said plant is wheat.

The invention thus relates in particular to a transgenic wheat, containing at least one cell comprising, stably integrated in its genome, the expression cassette of the invention.

In a specific embodiment, said plant, in particular said wheat, comprises multiple cells containing, stably integrated in their genome, the expression cassette of the invention. In this embodiment, it is possible that some cells of said plant do not contain the transgene.

In another embodiment, said transgene (comprising the expression cassette of the invention) is present in all cells of said plant, in particular said wheat.

In another embodiment, the transgene is introduced within the plant cells such as being expressed transiently, or through a genetic construct not integrated in the genome. Thus, agro-infiltration or any other methods, such as injection or spray, are contemplated for transient expression.

Hybrid plants obtained by crossing plants according to the invention also form part of the invention, when they contain at least one cell containing the expression cassette of the invention.

Any plant as described above can contain one or more transgenes in addition to the cassette according to the invention. One may mention transgenes conferring male sterility, male fertility, resistance to a herbicide (notably glyphosate, glufosinate, imidazolinone, sulfonylurea, L-phosphinotricine, triazine, benzonitrile), resistance to insects (notably a transgene coding for a *Bacillus thuringiensis* toxin), tolerance to water stress. These plants can be obtained by crossing said plants of the invention with other plants containing said transgenes. Alternatively, plants can be co-transformed with an expression cassette containing several different transgenes, including the transgene of the invention.

As demonstrated in the examples, said transgenic plants comprising an expression cassette according to the invention present an increased yield as compared to control plants corresponding to non-transgenic plants not comprising said expression cassette.

Said increased yield may be observed in normal conditions or in stress conditions.

Increased yield in stress conditions (or stress tolerance) can be measured by the ability of the transgenic plant to maintain yield under stress conditions compared to normal conditions (which is considered to be achieved when the yield observed in stressed conditions is at least 90%, 94%, 95%, 96%, 97%, 98%, 99% or 100% of the yield obtained for the same plant in non-stressed (normal) conditions). It can also be measured by the ability of the transgenic plant to increase yield under stress conditions compared to control plants grown under stress conditions (at least 101%, 102%, 103%, 104%, 105%, 106%, 107%, 108%, 109%, 110%, 111%, 112%, 113%, 114%, 115%).

As intended herein, stress conditions comprise specific conditions that are applied to a plant at a specific development stage such as that they induce a yield decrease of at least 8%, 10%, preferentially at least 15% and more preferentially at least 20% between the control plants in normal and in stress conditions. As a matter of illustration, one can cite heat stress conditions that may be applied during the flowering stage (in particular for wheat) or hydric stress before the flowering stage or after the fertilization, (in particular during the grain filling stage for maize).

In the present invention nitrogen stress (as disclosed in the examples) is a stress for which the transgenic plants of the invention would present maintained or increased yield with regards to isogenic plants.

In a particular embodiment, the sequence of said AK-HSDH is SEQ ID NO: 2, coded by SEQ ID NO: 1.

In a specific embodiment, the nucleic acid construct has the sequence SEQ ID NO: 8 (corresponding to preferred construct including, in particular the rice actin promoter and the AK-HSDH gene of SEQ ID NO: 1).

It is to be noted that SEQ ID NO: 2 (resp. SEQ ID NO: 1) represents and exemplifies an allele of the AK-HSDH protein (resp. gene) in rice. Other alleles of this protein in the same organism, which all possess the same activity than this protein, could be used in the above-identified nucleic acid construct.

In the context of the invention (such as the processes, constructs, cells, transgenic plants disclosed herein), one can also use orthologs of said proteins, such as the proteins disclosed as SEQ ID NO: 9 to SEQ ID NO: 21, to obtain the same technical effect.

Any embodiment pertaining to SEQ ID NO: 2 is usable in the same way for any one of SEQ ID NO: 9 to SEQ ID NO: 21, and any such embodiment as applied to any one of SEQ ID NO: 9 to SEQ ID NO: 21 is thus part of the invention. In particular, one can use SEQ ID NO: 9, which is a soybean (*Glycine max*) AK HDSH protein.

In particular, one can use SEQ ID NO: 10, which is an *Escherichia* coli AK HDSH protein (AK-HSDH I).

In particular, one can use SEQ ID NO: 11, which is an *Escherichia* coli AK HDSH protein (AK-HSDH II).

In particular, one can use SEQ ID NO: 12, which is another *Arabidopsis thaliana* AK HDSH protein (AK-HSDH I).

In particular, one can use SEQ ID NO: 13, which is another *Arabidopsis thaliana* AK HDSH protein (AK-HSDH II).

In particular, one can use SEQ ID NO: 14, which is a Brachypodium distachyon AK HDSH protein.

In particular, one can use SEQ ID NO: 15, which is a maize (*Zea mays*) AK HDSH protein.

In particular, one can use SEQ ID NO: 16, which is a maize (*Zea mays*) AK HDSH protein.

In particular, one can use SEQ ID NO: 17, which is a barley (*Hordeum vulgare*) AK HDSH protein.

In particular, one can use SEQ ID NO: 18, which is a barley (*Hordeum vulgare*) AK HDSH protein.

In particular, one can use SEQ ID NO: 19, which is a rice (*Ozyza sativa*) AK HDSH protein.

In particular, one can use SEQ ID NO: 20, which is a *Triticum urartu* AK HDSH protein.

In particular, one can use SEQ ID NO: 21, which is an *Aegilops tauschii* AK HDSH protein.

This list is not exhaustive, and other AK-HSDH proteins can also be used in said nucleic acid construct, to obtain transgenic plant and the same technical effect as disclosed herein.

These may be identified from databases, by applying the BLASTP program (especially the BLASTP 2.2.29 program) (Altschul et al., (1997), Nucleic Acids Res. 25: 3389-3402; Altschul et al., (2005) FEBS J. 272: 5101-5109) preferably to SEQ ID NO: 2, but alternatively to any one of the other sequences 9 to 21 as disclosed above using the following algorithm parameters:

Expected threshold: 10
Word size: 3
Max matches in a query range: 0
Matrix: BLOSUM62
Gap Costs: Existence 11, Extension 1.
Compositional adjustments: Conditional compositional score matrix adjustment
No filter for low complexity regions The proteins that can be used in the context of the above construct are preferably the ones that present a Max score above 1000.

They would also preferably present an identity (as indicated by the BLASTP software) equal or above 80%, preferably equal or above 85%, preferably equal or above 90%, preferably, equal or above 95% more preferably equal or above 97% more preferably equal or above 98%, more preferably equal or above 99%.

However, it is to be noted that AK-HSDH proteins that can be expressed by transgenic plants and used in the processes disclosed herein can also present a lower level of identity. In particular, one can note the *Escherichia coli* AK-HSDH genes and proteins, as disclosed in SEQ ID NO: 10 and SEQ ID NO: 11 (especially such protein) can similarly and equivalently be used in the processes and within nucleic constructs as disclosed herein.

Consequently, one could use a protein presenting an identity with SEQ ID NO: 2, or to any one of SEQ ID NO: 9 to SEQ ID NO: 21, and in particular to SEQ ID NO: 10 or SEQ ID NO: 11 (as indicated by the BLASTP software) equal or above 80%, preferably equal or above 85%, preferably equal or above 90%, preferably, equal or above 95% more preferably equal or above 97% more preferably equal or above 98%, more preferably equal or above 99%.

Using these similar sequences to produce transgenic plants makes it possible to obtain an equivalent technical effect as the one presented in the present application:

increase of yield for these transgenic plants (as compared with isogenic plants not carrying the transgene), in particular in stressed conditions, and specifically in nitrogen stress conditions.

The invention also relates to various methods of using the plants of the invention.

Therefore, the invention also relates to a method for obtaining a transgenic plant containing at least one cell comprising a transgene comprising the expression cassette as described above, comprising the steps consisting of:
 a) transforming at least a plant cell or plant tissue with a vector containing the nucleic acid construct according to the invention;
 b) cultivating the cell(s) or plant tissue thus transformed so as to generate a plant containing in its genome at least the expression cassette of the invention, whereby said generated plant contains at least one cell which comprises the transgene comprising the expression cassette as described above.

In particular, the invention encompasses a method for increasing yield in a plant, comprising the steps consisting of:
 a) transforming at least a plant cell or plant tissue with a vector containing, as a transgene, a nucleic acid construct comprising:
  i. a promoter active in plants, operatively linked to
  ii. a nucleic acid coding for a aspartate kinase-homoserine dehydrogenase (AK-HSDH) protein;
 b) cultivating the cell(s) or plant tissue thus transformed so as to generate a transgenic plant containing at least a cell which contains, in its genome, at least said nucleic acid construct.

wherein said plant presents a increased yield than a plant isogenic but for said nucleic acid construct.

The nucleic acid construct is as disclosed above.

Said generated plant may present an increased yield, in normal or stressed conditions, as compared to an isogenic plant that does not contain said expression cassette in its genome, or shall be able to maintain the yield observed in normal conditions when grown in stressed conditions.

As disclosed above, the stress may be any biotic or abiotic stress, but is preferably a nitrogen stress, wherein this stress is described in the examples.

In this method, it is clear that the measure of yield is checked by sowing and harvesting of a multiplicity of plants that contain the transgene, the yield of which is then compared with the yield obtained with a second group of plants not containing said transgene, and this under the same culture conditions (sowing and harvest at the same time, on comparable parcels, use of the same amount of fertilizers, water . . . ).

It is also clear that comparison is to be performed on a second group of plants that is isogenic to the plants having the transgene. As indicated above, these "isogenic" plants differs from the plants harboring the transgene at very few loci (less than 20, more preferably less than 10), in addition to not carry said transgene. In particular a plant carrying the transgene isogenic to another plant of interest may be obtained by at least four backcrosses in the isogenic plant of interest, followed by at least one self-fertilization. Preferably, the isogenic plants are homozygous lines.

Said generated plant can also be used in a selection (breeding) process for obtaining a plant with improved yield.

The invention thus also relates to a method for producing a plant that can be used in a selection (breeding) process or scheme for obtaining a plant with improved yield, comprising the step of transforming a plant cell with a vector according to the invention, and regenerating a transgenic plant which comprises at least one cell which contain the transgene comprising the expression cassette as described above.

The introgression of the transgene in a given plant is in particular carried out by methods known in the art (crossing and self-pollination). The plants are in particular selected using molecular markers.

The principle is recalled below:

A series of back crosses are performed between the elite line (in which one wishes to introduce the determinant) and a line that already carries said determinant (the donor line). During the back crosses, one can select individuals carrying the determinant and having recombined the smallest fragment from the donor line around the determinant. Specifically, by virtue of molecular markers, the individuals having, for the markers closest to the determinant, the genotype of the elite line are selected.

In addition, it is also possible to accelerate the return to the elite parent by virtue of the molecular markers distributed over the entire genome. At each back cross, the individuals having the most fragments derived from the recurrent elite parent will be chosen.

Such breeding and selection programs are important as it is often preferable to sow and harvest plant lines that have been optimized, in particular for the location in which they are cultured. Consequently, one needs to introduce the transgene in said adapted lines having otherwise agronomic quality characteristics.

The invention also relates to a method for obtaining a plant containing a transgene, wherein said transgene comprises the expression cassette as described above, comprising the steps of
 a) Performing the method as described above (transformation of plant cells and regeneration) in order to obtain a transgenic plant, wherein said transgene comprises said expression cassette,
 b) crossing said transgenic plant with a plant line which does not contain said transgene (the receiver plant line)
 c) selecting, among the progeny, plants that contain said transgene and that have a good genome ratio with regard to said receiver plant line,
 d) back-crossing said selected plants with said receiver plant line
 e) repeating steps c) and d) if necessary until a line isogenic with said receiving line (and containing said transgene) is obtained,
 f) optionally, performing self-fertilization in order to obtain a plant that is homozygous for the transgene.

Step c) is preferably performed, by genotyping using molecular markers (for example microsatellite markers), making it possible to define the contribution of each of the two parents to the progeny. One would thus select, in the progeny, plants carrying the transgene and having more markers from the receiver plant line than from the parent containing the transgene.

This step is thus performed in vitro.

Plants (in particular maize or wheat) which possess the transgene, may also be selected from the progeny, in a conventional manner by molecular biology methods (such as PCR or Southern blotting).

The invention also relates to a method for growing a plant, comprising the step of sowing a plant seed, wherein said plant seed contains the nucleic acid construct as described above, and growing plants from this sowed seed.

The invention also relates to a method for increasing plant yield under normal conditions for plant harvest, comprising the step of sowing plant seeds, wherein said plant seeds contain the expression cassette of the invention and growing plants from these sowed seeds, and wherein the yield obtained from said grown plants is increased as compared to the yield obtained from isogenic plants grown from seeds which do not contain said expression cassette The invention also relates to a method for increasing or maintaining plant yield under stressed conditions, comprising the step of sowing plant seeds, wherein said plant seeds contain the nucleic acid construct as described above, and growing plants from these sowed seeds, wherein the growing phase is made under stress conditions, and wherein the yield obtained from said grown plants is increased as compared to the yield obtained from plants grown from seeds which do not contain said nucleic acid construct or the yield obtained from said grown plants is maintained as compared to the yield obtained from plants containing said nucleic acid construct and grown in normal conditions.

The invention also relates to a method of growing plants, comprising the step of sowing seeds containing the nucleic acid construct as described above, and growing plants from the sowed seeds.

The invention may also comprise the step of harvesting said plants.

The invention also relates to a method for harvesting plants comprising the step of harvesting plants of the invention.

In particular, in the methods as described above, a nitrogen stress is applied to the plants during their growth.

A method for selecting (i.e. screening for, identifying) a plant that can be used in a selection (breeding) process for obtaining a plant with improved yield, which comprises the step of selecting, in a population of plants, the plants containing the expression cassette and transgene as described above, is also part of the invention.

Such method is thus an in vitro method, intended to identify, in a population of plants, the ones that carry the transgene according to the invention.

A breeding process for obtaining a plant with improved yield is performed as follows: the yield of a plurality of plants gives the reference yield level which is to be improved. The plant with improved yield is obtained, when the yield observed after sowing and harvesting said plant is higher than the yield of reference. Said plant with improved yield is obtained by known methods in the art, by crossing, back-crossing and stabilizing plants which present a yield In a specific embodiment, the selection is performed through the use of a marker that is specific to the transgene. In this embodiment, the selection step is thus preferably preceded by a step comprising genotyping said population of cereals.

In a specific embodiment, the selection step is preceded by a step comprising extracting the RNA from the individuals in said population.

In a specific embodiment, the selection step is preceded by a step comprising extracting proteins from the individuals in said population.

In a specific embodiment, said population is the progeny obtained from crossing a transgenic plant, wherein said transgene comprises the expression cassette as described above, with a plant line which does not contain said transgene (the receiver plant line).

A method for identifying a plant with improved yield, which comprises the step of identifying, in a population of plants, the plants containing the expression cassette or transgene as described above, is also part of the invention. Improved yield is determined after comparison with isogenic plants which do not contain the expression cassette or transgene.

In a specific embodiment, the identification is performed through the use of a marker that is specific to the transgene. In this embodiment, the identification step is thus preferably preceded by a step comprising genotyping said population of cereals.

In a specific embodiment, the identification step is preceded by a step comprising extracting the RNA from the individuals in said population.

In a specific embodiment, the identification step is preceded by a step comprising extracting proteins from the individuals in said population.

In a specific embodiment, said population is the progeny obtained from crossing a transgenic plant, wherein said transgene comprises the expression cassette as described above, with a plant line which does not contain said transgene (the receiver plant line).

The invention also relates to a method for obtaining a hybrid plant, wherein said hybrid plant contains the expression cassette as described above stably integrated within its genome. Said method comprises the step of crossing a first homozygous line, which contains said expression cassette stably integrated within its genome, with a second homozygous line.

This plant can be homozygous (if each homozygous parent has the expression cassette as described above stably integrated within its genome) or heterozygous for the transgene present on said expression cassette.

In a preferred embodiment, the methods are applied to a cereal (in particular, rice, maize, wheat, barley). It is preferred when said plant is maize or wheat.

DESCRIPTION OF THE FIGURES

FIG. 2: Comparison of yield for wheat plants containing the AK-HSDH construct and controls.

EXAMPLES

Example 1: Transcriptomic Data

1) Materials & Methods

Wheat leaf samples were collected on 2 trials (La Miniere and Boigneville stations—Arvalis Institut du Végétal; France): one in field for cultivar Arche and in greenhouse for cultivar Soissons. Different nitrogen treatments were applied to lead to samples with a range of Nitrogen Nutrional Index (NNI) from 0.39 to 1.58.

During wheat culture, sampling was done at different stages.

Total RNAs were extracted from all the samples with the "SV96 Total RNA Isolation System" (Promega) according to the manufacturer recommendations. RNA integrity was verified on the Agilent Bioanalyzer and presence of potential genomic DNA was checked by QPCR on RNA. In the absence of genomic DNA no amplification is expected from RNA.

For each sample, 2 µg of total RNA were submitted to the reverse transcription using the "High capacity reverse transcription kit" (Applied Biosystems) and random primers in 100 µl. RT reaction was then 1/10th diluted and 2 µl of cDNA used for the amplification. Each RNA sample was submitted to 2 independent RT reactions for technical reproducibility evaluation.

Quantitative PCR was performed on an ABI7900 machine (Applied Biosystems), using Applied Biosystems reagents. The PCR reactions consisted of a hot-start Taq Polymerase activation step of 95° C. for 5 minutes, followed by 2 steps amplification cycles (denaturation 95° C., 30 sec, annealing/elongation 60° C., 1 min). Expression levels of mRNA for AK-HSHD gene were calculated using the Ct estimated by the SDS software (Applied Biosystems) and normalized across samples using 4 control genes. Relative expression was then considered as the ΔCt between AK_HSHD gene and the average of controls.

2) Results

In order to validate the role of the AK-HSHD gene in Nitrogen stressed conditions, an experiment on two bread wheat genotypes, i.e. Arche and Soissons, was conducted on leaf and root samples for Arche and for Soissons collected at different stages under different nitrogen constraints.

The N nutrition index (NNI) value was calculated for each sample. Moreover, for the same samples, RNA was extracted and the expression pattern of AK_HSHD was analysed by qPCR using sequence specific primers forward: GATGTGCGTGTCATCGGAATA; SEQ ID NO: 6 reverse: CATCACTTCTGCTTGTCGGC; SEQ ID NO: 7

Figure 1:
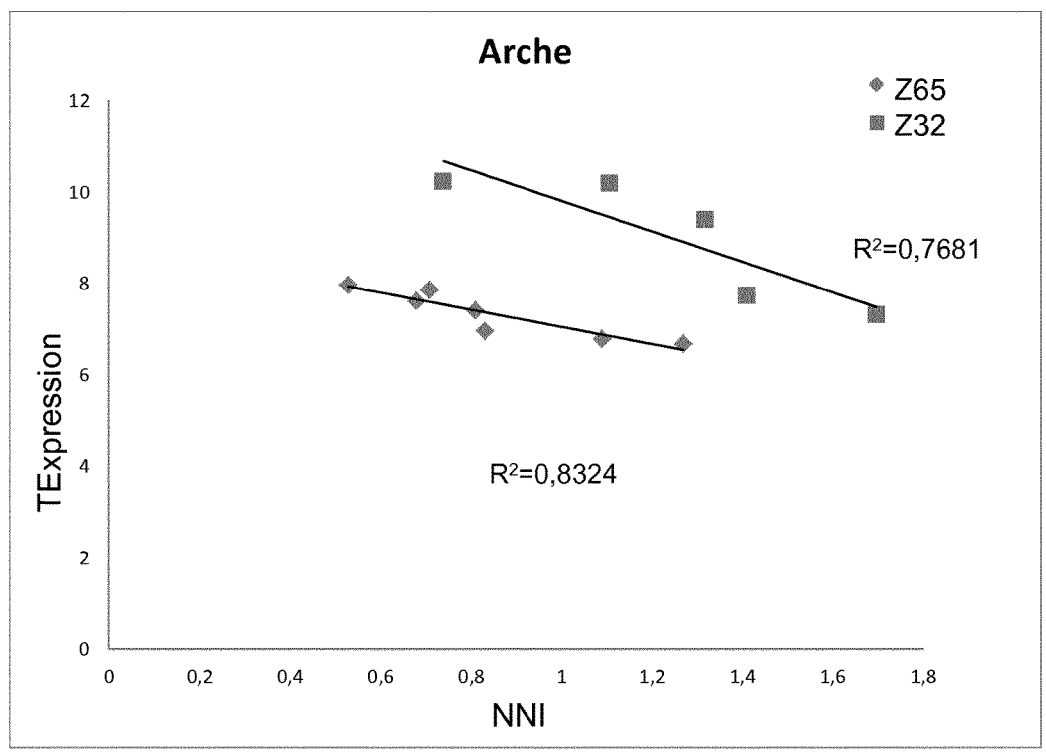
FIG. 1 A: Level of expression (ΔΔCT) for AK-HSHD gene, and NNI on Arche genotypes in roots at 2 stages (Z32 and Z65 (Zadoks scale)). B: Level of expression (ΔΔCT) for AK-HSHD gene, and NNI for leaf samples on Soissons genotypes on leaf samples at Z30 and Z44 stages (Zadoks scale).
Figure 1:
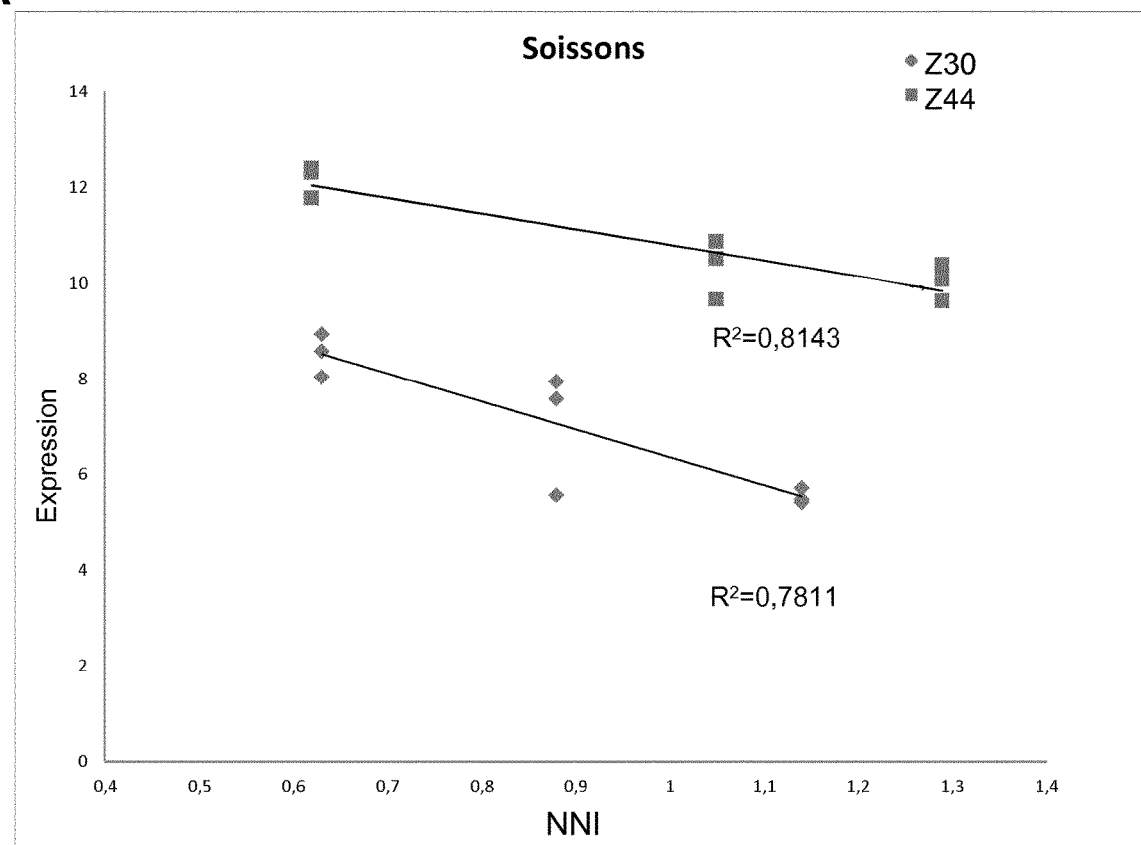

The results are shown in FIG. 1.

Significant correlations of $R^2$=0.80 (mean of $R^2$ correlation at Z32 and Z65 on root samples) and 0.80 (mean of $R^2$ correlation at Z30 and Z44 on leaf samples) were found between the expression (ΔΔCT values) of the AK-HSHD gene and the NNI score of the samples for both the Arche and Soissons genotypes, respectively, suggesting a role of AK-HSDH in nitrogen metabolism and yield establishment.

Example 2: Association Studies in Wheat

The aim of association studies is to identify loci contributing to quantitative traits, based on the statistical association between genotypes and phenotypes using a large germplasm collection (panel) without knowledge on pedigree.

Contrary to linkage mapping, association studies can be performed using a selection of cultivars without the need for crossing and screening offsprings. In this way, one can look at a maximum of genotypic variability (depending on panel selection) in a single study. Thus, using this technique, it is possible to identify favorable alleles of the AK-HSHD gene linked to phenotypic data, with a high resolution.

A SNPs discovery was performed for the AK-HSDH gene, that are then linked to phenotypic data. The expected results were a positive association between SNPs and phenotypic data to conclude on the implication of the gene in the QTL's effect (Linkage Disequilibrium in the area has to be considered). Association study can provide information on gene polymorphisms implicated in traits and can indicate which allele is favorable regarding these traits.

In AK-HSHD, a SNP (BWS5547) showed significant association results between genotypic and phenotypic data on traits like yield, grain protein content, biomass and yield in Nitrogen stressed conditions).

Example 3: Cloning of AK-HSDH Downstream the Rice Actin Promoter and Transformation The AK-HSDH sequence was cloned via a GATEWAY LR reaction, between a rice Actin promoter (proActin) (McElroy et al. 1990) plus an Actin intron (intActin, exemplified in SEQ ID NO: 4) (McElroy et al. 1990), and a 3' Nopaline synthase (Nos) termination sequence (tNos, depicted in SEQ ID NO: 5) (Depicker et al. 1982), into the destination binary plasmid pSC4Act-R1R2-SCV forming pBIOS1779.

The binary vector pSC4Act-R1R2-SCV is a derivative of the binary vector pSCV nos nptII which is a derivative of pSCV1 (Firek et al. 1993) which contains a nos promoter driving a Kanamycin resistance gene, cloned between the EcoRV and EcoRI sites of pSCV1.

The pBIOS1779 plasmid was transferred into agrobacteria EHA105 according to Komari et al. (1996). Wheat cultivar (NB01) was transformed with these agrobacterial strains essentially as described by WO2000063398.

Similarly, four other constructs were made and inserted in the destination binary plasmid pSC4Act-R1R2-SCV forming pBIOS10221, pBIOS10227, pBIOS10233 and pBIOS10249 plasmids ready for transformation.

pBIOS10221 is comprising an optimized sequence of the rice AK-HSDH gene (SEQ ID No: 1) encoding SEQ ID NO: 2 for expression in wheat. This sequence is cloned downstream of the sorghum promoter SvPEPc_C4 (SEQ ID NO: 23) and upstream of the terminator AtSac66 (SEQ ID NO: 24). The full construct sequence is given in SEQ ID NO: 22.

pBIOS10227 is comprising an optimized sequence of the rice AK-HSDH gene (SEQ ID NO: 1) encoding SEQ ID NO: 2 cloned downstream of a modified version of the rice Actin promoter (SEQ ID NO: 26) and upstream of the terminator AtSac66 (SEQ ID NO: 24). The full construct sequence is given in SEQ ID NO: 25.

pBIOS10233 is comprising an optimized sequence of *E. coli* AK-HSDH gene encoding SEQ ID NO 11 for expression in wheat. This sequence is cloned downstream of proActin (SEQ ID NO: 26) and upstream of the terminator AtSac66 (SEQ ID NO: 24). The full construct sequence is given in SEQ ID NO: 27.

pBIOS10249 is comprising an optimized sequence of the rice AK-HSDH gene (SEQ ID NO: 1) encoding SEQ ID NO: 2 for expression in corn cloned downstream of the rice ubi3 promoter (SEQ ID NO: 29) and upstream of the sugarcane terminator SoUbi4 (SEQ ID NO: 30). The full construct sequence is given in SEQ ID NO: 28.

The pBIOS10249 plasmid was transferred into agrobacteria LBA4404 (pSB1) according to Komari et al. (1996). Maize cultivar A188 was transformed with this agrobacterial strain essentially as described by Ishida et al. (1996).

All the above plasmids, constructs and transgenes are part of the invention, and can be used in plants or in methods as disclosed above. The use of the constructs as disclosed above is not restricted to the plants mentioned above.

Example 4: Wheat and Corn Field Trials

Field trials show that seed yield and particularly yield in nitrogen deficient conditions is improved when AK-HSDH is overexpressed.

1) Field Trials:

Homozygous transgenic lines were self-pollinized for seed increase. T4 (proActin-intActin-AK-HSDH-terNos) homozygous plants were used for field trials.

Controls are obtained by bulking null segregant siblings isolated from T1 segregation. The null segregants are used as a reference for statistical analysis. They thus differ from the tested lines at very few loci, and for the presence of the transgene. These control are thus quasi-isogenic to the tested lines.

Improved yield was observed for wheat plants containing the AK-HSDH construct as compared to the controls, as can be seen in FIG. 2.

Field evaluation was performed under two Nitrogen conditions:

In normal (optimal) growing condition with an optimal Nitrogen fertilization. The applied Nitrogen rate was calculated using local guideline.

In nitrogen stress condition, the applied Nitrogen rate was between 0 and 50% of the optimal Nitrogen rate.

After harvest, the stress intensity of the N stress condition was eventually characterized, based on the seed yield lost compare to the seed yield of the normal condition. The N stress intensity is generally characterized based on the approximate following categories.

| Nitrogen stress level | Seed yield lost compare to the optimal condition |
|---|---|
| Low N stress condition | 0 to 15% |
| Moderate N stress condition | 15% to 30% |
| Strong N stress condition | Above 30% |

Yield was calculated as follows:

During harvest, grain weight and grain moisture are measured using on-board equipment on the combine harvester.

Grain weight is then normalized to moisture at 15%, using the following formula:

Normalized grain weight=measured gain weight×(100-measured moisture (as a percentage))/85 (which is 100-normalized moisture at 15%)

As an example, if the measured grain moisture is 25%, the normalized grain weight will be: normalized grain weight=measured grain weight×75/85.

Yield is then expressed in a conventional unit (such as quintal per hectare).

The corn field trials are assessed as described above for the wheat

2) Experimental Design:

Field trials were conducted in 2013 (2 N stress locations) and 2014 (1 N stress location, 1 N stress and yield location, 1 yield location)

In 2013, plants were sown between April 23 (location 1) and May 11th (location 2).

In 2014, plants were sown between April 16 and May 17th.

The experimental design was Randomized complete block or Lattice with 4 replicate seeded at 360 seeds/m².

A bulk of null segregant of the construct was used as control in these experiments. 4 transgenic events of the construct T01789 were used for the field trials in 4 replicates.

Results are represented in FIG. 2 with the yield expressed in (Qx/ha) and in percentage compared to the control.

Under nitrogen deficiency (ND) conditions, in 2013 the observed yield ranged from 91.7% to 120.5% of the mean of the yield of the controls with a global average of 105.5%. No effect on seed moisture content was observed.

Under nitrogen deficiency (ND) conditions, in 2014 the observed yield ranged from 98.4% to 112.3% of the mean of the yield of the controls with a global average of 104.6%. No effect on seed moisture content was observed.

Under standard conditions, in 2014 the yield observed ranged from 98.6% to 110.3% of the mean of the yield of the controls with a global average of 105.2%. No effect on seed moisture content was observed.

This figure demonstrates that the transgenic plants present an increased yield stability (normalized for moisture). No other phenotypes were observed for these plants.

The invention claimed is:

1. A method for increasing plant yield, wherein yield is the weight of seeds per unit area, comprising the steps of sowing seeds of wheat, and growing plants from these sowed seeds, wherein the seeds are transgenic wheat seeds containing, in the genome, a transgene comprising a nucleic acid construct comprising:
    i. a promoter active in plants, wherein the promoter is a constitutive promoter, operatively linked to
    ii. a nucleic acid coding for an aspartate kinase-homoserine dehydrogenase (AK-HSDH) protein, wherein the AK-HSDH comprises the amino acid sequence set forth in SEQ ID NO:2; and
    wherein the yield obtained from said grown plants is increased as compared to the yield obtained from plants grown from seeds which do not contain said nucleic acid construct.

2. A method for increasing or maintaining plant yield under stressed conditions, wherein yield is the weight of seeds per unit area, comprising the steps of sowing seeds of wheat, and growing plants from these sowed seeds, wherein the seeds are transgenic wheat seeds containing, in the genome, a transgene comprising a nucleic acid construct comprising:
    i. a promoter active in plants, wherein the promoter is a constitutive promoter, operatively, linked to
    ii. a nucleic acid coding for an aspartate kinase-homoserine dehydrogenase (AK-HSDH) protein, wherein the AK-HSDH comprises the amino acid sequence set forth in SEQ ID NO:2, and
    wherein the growing phase is made under stress conditions, and
    wherein the obtained from said grown plants is increased as compared to the yield obtained from plants grown from seeds which do not contain said nucleic acid construct or the yield obtained from said grown plants is maintained as compared to the yield obtained from plants containing said nucleic acid construct and grown in normal conditions.

3. The method of claim 1, wherein said promoter is an actin promoter comprising SEQ ID NO: 3.

4. The method of claim 1, wherein said nucleic acid construct has the sequence SEQ ID NO: 8.

5. The method of claim 2, wherein said promoter is an actin promoter comprising SEQ ID NO: 3.

6. The method of claim 2, wherein said nucleic acid construct has the sequence SEQ ID NO: 8.

7. The method of claim 2, wherein the stress conditions include nitrogen deficiency.

8. The method of claim 1, wherein said promoter comprises SEQ ID NO: 26.

9. The method of claim 1, wherein said promoter is a PEPC promoter comprising SEQ ID NO: 23.

10. The method of claim 1, wherein said promoter is a rubi3 promoter comprising SEQ ID NO: 29.

11. The method of claim 2, wherein said promoter comprises SEQ ID NO: 26.

12. The method of claim 2, wherein said promoter is a PEPC promoter comprising SEQ ID NO: 23.

13. The method of claim 2, wherein said promoter is a rubi3 promoter comprising SEQ ID NO: 29.

* * * * *

SEQUENCE LISTING

```
<160> NUMBER OF SEQ ID NOS: 30

<210> SEQ ID NO 1
<211> LENGTH: 2751
<212> TYPE: DNA
<213> ORGANISM: Oryza sativa

<400> SEQUENCE: 1
atggctcgta gtctcgctgt cgccagccca ctcccaccgg cggcagcggt caggcgccgt      60
ccacgggcat cggcctccgg acgggaggtc atcagccagt gctggaagtg cgagatcaac     120
caggatcaac cacttggcaa tagcctcaga attgggcact ctcaagggtc actccaacgc     180
cacggcagta ggaacttgct cgcggccgcg gccgctatct ccattgagca agctgaggtt     240
tccacctatt tgccaaaggg tgacatgtgg tccgtgcaca agttcggggg aacttgcatg     300
ggcaccccgc aacgcatcca gaacgtggcc gacattgtcc tcggcgatag ctctgaaagg     360
aagctcatta tcgtctcagc tatgtccaag gtgacggaca tgatgtttaa cctcgttcat     420
aaggcccaat cgcgggataa ctcctatgtc acagcactgg acgaggtgtt caacaagcac     480
atggccgccg caaaggaact cctcgatggg gaagacctcg ccagattcct cgctcagttg     540
cactccgaca tctcgaacct ccgggccatg ttgagggcta tcttcattgc cggacatgcc     600
```

-continued

| | |
|---|---|
| accgagtctt tttccgattt cgtggtgggg catggcgagc tctggtcagc gcagatgctc | 660 |
| tcctacgcta ttaagaagtc gggcgtcccc tgcagctgga tggacacgag ggaggtgctg | 720 |
| gtggtgaagc catctggaag taatcaggtg acccagatt acctggagtc agagaagcgg | 780 |
| ctgcagaagt ggttttcacg ccagcctgcc gagatcatca tcgctactgg ctttatcgcg | 840 |
| tcgaccgctg aaaacattcc aacgaccctg aagcgcgacg ggtctgactt cagtgcatcc | 900 |
| atcatcggct cacttgttcg ggcctgtcag gttacaatct ggaccgacgt ggatggcgtc | 960 |
| ttctcggcag acccacggaa ggtcagtgag gctgttatct tgagcacgct ctcctaccaa | 1020 |
| gaagcatggg aaatgtccta ctttggtgcc aacgtgctcc atccccggac catcatccca | 1080 |
| gttatgaagg acaacatccc cattgtcatc aggaacatgt tcaatctttc ggcaccgggc | 1140 |
| accaccattt gcaagcaacc agcaaacgag aatgctgatc tcgacgcctg tgttaagtct | 1200 |
| ttcgctacaa tcgataagct tgcactggtg aatgtcgagg caccggcat ggccggggtc | 1260 |
| cctggcaccg ccagcgccat cttctctgca gctaaggatg tcggagccaa cgtgattatg | 1320 |
| atttctcaag ccagttcgga gcactccgtt tgctttgcgg tgccagagaa ggaggttgcg | 1380 |
| gctgtcagca ccgccttgca cgtcaggttc cgggaggccc tcgcggccgg tagactgtcc | 1440 |
| aaggtcgagg tcattcgggg ctgctcgatc ctcgccgccg tcgggctgag gatggcttct | 1500 |
| accccaggcg tctcggcgat cctgttcgat gccttggcaa aggctaatat caacgtgcgg | 1560 |
| gcgatcgcgc aaggctgctc cgagtacaat atcaccgtgg tgctcaagca agaggactgt | 1620 |
| gttcgcgccc tccgggctgt tcactcaaga ttctttctca gtaagacgac cctggccgtg | 1680 |
| ggcatcatcg gccccgggct cattgggga accctcctgg atcaactgaa ggaccaggcc | 1740 |
| gccgtgctta aggagaacat gaatatcgat ctgcgcgtga tcggcatctc tggatcccgc | 1800 |
| acgatgcacc tctcggacat cggagtcgac ctcaatcagt ggaaggagct gctcagaaag | 1860 |
| gaagccgagc cggccgatct ggactcgttt gtgcgtcatc tgtccgagaa ccacgtgttc | 1920 |
| ccaaataagg tgctcgtgga ctgcactgcc gataacctacg tggcatgcca ctactatgac | 1980 |
| tggctgaaga agggcatcca cgttatcacc cccaacaaga aggctaactc cggcccactt | 2040 |
| gatcgctacc tcaagctccg tactcttcaa agggcttctt acacacacta cttctacgag | 2100 |
| gcgaccgtgg gagccgggct ccctatcatc tccaccctcc gcggcctgct ggagactggg | 2160 |
| gacaagatcc tgcggattga gggtatcttt tccggtaccc tctcctacat ttttaacaac | 2220 |
| ttcgagggca cccggacatt ctctaacgtg gtggccgagg cgaaggaggc tggctacacc | 2280 |
| gagccagacc cacgcgacga cttgtcgggt acagatgtgg cgcgtaaggt tatcatcttg | 2340 |
| gcgcgcgagt ctggtcttcg cctcgagctc tcggatattc ctgttaagag ccttgtccca | 2400 |
| gaggccctga ggagttgcag ttccgccgac gaattcatgc agaagttgcc gtcttttgac | 2460 |
| caagactggg accgcagag ggatgaagcc gaggccgccg gagaggtgct ccgctacgtc | 2520 |
| ggcgtggtgg acgtcgccaa caggaagggc cgtgttgaac ttcaacggta caagcgcgat | 2580 |
| catccatttg cgcaactttc gggtagcgat aatatcatcg cctttaccac ctcgagatac | 2640 |
| aaggagcaac ccttgatcgt tagaggacca ggagctggtg ccgaagttac cgcggggga | 2700 |
| gtcttctgcg acattctgcg cctcgcgtcg tatctgggcg caccgagtta a | 2751 |

<210> SEQ ID NO 2
<211> LENGTH: 916
<212> TYPE: PRT
<213> ORGANISM: Oryza sativa

<400> SEQUENCE: 2

```
Met Ala Arg Ser Leu Ala Val Ala Ser Pro Leu Pro Ala Ala Ala
1               5                   10                  15

Val Arg Arg Arg Pro Arg Ala Ser Ala Ser Gly Arg Glu Val Ile Ser
            20                  25                  30

Gln Cys Trp Lys Cys Glu Ile Asn Gln Asp Gln Pro Leu Gly Asn Ser
            35                  40                  45

Leu Arg Ile Gly His Ser Gln Gly Ser Leu Gln Arg His Gly Ser Arg
    50                  55                  60

Asn Leu Leu Ala Ala Ala Ala Ile Ser Ile Glu Gln Ala Glu Val
65                  70                  75                  80

Ser Thr Tyr Leu Pro Lys Gly Asp Met Trp Ser Val His Lys Phe Gly
                85                  90                  95

Gly Thr Cys Met Gly Thr Pro Gln Arg Ile Gln Asn Val Ala Asp Ile
                100                 105                 110

Val Leu Gly Asp Ser Ser Glu Arg Lys Leu Ile Ile Val Ser Ala Met
            115                 120                 125

Ser Lys Val Thr Asp Met Met Phe Asn Leu Val His Lys Ala Gln Ser
130                 135                 140

Arg Asp Asn Ser Tyr Val Thr Ala Leu Asp Glu Val Phe Asn Lys His
145                 150                 155                 160

Met Ala Ala Ala Lys Glu Leu Leu Asp Gly Glu Asp Leu Ala Arg Phe
                165                 170                 175

Leu Ala Gln Leu His Ser Asp Ile Ser Asn Leu Arg Ala Met Leu Arg
            180                 185                 190

Ala Ile Phe Ile Ala Gly His Ala Thr Glu Ser Phe Ser Asp Phe Val
    195                 200                 205

Val Gly His Gly Glu Leu Trp Ser Ala Gln Met Leu Ser Tyr Ala Ile
210                 215                 220

Lys Lys Ser Gly Val Pro Cys Ser Trp Met Asp Thr Arg Glu Val Leu
225                 230                 235                 240

Val Val Lys Pro Ser Gly Ser Asn Gln Val Asp Pro Asp Tyr Leu Glu
                245                 250                 255

Ser Glu Lys Arg Leu Gln Lys Trp Phe Ser Arg Gln Pro Ala Glu Ile
            260                 265                 270

Ile Ile Ala Thr Gly Phe Ile Ala Ser Thr Ala Glu Asn Ile Pro Thr
    275                 280                 285

Thr Leu Lys Arg Asp Gly Ser Asp Phe Ser Ala Ser Ile Ile Gly Ser
290                 295                 300

Leu Val Arg Ala Cys Gln Val Thr Ile Trp Thr Asp Val Asp Gly Val
305                 310                 315                 320

Phe Ser Ala Asp Pro Arg Lys Val Ser Glu Ala Val Ile Leu Ser Thr
                325                 330                 335

Leu Ser Tyr Gln Glu Ala Trp Glu Met Ser Tyr Phe Gly Ala Asn Val
            340                 345                 350

Leu His Pro Arg Thr Ile Ile Pro Val Met Lys Asp Asn Ile Pro Ile
    355                 360                 365

Val Ile Arg Asn Met Phe Asn Leu Ser Ala Pro Gly Thr Thr Ile Cys
370                 375                 380

Lys Gln Pro Ala Asn Glu Asn Ala Asp Leu Asp Ala Cys Val Lys Ser
385                 390                 395                 400

Phe Ala Thr Ile Asp Lys Leu Ala Leu Val Asn Val Glu Gly Thr Gly
                405                 410                 415
```

```
Met Ala Gly Val Pro Gly Thr Ala Ser Ala Ile Phe Ser Ala Ala Lys
            420                 425                 430

Asp Val Gly Ala Asn Val Ile Met Ile Ser Gln Ala Ser Ser Glu His
            435                 440                 445

Ser Val Cys Phe Ala Val Pro Glu Lys Glu Val Ala Ala Val Ser Thr
            450                 455                 460

Ala Leu His Val Arg Phe Arg Glu Ala Leu Ala Ala Gly Arg Leu Ser
465                 470                 475                 480

Lys Val Glu Val Ile Arg Gly Cys Ser Ile Leu Ala Ala Val Gly Leu
                485                 490                 495

Arg Met Ala Ser Thr Pro Gly Val Ser Ala Ile Leu Phe Asp Ala Leu
            500                 505                 510

Ala Lys Ala Asn Ile Asn Val Arg Ala Ile Ala Gln Gly Cys Ser Glu
            515                 520                 525

Tyr Asn Ile Thr Val Val Leu Lys Gln Glu Asp Cys Val Arg Ala Leu
            530                 535                 540

Arg Ala Val His Ser Arg Phe Phe Leu Ser Lys Thr Thr Leu Ala Val
545                 550                 555                 560

Gly Ile Ile Gly Pro Gly Leu Ile Gly Gly Thr Leu Leu Asp Gln Leu
                565                 570                 575

Lys Asp Gln Ala Ala Val Leu Lys Glu Asn Met Asn Ile Asp Leu Arg
            580                 585                 590

Val Ile Gly Ile Ser Gly Ser Arg Thr Met His Leu Ser Asp Ile Gly
            595                 600                 605

Val Asp Leu Asn Gln Trp Lys Glu Leu Leu Arg Lys Glu Ala Glu Pro
            610                 615                 620

Ala Asp Leu Asp Ser Phe Val Arg His Leu Ser Glu Asn His Val Phe
625                 630                 635                 640

Pro Asn Lys Val Leu Val Asp Cys Thr Ala Asp Thr Tyr Val Ala Cys
                645                 650                 655

His Tyr Tyr Asp Trp Leu Lys Lys Gly Ile His Val Ile Thr Pro Asn
            660                 665                 670

Lys Lys Ala Asn Ser Gly Pro Leu Asp Arg Tyr Leu Lys Leu Arg Thr
            675                 680                 685

Leu Gln Arg Ala Ser Tyr Thr His Tyr Phe Tyr Glu Ala Thr Val Gly
            690                 695                 700

Ala Gly Leu Pro Ile Ile Ser Thr Leu Arg Gly Leu Leu Glu Thr Gly
705                 710                 715                 720

Asp Lys Ile Leu Arg Ile Glu Gly Ile Phe Ser Gly Thr Leu Ser Tyr
                725                 730                 735

Ile Phe Asn Asn Phe Glu Gly Thr Arg Thr Phe Ser Asn Val Val Ala
            740                 745                 750

Glu Ala Lys Glu Ala Gly Tyr Thr Glu Pro Asp Pro Arg Asp Asp Leu
            755                 760                 765

Ser Gly Thr Asp Val Ala Arg Lys Val Ile Ile Leu Ala Arg Glu Ser
            770                 775                 780

Gly Leu Arg Leu Glu Leu Ser Asp Ile Pro Val Lys Ser Leu Val Pro
785                 790                 795                 800

Glu Ala Leu Arg Ser Cys Ser Ser Ala Asp Glu Phe Met Gln Lys Leu
                805                 810                 815

Pro Ser Phe Asp Gln Asp Trp Asp Arg Gln Arg Asp Glu Ala Glu Ala
            820                 825                 830
```

```
Ala Gly Glu Val Leu Arg Tyr Val Gly Val Val Asp Val Ala Asn Arg
            835                 840                 845

Lys Gly Arg Val Glu Leu Gln Arg Tyr Lys Arg Asp His Pro Phe Ala
    850                 855                 860

Gln Leu Ser Gly Ser Asp Asn Ile Ile Ala Phe Thr Thr Ser Arg Tyr
865                 870                 875                 880

Lys Glu Gln Pro Leu Ile Val Arg Gly Pro Ala Gly Ala Glu Val
                885                 890                 895

Thr Ala Gly Gly Val Phe Cys Asp Ile Leu Arg Leu Ala Ser Tyr Leu
            900                 905                 910

Gly Ala Pro Ser
            915

<210> SEQ ID NO 3
<211> LENGTH: 833
<212> TYPE: DNA
<213> ORGANISM: Oryza sativa

<400> SEQUENCE: 3
tcgaggtcat tcatatgctt gagaagagag tcgggatagt ccaaaataaa acaaaggtaa      60
gattacctgg tcaaaagtga aaacatcagt taaaaggtgg tataagtaaa atatcggtaa    120
taaaaggtgg cccaaagtga aatttactct tttctactat tataaaaatt gaggatgttt    180
tgtcggtact tgatacgtc attttttgtat gaattggttt ttaagtttat tcgcgatttg    240
gaaatgcata tctgtatttg agtcggtttt taagttcgtt gcttttgtaa atacagaggg    300
atttgtataa gaaatatctt taaaaaaccc atatgctaat ttgacataat ttttgagaaa    360
aatatatatt caggcgaatt ccacaatgaa caataataag attaaaatag cttgcccccg    420
ttgcagcgat gggtattttt tctagtaaaa taaagataaa acttagactc aaaacattta    480
caaaaacaac ccctaaagtc ctaaagccca aagtgctatg cacgatccat agcaagccca    540 gcccaacccca acccaaccca acccaccca gtgcagccaa ctggcaaata gtctccaccc    600
ccggcactat caccgtgagt tgtccgcacc accgcacgtc tcgcagccaa aaaaaaaaaa    660
agaaagaaaa aaaagaaaaa gaaaacagc aggtgggtcc gggtcgtggg ggccggaaaa    720
gcgaggagga tcgcgagcag cgacgaggcc cggccctccc tccgcttcca agaaacgcc    780 ccccatcgcc actatataca tacccccccc tctcctccca tcccccaac cct           833

<210> SEQ ID NO 4
<211> LENGTH: 462
<212> TYPE: DNA
<213> ORGANISM: Oryza sativa

<400> SEQUENCE: 4
gtaaccaccc cgcccctctc ctctttcttt ctccgttttt ttttttccgtc tcggtctcga     60 tctttggcct tggtagtttg ggtgggcgag aggcggcttc gtgcgcgccc agatcggtgc    120
gcgggagggg cggatctcg cggctggggc tctcgccggc gtggatccgg cccggatctc    180
gcggggaatg gggctctcgg atgtagatct gcgatccgcc gttgttgggg gagatgatgg    240
ggggtttaaa atttccgcca tgctaaacaa gatcaggaag aggggaaaag ggcactatgg    300
tttatatttt tatataattc tgctgcttcg tcaggcttag atgtgctaga tctttctttc    360 ttcttttttgt gggtagaatt tgaatccctc agcattgttc atcggtagtt tttcttttca    420
tgatttgtga caaatgcagc ctcgtgcgga gcttttttgt ag                      462
```

```
<210> SEQ ID NO 5
<211> LENGTH: 250
<212> TYPE: DNA
<213> ORGANISM: Artificial
<220> FEATURE:
<223> OTHER INFORMATION: Nos terminator

<400> SEQUENCE: 5
gatcgttcaa acatttggca ataaagtttc ttaagattga atcctgttgc cggtcttgcg      60
atgattatca tataatttct gttgaattac gttaagcatg taataattaa catgtaatgc     120
atgacgttat ttatgagatg ggttttatg attagagtcc cgcaattata catttaatac      180
gcgatagaaa acaaaatata gcgcgcaaac taggataaat tatcgcgcgc ggtgtcatct     240
atgttactag                                                            250

<210> SEQ ID NO 6
<211> LENGTH: 21
<212> TYPE: DNA
<213> ORGANISM: Artificial
<220> FEATURE:
<223> OTHER INFORMATION: Primer

<400> SEQUENCE: 6
gatgtgcgtg tcatcggaat a                                                21

<210> SEQ ID NO 7
<211> LENGTH: 20
<212> TYPE: DNA
<213> ORGANISM: Artificial
<220> FEATURE:
<223> OTHER INFORMATION: Primer

<400> SEQUENCE: 7
catcacttct gcttgtcggc                                                  20

<210> SEQ ID NO 8
<211> LENGTH: 4505
<212> TYPE: DNA
<213> ORGANISM: Artificial
<220> FEATURE:
<223> OTHER INFORMATION: Full construct

<400> SEQUENCE: 8
tcgaggtcat tcatatgctt gagaagagag tcgggatagt ccaaaataaa acaaaggtaa      60
gattacctgg tcaaaagtga aaacatcagt taaaggtgg tataagtaaa atatcggtaa      120
taaaaggtgg cccaaagtga aatttactct tttctactat tataaaaatt gaggatgttt    180
tgtcggtact tgatacgtc attttgtat gaattggttt ttaagtttat tcgcgatttg      240
gaaatgcata tctgtatttg agtcggtttt taagttcgtt gcttttgtaa atacagaggg    300
atttgtataa gaaatatctt taaaaaaccc atatgctaat ttgacataat ttttgagaaa    360
aatatatatt caggcgaatt ccacaatgaa caataataag attaaaatag cttgcccccg    420
ttgcagcgat gggtattttt tctagtaaaa taaagataa acttagactc aaaacattta    480
caaaaacaac ccctaaagtc ctaaagccca aagtgctatg cacgatccat agcaagccca    540
gcccaaccca acccaaccca acccacccca gtgcagccaa ctggcaaata gtctccaccc    600
ccggcactat caccgtgagt tgtccgcacc accgcacgtc tcgcagccaa aaaaaaaaa    660 agaaagaaaa aaaagaaaaa gaaaacagc aggtgggtcc gggtcgtggg ggccggaaaa    720
gcgaggagga tcgcgagcag cgacgaggcc cggccctccc tccgcttcca agaaacgcc    780
```

```
ccccatcgcc actatataca tacccccccc tctcctccca tcccccaac cctaccacca    840
ccaccaccac cacctcctcc ccctcgctg ccggacgacg agctcctccc ccctcccct     900
ccgccgccgc cgcgccggta accaccccgc ccctctcctc tttctttctc cgttttttt    960
ttccgtctcg gtctcgatct ttggccttgg tagtttgggt gggcgagagg cggcttcgtg   1020
cgcgcccaga tcggtgcgcg ggaggggcgg gatctcgcgg ctggggctct cgccggcgtg   1080
gatccggccc ggatctcgcg gggaatgggg ctctcggatg tagatctgcg atccgccgtt   1140
gttgggggag atgatggggg gtttaaaatt tccgccatgc taaacaagat caggaagagg   1200
ggaaaagggc actatggttt atattttat atatttctgc tgcttcgtca ggcttagatg    1260
tgctagatct ttctttcttc tttttgtggg tagaatttga atccctcagc attgttcatc   1320
ggtagttttt cttttcatga tttgtgacaa atgcagcctc gtgcggagct tttttgtagg   1380
tagacgataa gcttgatatc acaagtttgt acaaaaaagc aggctccacc atggctcgta   1440
gtctcgctgt cgccagccca ctcccaccgg cggcagcggt caggcgccgt ccacgggcat   1500
cggcctccgg acggaggtc atcagccagt gctggaagtg cgagatcaac caggatcaac    1560
cacttggcaa tagcctcaga attgggcact ctcaagggtc actccaacgc cacggcagta   1620
ggaacttgct cgcggccgcg gccgctatct ccattgagca agctgaggtt ccacctatt    1680
tgccaagggg tgacatgtgg tccgtgcaca agttcggggg aacttgcatg ggcaccccgc   1740
aacgcatcca gaacgtggcc gacattgtcc tcggcgatag ctctgaaagg aagctcatta   1800
tcgtctcagc tatgtccaag gtgacggaca tgatgtttaa cctcgttcat aaggcccaat   1860
cgcgggataa ctcctatgtc acagcactgg acgaggtgtt caacaagcac atggccgccg   1920
caaaggaact cctcgatggg gaagacctcg ccagattcct cgctcagttg cactccgaca   1980
tctcgaacct ccgggccatg ttgagggcta tcttcattgc cggacatgcc accgagtctt   2040
tttccgattt cgtggtgggg catggcgagc tctggtcagc gcagatgctc tcctacgcta   2100
ttaagaagtc gggcgtcccc tgcagctgga tggacacgag ggaggtgctg gtggtgaagc   2160
catctggaag taatcaggtg gacccagatt acctggagtc agagaagcgg ctgcagaagt   2220
ggttttcacg ccagcctgcc gagatcatca tcgctactgg ctttatcgcg tcgaccgctg   2280
aaaacattcc aacgaccctg aagcgcgacg ggtctgactt cagtgcatcc atcatcggct   2340
cacttgttcg ggcctgtcag gttacaatct ggaccgacgt ggatggcgtc ttctcggcag   2400
acccacggaa ggtcagtgag gctgttatct tgagcacgct ctcctaccaa gaagcatggg   2460
aaatgtccta ctttggtgcc aacgtgctcc atccccggac catcatccca gttatgaagg   2520
acaacatccc cattgtcatc aggaacatgt tcaatctttc ggcaccgggc accaccattt   2580
gcaagcaacc agcaaacgag aatgctgatc tcgacgcctg tgttaagtct ttcgctacaa   2640
tcgataagct tgcactggtg aatgtcgagg gcaccggcat ggccggggtc cctggcaccg   2700
ccagcgccat cttctctgca gctaaggatg tcggagccaa cgtgattatg atttctcaag   2760
ccagttcgga gcactccgtt tgctttgcgg tgccagagaa ggaggttgcg gctgtcagca   2820
ccgccttgca cgtcaggttc cgggaggccc tcgcggccgg tagactgtcc aaggtcgagg   2880
tcattcgggg ctgctcgatc ctcgccgccg tcgggctgag gatggcttct accccaggcg   2940
tctcggcgat cctgttcgat gccttggcaa aggctaatat caacgtgcgg gcgatcgcgc   3000
aaggctgctc cgagtacaat atcaccgtgg tgctcaagca agaggactgt gttcgcgccc   3060
tccgggctgt tcactcaaga ttcttttctca gtaagacgac cctggccgtg gcatcatcg   3120
gccccgggct cattgggga accctcctgg atcaactgaa ggaccaggcc gccgtgctta   3180
```

```
aggagaacat gaatatcgat ctgcgcgtga tcggcatctc tggatcccgc acgatgcacc    3240
tctcggacat cggagtcgac ctcaatcagt ggaaggagct gctcagaaag gaagccgagc    3300
cggccgatct ggactcgttt gtgcgtcatc tgtccgagaa ccacgtgttc ccaaataagg    3360
tgctcgtgga ctgcactgcc gataccacg tggcatgcca ctactatgac tggctgaaga     3420
agggcatcca cgttatcacc cccaacaaga aggctaactc cggcccactt gatcgctacc    3480
tcaagctccg tactcttcaa agggcttctt acacacacta cttctacgag gcgaccgtgg    3540
gagccgggct ccctatcatc tccaccctcc gcggcctgct ggagactggg gacaagatcc    3600
tgcggattga gggtatcttt tccggtaccc tctcctacat ttttaacaac ttcgagggca    3660
cccggacatt ctctaacgtg gtggccgagg cgaaggaggc tggctacacc gagccagacc    3720
cacgcgacga cttgtcgggt acagatgtgg cgcgtaaggt tatcatcttg gcgcgcgagt    3780
ctggtcttcg cctcgagctc tcggatattc ctgttaagag ccttgtccca gaggccctga    3840
ggagttgcag ttccgccgac gaattcatgc agaagttgcc gtcttttgac caagactggg    3900
accgccagag ggatgaagcc gaggccgccg agaggtgct ccgctacgtc ggcgtggtgg      3960
acgtcgccaa caggaagggc cgtgttgaac ttcaacggta caagcgcgat catccatttg    4020
cgcaactttc gggtagcgat aatatcatcg cctttaccac ctcgagatac aaggagcaac    4080
ccttgatcgt tagaggacca ggagctggtg ccgaagttac cgcggggga gtcttctgcg      4140 acattctgcg cctcgcgtcg tatctgggcg caccgagtta atctagaccc agctttcttg    4200
tacaaagtgg tgatatcgaa ttcctgcagc ccggggatc cgaatttcac ccgatcgttc      4260
aaacatttgg caataaagtt tcttaagatt gaatcctgtt gccggtcttg cgatgattat    4320
catataattt ctgttgaatt acgttaagca tgtaataatt aacatgtaat gcatgacgtt    4380
atttatgaga tgggttttta tgattagagt cccgcaatta tacatttaat acgcgataga    4440
aaacaaaata tagcgcgcaa actaggataa attatcgcgc gcggtgtcat ctatgttact    4500
agatc                                                                4505
```

<210> SEQ ID NO 9
<211> LENGTH: 916
<212> TYPE: PRT
<213> ORGANISM: Glycine max

<400> SEQUENCE: 9

```
Met Ala Ser Phe Ser Ala Ala Val Ala Gln Phe Ser Arg Val Ser Pro
1               5                   10                  15

Ser His Thr Ser Leu His Ser His Ser His Gly Thr Leu Phe Gln Ser
            20                  25                  30

Gln Cys Arg Pro Phe Phe Leu Ser Arg Thr Ser His Ser Leu Arg Lys
        35                  40                  45

Gly Leu Thr Leu Pro Arg Gly Arg Glu Ala Pro Ser Thr Ser Val Arg
    50                  55                  60

Ala Ser Phe Thr Asp Val Ser Pro Asn Val Ser Leu Glu Glu Lys Gln
65                  70                  75                  80

Leu Pro Lys Gly Glu Thr Trp Ser Val His Lys Phe Gly Gly Thr Cys
                85                  90                  95

Val Gly Thr Ser Gln Arg Ile Lys Asn Val Ala Asp Ile Ile Leu Lys
            100                 105                 110

Asp Asp Ser Glu Arg Lys Leu Val Val Val Ser Ala Met Ser Lys Val
        115                 120                 125
```

-continued

```
Thr Asp Met Met Tyr Asp Leu Ile His Lys Ala Gln Ser Arg Asp Glu
    130                 135                 140

Ser Tyr Thr Ala Ala Leu Asn Ala Val Leu Glu Lys His Ser Ala Thr
145                 150                 155                 160

Ala His Asp Ile Leu Asp Gly Asp Asn Leu Ala Thr Phe Leu Ser Lys
                165                 170                 175

Leu His His Asp Ile Ser Asn Leu Lys Ala Met Leu Arg Ala Ile Tyr
            180                 185                 190

Ile Ala Gly His Ala Thr Glu Ser Phe Thr Asp Phe Val Val Gly His
                195                 200                 205

Gly Glu Leu Trp Ser Ala Gln Met Leu Ser Leu Val Ile Arg Lys Asn
    210                 215                 220

Gly Thr Asp Cys Lys Trp Met Asp Thr Arg Asp Val Leu Ile Val Asn
225                 230                 235                 240

Pro Thr Gly Ser Asn Gln Val Asp Pro Asp Tyr Leu Glu Ser Glu Gln
                245                 250                 255

Arg Leu Glu Lys Trp Tyr Ser Leu Asn Pro Cys Lys Val Ile Ile Ala
            260                 265                 270

Thr Gly Phe Ile Ala Ser Thr Pro Gln Asn Ile Pro Thr Thr Leu Lys
                275                 280                 285

Arg Asp Gly Ser Asp Phe Ser Ala Ala Ile Met Gly Ala Leu Phe Lys
    290                 295                 300

Ala Arg Gln Val Thr Ile Trp Thr Asp Val Asp Gly Val Tyr Ser Ala
305                 310                 315                 320

Asp Pro Arg Lys Val Ser Glu Ala Val Ile Leu Lys Thr Leu Ser Tyr
                325                 330                 335

Gln Glu Ala Trp Glu Met Ser Tyr Phe Gly Ala Asn Val Leu His Pro
            340                 345                 350

Arg Thr Ile Ile Pro Val Met Arg Tyr Gly Ile Pro Ile Met Ile Arg
                355                 360                 365

Asn Ile Phe Asn Leu Ser Ala Pro Gly Thr Lys Ile Cys His Pro Ser
    370                 375                 380

Val Asn Asp His Glu Asp Ser Gln Asn Leu Gln Asn Phe Val Lys Gly
385                 390                 395                 400

Phe Ala Thr Ile Asp Asn Leu Ala Leu Val Asn Val Glu Gly Thr Gly
                405                 410                 415

Met Ala Gly Val Pro Gly Thr Ala Ser Ala Ile Phe Gly Ala Val Lys
            420                 425                 430

Asp Val Gly Ala Asn Val Ile Met Ile Ser Gln Ala Ser Ser Glu His
                435                 440                 445

Ser Val Cys Phe Ala Val Pro Glu Lys Glu Val Lys Ala Val Ala Glu
    450                 455                 460

Ala Leu Gln Ser Arg Phe Arg Gln Ala Leu Asp Asn Gly Arg Leu Ser
465                 470                 475                 480

Gln Val Ala Val Ile Pro Asn Cys Ser Ile Leu Ala Ala Val Gly Gln
                485                 490                 495

Lys Met Ala Ser Thr Pro Gly Val Ser Ala Ser Leu Phe Asn Ala Leu
            500                 505                 510

Ala Lys Ala Asn Ile Asn Val Arg Ala Ile Ala Gln Gly Cys Ser Glu
                515                 520                 525

Tyr Asn Ile Thr Val Val Val Lys Arg Glu Asp Cys Ile Lys Ala Leu
    530                 535                 540
```

```
Arg Ala Val His Ser Arg Phe Tyr Leu Ser Arg Thr Thr Ile Ala Met
545                 550                 555                 560

Gly Ile Ile Gly Pro Gly Leu Ile Gly Ser Thr Leu Leu Glu Gln Leu
            565                 570                 575

Arg Asp Gln Ala Ser Thr Leu Lys Glu Glu Phe Asn Ile Asp Leu Arg
                580                 585                 590

Val Met Gly Ile Leu Gly Ser Lys Ser Met Leu Leu Ser Asp Val Gly
        595                 600                 605

Ile Asp Leu Ala Arg Trp Arg Glu Leu Arg Glu Arg Gly Glu Val
    610                 615                 620

Ala Asn Met Glu Lys Phe Val Gln His Val His Gly Asn His Phe Ile
625                 630                 635                 640

Pro Asn Thr Ala Leu Val Asp Cys Thr Ala Asp Ser Val Ile Ala Gly
                645                 650                 655

Tyr Tyr Tyr Asp Trp Leu Arg Lys Gly Ile His Val Val Thr Pro Asn
                660                 665                 670

Lys Lys Ala Asn Ser Gly Pro Leu Asp Gln Tyr Leu Lys Leu Arg Ala
                675                 680                 685

Leu Gln Arg Gln Ser Tyr Thr His Tyr Phe Tyr Glu Ala Thr Val Gly
690                 695                 700

Ala Gly Leu Pro Ile Val Ser Thr Leu Arg Gly Leu Leu Glu Thr Gly
705                 710                 715                 720

Asp Lys Ile Leu Gln Ile Glu Gly Ile Phe Ser Gly Thr Leu Ser Tyr
                725                 730                 735

Ile Phe Asn Asn Phe Lys Asp Gly Arg Ala Phe Ser Glu Val Val Ser
                740                 745                 750

Glu Ala Lys Glu Ala Gly Tyr Thr Glu Pro Asp Pro Arg Asp Asp Leu
                755                 760                 765

Ser Gly Thr Asp Val Ala Arg Lys Val Ile Ile Leu Ala Arg Glu Ser
        770                 775                 780

Gly Leu Lys Leu Glu Leu Ser Asn Ile Pro Val Glu Ser Pro Val Pro
785                 790                 795                 800

Glu Pro Leu Arg Ala Cys Ala Ser Ala Gln Glu Phe Met Gln Glu Leu
                805                 810                 815

Pro Lys Phe Asp Gln Glu Phe Thr Lys Lys Gln Glu Asp Ala Glu Asn
                820                 825                 830

Ala Gly Glu Val Leu Arg Tyr Val Gly Val Val Asp Val Thr Asn Lys
                835                 840                 845

Lys Gly Val Val Glu Leu Arg Arg Tyr Lys Lys Asp His Pro Phe Ala
850                 855                 860

Gln Leu Ser Gly Ser Asp Asn Ile Ile Ala Phe Thr Thr Arg Arg Tyr
865                 870                 875                 880

Lys Asp Gln Pro Leu Ile Val Arg Gly Pro Gly Ala Gly Ala Gln Val
                885                 890                 895

Thr Ala Gly Gly Ile Phe Ser Asp Ile Leu Arg Leu Ala Ser Tyr Leu
            900                 905                 910

Gly Ala Pro Ser
        915

<210> SEQ ID NO 10
<211> LENGTH: 820
<212> TYPE: PRT
<213> ORGANISM: Escherichia coli

<400> SEQUENCE: 10
```

```
Met Arg Val Leu Lys Phe Gly Gly Thr Ser Val Ala Asn Ala Glu Arg
1               5                   10                  15

Phe Leu Arg Val Ala Asp Ile Leu Glu Ser Asn Ala Arg Gln Gly Gln
            20                  25                  30

Val Ala Thr Val Leu Ser Ala Pro Ala Lys Ile Thr Asn His Leu Val
        35                  40                  45

Ala Met Ile Glu Lys Thr Ile Ser Gly Gln Asp Ala Leu Pro Asn Ile
    50                  55                  60

Ser Asp Ala Glu Arg Ile Phe Ala Glu Leu Leu Thr Gly Leu Ala Ala
65                  70                  75                  80

Ala Gln Pro Gly Phe Pro Leu Ala Gln Leu Lys Thr Phe Val Asp Gln
                85                  90                  95

Glu Phe Ala Gln Ile Lys His Val Leu His Gly Ile Ser Leu Leu Gly
                100                 105                 110

Gln Cys Pro Asp Ser Ile Asn Ala Ala Leu Ile Cys Arg Gly Glu Lys
            115                 120                 125

Met Ser Ile Ala Ile Met Ala Gly Val Leu Glu Ala Arg Gly His Asn
130                 135                 140

Val Thr Val Ile Asp Pro Val Glu Lys Leu Leu Ala Val Gly His Tyr
145                 150                 155                 160

Leu Glu Ser Thr Val Asp Ile Ala Glu Ser Thr Arg Arg Ile Ala Ala
                165                 170                 175

Ser Arg Ile Pro Ala Asp His Met Val Leu Met Ala Gly Phe Thr Ala
            180                 185                 190

Gly Asn Glu Lys Gly Glu Leu Val Val Leu Gly Arg Asn Gly Ser Asp
        195                 200                 205

Tyr Ser Ala Ala Val Leu Ala Ala Cys Leu Arg Ala Asp Cys Cys Glu
    210                 215                 220

Ile Trp Thr Asp Val Asp Gly Val Tyr Thr Cys Asp Pro Arg Gln Val
225                 230                 235                 240

Pro Asp Ala Arg Leu Leu Lys Ser Met Ser Tyr Gln Glu Ala Met Glu
                245                 250                 255

Leu Ser Tyr Phe Gly Ala Lys Val Leu His Pro Arg Thr Ile Thr Pro
            260                 265                 270

Ile Ala Gln Phe Gln Ile Pro Cys Leu Ile Lys Asn Thr Gly Asn Pro
        275                 280                 285

Gln Ala Pro Gly Thr Leu Ile Gly Ala Ser Arg Asp Glu Asp Glu Leu
290                 295                 300

Pro Val Lys Gly Ile Ser Asn Leu Asn Asn Met Ala Met Phe Ser Val
305                 310                 315                 320

Ser Gly Pro Gly Met Lys Gly Met Val Gly Met Ala Ala Arg Val Phe
                325                 330                 335

Ala Ala Met Ser Arg Ala Arg Ile Ser Val Val Leu Ile Thr Gln Ser
            340                 345                 350

Ser Ser Glu Tyr Ser Ile Ser Phe Cys Val Pro Gln Ser Asp Cys Val
        355                 360                 365

Arg Ala Glu Arg Ala Met Gln Glu Glu Phe Tyr Leu Glu Leu Lys Glu
370                 375                 380

Gly Leu Leu Glu Pro Leu Ala Val Thr Glu Arg Leu Ala Ile Ile Ser
385                 390                 395                 400

Val Val Gly Asp Gly Met Arg Thr Leu Arg Gly Ile Ser Ala Lys Phe
                405                 410                 415
```

```
Phe Ala Ala Leu Ala Arg Ala Asn Ile Asn Ile Val Ala Ile Ala Gln
            420                 425                 430
Gly Ser Ser Glu Arg Ser Ile Ser Val Val Asn Asn Asp Asp Ala
        435                 440                 445
Thr Thr Gly Val Arg Val Thr His Gln Met Leu Phe Asn Thr Asp Gln
    450                 455                 460
Val Ile Glu Val Phe Val Ile Gly Val Gly Gly Val Gly Gly Ala Leu
465                 470                 475                 480
Leu Glu Gln Leu Lys Arg Gln Gln Ser Trp Leu Lys Asn Lys His Ile
            485                 490                 495
Asp Leu Arg Val Cys Gly Val Ala Asn Ser Lys Ala Leu Leu Thr Asn
            500                 505                 510
Val His Gly Leu Asn Leu Glu Asn Trp Gln Lys Glu Leu Ala Gln Ala
            515                 520                 525
Lys Glu Pro Phe Asn Leu Gly Arg Leu Ile Arg Leu Val Lys Glu Tyr
            530                 535                 540
His Leu Leu Asn Pro Val Ile Val Asp Cys Thr Ser Ser Gln Ala Val
545                 550                 555                 560
Ala Asp Gln Tyr Ala Asp Phe Leu Arg Glu Gly Phe His Val Val Thr
                565                 570                 575
Pro Asn Lys Lys Ala Asn Thr Ser Ser Met Asp Tyr Tyr His Gln Leu
            580                 585                 590
Arg Tyr Ala Ala Glu Lys Ser Arg Arg Lys Phe Leu Tyr Asp Thr Asn
            595                 600                 605
Val Gly Ala Gly Leu Pro Val Ile Glu Asn Leu Gln Asn Leu Leu Asn
            610                 615                 620
Ala Gly Asp Glu Leu Met Lys Phe Ser Gly Ile Leu Ser Gly Ser Leu
625                 630                 635                 640
Ser Tyr Ile Phe Gly Lys Leu Asp Glu Gly Met Ser Phe Ser Glu Ala
                645                 650                 655
Thr Thr Leu Ala Arg Glu Met Gly Tyr Thr Glu Pro Asp Pro Arg Asp
            660                 665                 670
Asp Leu Ser Gly Met Asp Val Ala Arg Lys Leu Leu Ile Leu Ala Arg
            675                 680                 685
Glu Thr Gly Arg Glu Leu Glu Leu Ala Asp Ile Glu Ile Glu Pro Val
690                 695                 700
Leu Pro Ala Glu Phe Asn Ala Glu Gly Asp Val Ala Ala Phe Met Ala
705                 710                 715                 720
Asn Leu Ser Gln Leu Asp Asp Leu Phe Ala Ala Arg Val Ala Lys Ala
                725                 730                 735
Arg Asp Glu Gly Lys Val Leu Arg Tyr Val Gly Asn Ile Asp Glu Asp
            740                 745                 750
Gly Val Cys Arg Val Lys Ile Ala Glu Val Asp Gly Asn Asp Pro Leu
            755                 760                 765
Phe Lys Val Lys Asn Gly Glu Asn Ala Leu Ala Phe Tyr Ser His Tyr
            770                 775                 780
Tyr Gln Pro Leu Pro Leu Val Leu Arg Gly Tyr Gly Ala Gly Asn Asp
785                 790                 795                 800
Val Thr Ala Ala Gly Val Phe Ala Asp Leu Leu Arg Thr Leu Ser Trp
                805                 810                 815
Lys Leu Gly Val
            820
```

```
<210> SEQ ID NO 11
<211> LENGTH: 810
<212> TYPE: PRT
<213> ORGANISM: Escherichia coli

<400> SEQUENCE: 11
```

| | | | | | | | | | | | | | | |
|---|---|---|---|---|---|---|---|---|---|---|---|---|---|---|
| Met | Ser | Val | Ile | Ala | Gln | Ala | Gly | Ala | Lys | Gly | Arg | Gln | Leu | His | Lys |
| 1 | | | | 5 | | | | | 10 | | | | | 15 | |

| Phe | Gly | Gly | Ser | Ser | Leu | Ala | Asp | Val | Lys | Cys | Tyr | Leu | Arg | Val | Ala |
|---|---|---|---|---|---|---|---|---|---|---|---|---|---|---|---|
| | | | 20 | | | | | 25 | | | | | 30 | | |

| Gly | Ile | Met | Ala | Glu | Tyr | Ser | Gln | Pro | Asp | Asp | Met | Met | Val | Val | Ser |
|---|---|---|---|---|---|---|---|---|---|---|---|---|---|---|---|
| | | | 35 | | | | | 40 | | | | | 45 | | |

| Ala | Ala | Gly | Ser | Thr | Thr | Asn | Gln | Leu | Ile | Asn | Trp | Leu | Lys | Leu | Ser |
|---|---|---|---|---|---|---|---|---|---|---|---|---|---|---|---|
| | 50 | | | | | 55 | | | | | 60 | | | | |

| Gln | Thr | Asp | Arg | Leu | Ser | Ala | His | Gln | Val | Gln | Gln | Thr | Leu | Arg | Arg |
|---|---|---|---|---|---|---|---|---|---|---|---|---|---|---|---|
| 65 | | | | | 70 | | | | | 75 | | | | | 80 |

| Tyr | Gln | Cys | Asp | Leu | Ile | Ser | Gly | Leu | Leu | Pro | Ala | Glu | Glu | Ala | Asp |
|---|---|---|---|---|---|---|---|---|---|---|---|---|---|---|---|
| | | | | 85 | | | | | 90 | | | | | 95 | |

| Ser | Leu | Ile | Ser | Ala | Phe | Val | Ser | Asp | Leu | Glu | Arg | Leu | Ala | Ala | Leu |
|---|---|---|---|---|---|---|---|---|---|---|---|---|---|---|---|
| | | | 100 | | | | | 105 | | | | | 110 | | |

| Leu | Asp | Ser | Gly | Ile | Asn | Asp | Ala | Val | Tyr | Ala | Glu | Val | Val | Gly | His |
|---|---|---|---|---|---|---|---|---|---|---|---|---|---|---|---|
| | | | 115 | | | | | 120 | | | | | 125 | | |

| Gly | Glu | Val | Trp | Ser | Ala | Arg | Leu | Met | Ser | Ala | Val | Leu | Asn | Gln | Gln |
|---|---|---|---|---|---|---|---|---|---|---|---|---|---|---|---|
| | 130 | | | | | 135 | | | | | 140 | | | | |

| Gly | Leu | Pro | Ala | Ala | Trp | Leu | Asp | Ala | Arg | Glu | Phe | Leu | Arg | Ala | Glu |
|---|---|---|---|---|---|---|---|---|---|---|---|---|---|---|---|
| 145 | | | | | 150 | | | | | 155 | | | | | 160 |

| Arg | Ala | Ala | Gln | Pro | Gln | Val | Asp | Glu | Gly | Leu | Ser | Tyr | Pro | Leu | Leu |
|---|---|---|---|---|---|---|---|---|---|---|---|---|---|---|---|
| | | | | 165 | | | | | 170 | | | | | 175 | |

| Gln | Gln | Leu | Leu | Val | Gln | His | Pro | Gly | Lys | Arg | Leu | Val | Val | Thr | Gly |
|---|---|---|---|---|---|---|---|---|---|---|---|---|---|---|---|
| | | | 180 | | | | | 185 | | | | | 190 | | |

| Phe | Ile | Ser | Arg | Asn | Asn | Ala | Gly | Glu | Thr | Val | Leu | Leu | Gly | Arg | Asn |
|---|---|---|---|---|---|---|---|---|---|---|---|---|---|---|---|
| | | | 195 | | | | | 200 | | | | | 205 | | |

| Gly | Ser | Asp | Tyr | Ser | Ala | Thr | Gln | Ile | Gly | Ala | Leu | Ala | Gly | Val | Ser |
|---|---|---|---|---|---|---|---|---|---|---|---|---|---|---|---|
| | 210 | | | | | 215 | | | | | 220 | | | | |

| Arg | Val | Thr | Ile | Trp | Ser | Asp | Val | Ala | Gly | Val | Tyr | Ser | Ala | Asp | Pro |
|---|---|---|---|---|---|---|---|---|---|---|---|---|---|---|---|
| 225 | | | | | 230 | | | | | 235 | | | | | 240 |

| Arg | Lys | Val | Lys | Asp | Ala | Cys | Leu | Leu | Pro | Leu | Leu | Arg | Leu | Asp | Glu |
|---|---|---|---|---|---|---|---|---|---|---|---|---|---|---|---|
| | | | | 245 | | | | | 250 | | | | | 255 | |

| Ala | Ser | Glu | Leu | Ala | Arg | Leu | Ala | Ala | Pro | Val | Leu | His | Ala | Arg | Thr |
|---|---|---|---|---|---|---|---|---|---|---|---|---|---|---|---|
| | | | 260 | | | | | 265 | | | | | 270 | | |

| Leu | Gln | Pro | Val | Ser | Gly | Ser | Glu | Ile | Asp | Leu | Gln | Leu | Arg | Cys | Ser |
|---|---|---|---|---|---|---|---|---|---|---|---|---|---|---|---|
| | | | 275 | | | | | 280 | | | | | 285 | | |

| Tyr | Thr | Pro | Asp | Gln | Gly | Ser | Thr | Arg | Ile | Glu | Arg | Val | Leu | Ala | Ser |
|---|---|---|---|---|---|---|---|---|---|---|---|---|---|---|---|
| | 290 | | | | | 295 | | | | | 300 | | | | |

| Gly | Thr | Gly | Ala | Arg | Ile | Val | Thr | Ser | His | Asp | Asp | Val | Cys | Leu | Ile |
|---|---|---|---|---|---|---|---|---|---|---|---|---|---|---|---|
| 305 | | | | | 310 | | | | | 315 | | | | | 320 |

| Glu | Phe | Gln | Val | Pro | Thr | Ser | Gln | Asp | Phe | Lys | Leu | Ala | His | Lys | Glu |
|---|---|---|---|---|---|---|---|---|---|---|---|---|---|---|---|
| | | | | 325 | | | | | 330 | | | | | 335 | |

| Ile | Asp | Gln | Ile | Leu | Lys | Arg | Ala | Gln | Val | Arg | Pro | Leu | Ala | Val | Gly |
|---|---|---|---|---|---|---|---|---|---|---|---|---|---|---|---|
| | | | 340 | | | | | 345 | | | | | 350 | | |

| Val | His | Asn | Asp | Arg | Gln | Leu | Leu | Gln | Phe | Cys | Tyr | Thr | Ser | Glu | Val |
|---|---|---|---|---|---|---|---|---|---|---|---|---|---|---|---|
| | | | 355 | | | | | 360 | | | | | 365 | | |

| Ala | Asp | Ser | Ala | Leu | Lys | Ile | Leu | Asp | Glu | Ala | Gly | Leu | Pro | Gly | Glu |
|---|---|---|---|---|---|---|---|---|---|---|---|---|---|---|---|
| | 370 | | | | | 375 | | | | | 380 | | | | |

```
Leu Arg Leu Arg Gln Gly Leu Ala Leu Val Ala Met Val Gly Ala Gly
385                 390                 395                 400

Val Thr Arg Asn Pro Leu His Cys His Arg Phe Trp Gln Gln Leu Lys
            405                 410                 415

Gly Gln Pro Val Glu Phe Thr Trp Gln Ser Asp Asp Gly Ile Ser Leu
            420                 425                 430

Val Ala Val Leu Arg Thr Gly Pro Thr Glu Ser Leu Ile Gln Gly Leu
        435                 440                 445

His Gln Ser Val Phe Arg Ala Glu Lys Arg Ile Gly Leu Val Leu Phe
    450                 455                 460

Gly Lys Gly Asn Ile Gly Ser Arg Trp Leu Glu Leu Phe Ala Arg Glu
465                 470                 475                 480

Gln Ser Thr Leu Ser Ala Arg Thr Gly Phe Glu Phe Val Leu Ala Gly
                485                 490                 495

Val Val Asp Ser Arg Arg Ser Leu Leu Ser Tyr Asp Gly Leu Asp Ala
            500                 505                 510

Ser Arg Ala Leu Ala Phe Phe Asn Asp Glu Ala Val Glu Gln Asp Glu
        515                 520                 525

Glu Ser Leu Phe Leu Trp Met Arg Ala His Pro Tyr Asp Asp Leu Val
530                 535                 540

Val Leu Asp Val Thr Ala Ser Gln Gln Leu Ala Asp Gln Tyr Leu Asp
545                 550                 555                 560

Phe Ala Ser His Gly Phe His Val Ile Ser Ala Asn Lys Leu Ala Gly
                565                 570                 575

Ala Ser Asp Ser Asn Lys Tyr Arg Gln Ile His Asp Ala Phe Glu Lys
            580                 585                 590

Thr Gly Arg His Trp Leu Tyr Asn Ala Thr Val Gly Ala Gly Leu Pro
        595                 600                 605

Ile Asn His Thr Val Arg Asp Leu Ile Asp Ser Gly Asp Thr Ile Leu
    610                 615                 620

Ser Ile Ser Gly Ile Phe Ser Gly Thr Leu Ser Trp Leu Phe Leu Gln
625                 630                 635                 640

Phe Asp Gly Ser Val Pro Phe Thr Glu Leu Val Asp Gln Ala Trp Gln
                645                 650                 655

Gln Gly Leu Thr Glu Pro Asp Pro Arg Asp Asp Leu Ser Gly Lys Asp
            660                 665                 670

Val Met Arg Lys Leu Val Ile Leu Ala Arg Glu Ala Gly Tyr Asn Ile
        675                 680                 685

Glu Pro Asp Gln Val Arg Val Glu Ser Leu Val Pro Ala His Cys Glu
    690                 695                 700

Gly Gly Ser Ile Asp His Phe Phe Glu Asn Gly Asp Glu Leu Asn Glu
705                 710                 715                 720

Gln Met Val Gln Arg Leu Glu Ala Ala Arg Glu Met Gly Leu Val Leu
                725                 730                 735

Arg Tyr Val Ala Arg Phe Asp Ala Asn Gly Lys Ala Val Gly Val
            740                 745                 750

Glu Ala Val Arg Glu Asp His Pro Leu Ala Ser Leu Leu Pro Cys Asp
        755                 760                 765

Asn Val Phe Ala Ile Glu Ser Arg Trp Tyr Arg Asp Asn Pro Leu Val
    770                 775                 780

Ile Arg Gly Pro Gly Ala Gly Arg Asp Val Thr Ala Gly Ala Ile Gln
785                 790                 795                 800

Ser Asp Ile Asn Arg Leu Ala Gln Leu Leu
```

<210> SEQ ID NO 12
<211> LENGTH: 911
<212> TYPE: PRT
<213> ORGANISM: Arabidopsis thaliana

<400> SEQUENCE: 12

```
Met Pro Val Val Ser Leu Ala Lys Val Val Thr Ser Pro Ala Val Ala
1               5                   10                  15

Gly Asp Leu Ala Val Arg Val Pro Phe Ile Tyr Gly Lys Arg Leu Val
            20                  25                  30

Ser Asn Arg Val Ser Phe Gly Lys Leu Arg Arg Arg Ser Cys Ile Gly
        35                  40                  45

Gln Cys Val Arg Ser Glu Leu Gln Ser Pro Arg Val Leu Gly Ser Val
    50                  55                  60

Thr Asp Leu Ala Leu Asp Asn Ser Val Glu Asn Gly His Leu Pro Lys
65                  70                  75                  80

Gly Asp Ser Trp Ala Val His Lys Phe Gly Thr Cys Val Gly Asn
                85                  90                  95

Ser Glu Arg Ile Lys Asp Val Ala Ala Val Val Lys Asp Asp Ser
            100                 105                 110

Glu Arg Lys Leu Val Val Ser Ala Met Ser Lys Val Thr Asp Met
        115                 120                 125

Met Tyr Asp Leu Ile His Arg Ala Glu Ser Arg Asp Asp Ser Tyr Leu
    130                 135                 140

Ser Ala Leu Ser Gly Val Leu Glu Lys His Arg Ala Thr Ala Val Asp
145                 150                 155                 160

Leu Leu Asp Gly Asp Glu Leu Ser Ser Phe Leu Ala Arg Leu Asn Asp
                165                 170                 175

Asp Ile Asn Asn Leu Lys Ala Met Leu Arg Ala Ile Tyr Ile Ala Gly
            180                 185                 190

His Ala Thr Glu Ser Phe Ser Asp Phe Val Val Gly His Gly Glu Leu
        195                 200                 205

Trp Ser Ala Gln Met Leu Ala Ala Val Arg Lys Ser Gly Leu Asp
    210                 215                 220

Cys Thr Trp Met Asp Ala Arg Asp Val Leu Val Ile Pro Thr Ser
225                 230                 235                 240

Ser Asn Gln Val Asp Pro Asp Phe Val Glu Ser Glu Lys Arg Leu Glu
                245                 250                 255

Lys Trp Phe Thr Gln Asn Ser Ala Lys Ile Ile Ala Thr Gly Phe
            260                 265                 270

Ile Ala Ser Thr Pro Gln Asn Ile Pro Thr Thr Leu Lys Arg Asp Gly
        275                 280                 285

Ser Asp Phe Ser Ala Ala Ile Met Ser Ala Leu Phe Arg Ser His Gln
    290                 295                 300

Leu Thr Ile Trp Thr Asp Val Asp Gly Val Tyr Ser Ala Asp Pro Arg
305                 310                 315                 320

Lys Val Ser Glu Ala Val Val Leu Lys Thr Leu Ser Tyr Gln Glu Ala
                325                 330                 335

Trp Glu Met Ser Tyr Phe Gly Ala Asn Val Leu His Pro Arg Thr Ile
            340                 345                 350

Ile Pro Val Met Lys Tyr Asp Ile Pro Ile Val Ile Arg Asn Ile Phe
        355                 360                 365
```

-continued

```
Asn Leu Ser Ala Pro Gly Thr Met Ile Cys Arg Gln Ile Asp Asp Glu
370                 375                 380
Asp Gly Phe Lys Leu Asp Ala Pro Val Lys Gly Phe Ala Thr Ile Asp
385                 390                 395                 400
Asn Leu Ala Leu Val Asn Val Glu Gly Thr Gly Met Ala Gly Val Pro
                405                 410                 415
Gly Thr Ala Ser Ala Ile Phe Ser Ala Val Lys Glu Val Gly Ala Asn
            420                 425                 430
Val Ile Met Ile Ser Gln Ala Ser Glu His Ser Val Cys Phe Ala
        435                 440                 445
Val Pro Glu Lys Glu Val Lys Ala Val Ser Glu Ala Leu Asn Ser Arg
450                 455                 460
Phe Arg Gln Ala Leu Ala Gly Arg Leu Ser Gln Ile Glu Ile Ile
465                 470                 475                 480
Pro Asn Cys Ser Ile Leu Ala Ala Val Gly Gln Lys Met Ala Ser Thr
                485                 490                 495
Pro Gly Val Ser Ala Thr Phe Phe Asn Ala Leu Ala Lys Ala Asn Ile
            500                 505                 510
Asn Ile Arg Ala Ile Ala Gln Gly Cys Ser Glu Phe Asn Ile Thr Val
        515                 520                 525
Val Val Lys Arg Glu Asp Cys Ile Arg Ala Leu Arg Ala Val His Ser
530                 535                 540
Arg Phe Tyr Leu Ser Arg Thr Thr Leu Ala Val Gly Ile Ile Gly Pro
545                 550                 555                 560
Gly Leu Ile Gly Gly Thr Leu Leu Asp Gln Ile Arg Asp Gln Ala Ala
                565                 570                 575
Val Leu Lys Glu Glu Phe Lys Ile Asp Leu Arg Val Ile Gly Ile Thr
            580                 585                 590
Gly Ser Ser Lys Met Leu Met Ser Glu Ser Gly Ile Asp Leu Ser Arg
        595                 600                 605
Trp Arg Glu Leu Met Lys Glu Glu Gly Leu Lys Ala Asp Met Glu Lys
610                 615                 620
Phe Thr Gln Tyr Val Lys Gly Asn His Phe Ile Pro Asn Ser Val Met
625                 630                 635                 640
Val Asp Cys Thr Ala Asp Ala Asp Ile Ala Ser Cys Tyr Tyr Asp Trp
                645                 650                 655
Leu Leu Arg Gly Ile His Val Val Thr Pro Asn Lys Lys Ala Asn Ser
            660                 665                 670
Gly Pro Leu Asp Gln Tyr Leu Lys Ile Arg Asp Leu Gln Arg Lys Ser
        675                 680                 685
Tyr Thr His Tyr Phe Tyr Glu Ala Thr Val Gly Ala Gly Leu Pro Ile
690                 695                 700
Ile Ser Thr Leu Arg Gly Leu Leu Glu Thr Gly Asp Lys Ile Leu Arg
705                 710                 715                 720
Ile Glu Gly Ile Phe Ser Gly Thr Leu Ser Tyr Leu Phe Asn Asn Phe
                725                 730                 735
Val Gly Thr Arg Ser Phe Ser Glu Val Val Ala Glu Ala Lys Gln Ala
            740                 745                 750
Gly Phe Thr Glu Pro Asp Pro Arg Asp Asp Leu Ser Gly Thr Asp Val
        755                 760                 765
Ala Arg Lys Val Thr Ile Leu Ala Arg Glu Ser Gly Leu Lys Leu Asp
770                 775                 780
Leu Glu Gly Leu Pro Val Gln Asn Leu Val Pro Lys Pro Leu Gln Ala
```

```
                785                 790                 795                 800
Cys Ala Ser Ala Glu Glu Phe Met Glu Lys Leu Pro Gln Phe Asp Glu
                    805                 810                 815
Glu Leu Ser Lys Gln Arg Glu Ala Glu Ala Gly Glu Val Leu
                820                 825                 830
Arg Tyr Val Gly Val Asp Ala Val Glu Lys Lys Gly Thr Val Glu
                835                 840                 845
Leu Lys Arg Tyr Lys Lys Asp His Pro Phe Ala Gln Leu Ser Gly Ala
850                 855                 860
Asp Asn Ile Ile Ala Phe Thr Thr Lys Arg Tyr Lys Glu Gln Pro Leu
865                 870                 875                 880
Ile Val Arg Gly Pro Gly Ala Gly Ala Gln Val Thr Ala Gly Gly Ile
                885                 890                 895
Phe Ser Asp Ile Leu Arg Leu Ala Phe Tyr Leu Gly Ala Pro Ser
                900                 905                 910

<210> SEQ ID NO 13
<211> LENGTH: 859
<212> TYPE: PRT
<213> ORGANISM: Arabidopsis thaliana

<400> SEQUENCE: 13

Met Ala Thr Leu Lys Pro Ser Phe Thr Val Ser Pro Pro Asn Ser Asn
1               5                   10                  15
Pro Ile Arg Phe Gly Ser Phe Pro Pro Gln Cys Phe Leu Arg Val Pro
                20                  25                  30
Lys Pro Arg Arg Leu Ile Leu Pro Arg Phe Arg Lys Thr Thr Gly Gly
            35                  40                  45
Gly Gly Gly Leu Ile Arg Cys Glu Leu Pro Asp Phe His Leu Ser Ala
        50                  55                  60
Thr Ala Thr Thr Val Ser Gly Val Ser Thr Val Asn Leu Val Asp Gln
65                  70                  75                  80
Val Gln Ile Pro Lys Gly Glu Met Trp Ser Val His Lys Phe Gly Gly
                85                  90                  95
Thr Cys Val Gly Asn Ser Gln Arg Ile Arg Asn Val Ala Glu Val Ile
                100                 105                 110
Ile Asn Asp Asn Ser Glu Arg Lys Leu Val Val Ser Ala Met Ser
            115                 120                 125
Lys Val Thr Asp Met Met Tyr Asp Leu Ile Arg Lys Ala Gln Ser Arg
130                 135                 140
Asp Asp Ser Tyr Leu Ser Ala Leu Glu Ala Val Leu Glu Lys His Arg
145                 150                 155                 160
Leu Thr Ala Arg Asp Leu Leu Asp Gly Asp Leu Ala Ser Phe Leu
                165                 170                 175
Ser His Leu His Asn Asp Ile Ser Asn Leu Lys Ala Met Leu Arg Ala
            180                 185                 190
Ile Tyr Ile Ala Gly His Ala Ser Glu Ser Phe Ser Asp Phe Val Ala
        195                 200                 205
Gly His Gly Glu Leu Trp Ser Ala Gln Met Leu Ser Tyr Val Val Arg
    210                 215                 220
Lys Thr Gly Leu Glu Cys Lys Trp Met Asp Thr Arg Asp Val Leu Ile
225                 230                 235                 240
Val Asn Pro Thr Ser Ser Asn Gln Val Asp Pro Asp Phe Gly Glu Ser
                245                 250                 255
```

Glu Lys Arg Leu Asp Lys Trp Phe Ser Leu Asn Pro Ser Lys Ile Ile
                260                 265                 270

Ile Ala Thr Gly Phe Ile Ala Ser Thr Pro Gln Asn Ile Pro Thr Thr
            275                 280                 285

Leu Lys Arg Asp Gly Ser Asp Phe Ser Ala Ala Ile Met Gly Ala Leu
        290                 295                 300

Leu Arg Ala Arg Gln Val Thr Ile Trp Thr Asp Val Asp Gly Val Tyr
305                 310                 315                 320

Ser Ala Asp Pro Arg Lys Val Asn Glu Ala Val Ile Leu Gln Thr Leu
                325                 330                 335

Ser Tyr Gln Glu Ala Trp Glu Met Ser Tyr Phe Gly Ala Asn Val Leu
            340                 345                 350

His Pro Arg Thr Ile Ile Pro Val Met Arg Tyr Asn Ile Pro Ile Val
        355                 360                 365

Ile Arg Asn Ile Phe Asn Leu Ser Ala Pro Gly Thr Ile Ile Cys Gln
370                 375                 380

Pro Pro Glu Asp Asp Tyr Asp Leu Lys Leu Thr Thr Pro Val Lys Gly
385                 390                 395                 400

Phe Ala Thr Ile Asp Asn Leu Ala Leu Ile Asn Val Glu Gly Thr Gly
                405                 410                 415

Met Ala Gly Val Pro Gly Thr Ala Ser Asp Ile Phe Gly Cys Val Lys
            420                 425                 430

Asp Val Gly Ala Asn Val Ile Met Ile Ser Gln Ala Ser Ser Glu His
        435                 440                 445

Ser Val Cys Phe Ala Val Pro Glu Lys Glu Val Asn Ala Val Ser Glu
450                 455                 460

Ala Leu Arg Ser Arg Phe Ser Glu Ala Leu Gln Ala Gly Arg Leu Ser
465                 470                 475                 480

Gln Ile Glu Val Ile Pro Asn Cys Ser Ile Leu Ala Ala Val Gly Gln
                485                 490                 495

Lys Met Ala Ser Thr Pro Gly Val Ser Cys Thr Leu Phe Ser Ala Leu
            500                 505                 510

Ala Lys Ala Asn Ile Asn Val Arg Ala Ile Ser Gln Gly Cys Ser Glu
        515                 520                 525

Tyr Asn Val Thr Val Val Ile Lys Arg Glu Asp Ser Val Lys Ala Leu
530                 535                 540

Arg Ala Val His Ser Arg Phe Phe Leu Ser Arg Thr Thr Leu Ala Met
545                 550                 555                 560

Gly Ile Val Gly Pro Gly Leu Ile Gly Ala Thr Leu Leu Asp Gln Leu
                565                 570                 575

Arg Asp Gln Ala Ala Val Leu Lys Gln Glu Phe Asn Ile Asp Leu Arg
            580                 585                 590

Val Leu Gly Ile Thr Gly Ser Lys Lys Met Leu Leu Ser Asp Ile Gly
        595                 600                 605

Ile Asp Leu Ser Arg Trp Arg Glu Leu Leu Asn Glu Lys Gly Thr Glu
610                 615                 620

Ala Asp Leu Asp Lys Phe Thr Gln Gln Val His Gly Asn His Phe Ile
625                 630                 635                 640

Pro Asn Ser Val Val Asp Cys Thr Ala Asp Ser Ala Ile Ala Ser
                645                 650                 655

Arg Tyr Tyr Asp Trp Leu Arg Lys Gly Ile His Val Ile Thr Pro Asn
            660                 665                 670

Lys Lys Ala Asn Ser Gly Pro Leu Asp Gln Tyr Leu Lys Leu Arg Asp

-continued

```
                675                 680                 685
Leu Gln Arg Lys Ser Tyr Thr His Tyr Phe Tyr Glu Ala Thr Val Gly
    690                 695                 700
Ala Gly Leu Pro Ile Ile Ser Thr Leu Arg Gly Leu Leu Glu Thr Gly
705                 710                 715                 720
Asp Lys Ile Leu Arg Ile Glu Gly Ile Cys Ser Gly Thr Leu Ser Tyr
                725                 730                 735
Leu Phe Asn Asn Phe Val Gly Asp Arg Ser Phe Ser Glu Val Val Thr
            740                 745                 750
Glu Ala Lys Asn Ala Gly Phe Thr Glu Pro Asp Pro Arg Asp Asp Leu
            755                 760                 765
Ser Gly Thr Asp Val Ala Arg Lys Val Ile Ile Leu Ala Arg Glu Ser
        770                 775                 780
Gly Leu Lys Leu Asp Leu Ala Asp Leu Pro Ile Arg Ser Leu Val Pro
785                 790                 795                 800
Glu Pro Leu Lys Gly Cys Thr Ser Val Glu Glu Phe Met Glu Lys Leu
                805                 810                 815
Pro Gln Tyr Asp Gly Asp Leu Ala Lys Glu Arg Leu Asp Ala Glu Asn
            820                 825                 830
Ser Gly Glu Val Arg Leu Phe Thr Thr Asn Val Phe Pro Phe Asp Gln
            835                 840                 845
Cys Asp His Ile Leu Thr Ile Tyr Ile Cys Met
        850                 855

<210> SEQ ID NO 14
<211> LENGTH: 918
<212> TYPE: PRT
<213> ORGANISM: Brachypodium distachyon

<400> SEQUENCE: 14

Met Arg Ser Leu Ala Ile Thr Ser Pro Val Pro Pro Thr Ser Ala Ala
1               5                   10                  15
Ala Ala Arg Arg Gln Pro Arg Ser Ser Ala Ser Gly Arg Glu Val Val
            20                  25                  30
Ser Gln Cys Leu Lys Cys Glu Ile Asn Lys Asp Arg Pro Leu Gly Gly
        35                  40                  45
Tyr Leu Arg Ile Gly Gln Ser Gln Gly Ser Leu Leu Arg His Gly Ser
    50                  55                  60
Lys Asn Phe Ile Ala Gln Ala Ala Ala Ile Ser Val Glu Gln Asp
65                  70                  75                  80
Glu Val Ser Thr Tyr Leu Pro Lys Gly Asp Met Trp Ser Val His Lys
                85                  90                  95
Phe Gly Gly Thr Cys Met Gly Thr Pro Gln Arg Ile Gln Asn Val Ala
            100                 105                 110
Asp Ile Val Leu Gly Asp Ser Ser Glu Arg Lys Leu Ile Ile Val Ser
        115                 120                 125
Ala Met Ser Lys Val Thr Asp Met Met Tyr Ser Leu Val His Lys Ala
    130                 135                 140
Gln Ser Arg Asp Asp Ser Tyr Thr Met Ala Leu Asp Gln Ile Phe Glu
145                 150                 155                 160
Lys His Met Ala Ser Ala Lys Glu Leu Leu Asp Gly Glu Asp Leu Ala
                165                 170                 175
Arg Phe Leu Ser Gln Leu His Ser Asp Ile Ser Asn Leu Arg Ala Met
            180                 185                 190
```

-continued

Leu Arg Ala Ile Tyr Ile Ala Gly His Ala Thr Glu Ser Phe Ser Glu
        195                 200                 205

Phe Val Val Gly His Gly Glu Leu Trp Ser Ala Gln Ile Leu Ser Tyr
210                 215                 220

Ala Ile Gln Lys Ser Gly Thr Ala Cys Ser Trp Met Asp Thr Arg Glu
225                 230                 235                 240

Val Leu Val Val Lys Pro Ser Gly Tyr Asn Leu Val Asp Pro Asp Tyr
                245                 250                 255

Leu Glu Ser Lys Lys Arg Leu Gln Lys Trp Phe Ser Arg Gln Pro Ala
            260                 265                 270

Glu Ile Ile Val Ala Thr Gly Phe Ile Ala Ser Thr Ala Glu Asn Ile
        275                 280                 285

Pro Thr Thr Leu Lys Arg Asp Gly Ser Asp Phe Ser Ala Ile Ile
290                 295                 300

Gly Ser Leu Val Arg Ala Arg Gln Val Thr Ile Trp Thr Asp Val Asp
305                 310                 315                 320

Gly Val Phe Ser Ala Asp Pro Arg Lys Val Ser Glu Ala Val Ile Leu
                325                 330                 335

Ser Thr Leu Ser Tyr Gln Glu Ala Trp Glu Met Ser Tyr Phe Gly Ala
            340                 345                 350

Asn Val Leu His Pro Arg Thr Ile Ile Pro Val Met Lys Asp Asn Ile
        355                 360                 365

Pro Ile Val Ile Arg Asn Met Phe Asn Leu Ser Ala Pro Gly Thr Val
370                 375                 380

Ile Cys Lys Gln Pro Ala Asn Glu Asp Gly Asp Leu Asp Ala Cys Val
385                 390                 395                 400

Lys Ser Phe Ala Thr Ile Asp Asn Leu Ala Leu Val Asn Val Glu Gly
                405                 410                 415

Thr Gly Met Ala Gly Val Pro Gly Thr Ser Ser Thr Ile Phe Ser Ala
            420                 425                 430

Val Lys Asp Val Gly Ala Asn Val Ile Met Ile Ser Gln Ala Ser Ser
        435                 440                 445

Glu His Ser Ile Cys Phe Ala Val Pro Glu Lys Glu Val Ala Ala Val
    450                 455                 460

Ser Ala Ala Leu His Val Arg Phe Arg Glu Ala Leu Ala Ala Gly Arg
465                 470                 475                 480

Leu Ser Lys Val Glu Ile Ile His Gly Cys Ser Ile Leu Ala Ala Val
                485                 490                 495

Gly Leu Arg Met Ala Ser Thr Pro Gly Val Ser Ala Ile Leu Phe Asp
            500                 505                 510

Ala Leu Ala Lys Ala Asn Ile Asn Val Arg Ala Ile Ala Gln Gly Cys
        515                 520                 525

Ser Glu Tyr Asn Ile Thr Val Val Leu Lys Gln Glu Asp Cys Val Arg
    530                 535                 540

Ala Leu Arg Ala Ala His Ser Arg Phe Phe Leu Ser Lys Thr Thr Leu
545                 550                 555                 560

Ala Val Gly Ile Ile Gly Pro Gly Leu Ile Gly Ala Thr Leu Ile Lys
                565                 570                 575

Gln Leu Gly Glu Gln Val Ala Val Leu Lys Glu Asn Met Asn Ile Asp
            580                 585                 590

Val Arg Val Val Gly Ile Thr Gly Ser Ser Thr Met Leu Leu Ser Asp
        595                 600                 605

Ser Gly Val Asp Leu Ser Arg Trp Lys Glu Asp Leu Gln Thr Glu Ser

```
                     610                 615                 620

Lys Pro Ala Asp Leu Ala Ile Phe Val Arg His Leu Ser Glu Asn His
625                 630                 635                 640

Val Phe Pro Asn Lys Val Leu Val Asp Cys Thr Ala Asp Thr Asn Val
                645                 650                 655

Ala Ser His Tyr Tyr Asp Trp Leu Lys Lys Gly Ile His Val Ile Thr
                660                 665                 670

Pro Asn Lys Lys Ala Asn Ser Gly Pro Leu Asp Arg Tyr Leu Lys Leu
            675                 680                 685

Arg Thr Leu Gln Arg Ala Ser Tyr Thr His Tyr Phe Tyr Glu Ala Thr
        690                 695                 700

Val Gly Ala Gly Leu Pro Ile Ile Ser Thr Leu Arg Gly Leu Leu Glu
705                 710                 715                 720

Thr Gly Asp Asn Ile Leu Arg Ile Glu Gly Ile Phe Ser Gly Thr Leu
                725                 730                 735

Ser Tyr Ile Phe Asn Asn Phe Glu Gly Thr Arg Ser Phe Ser Asp Val
                740                 745                 750

Val Ala Glu Ala Lys Glu Ala Gly Tyr Thr Glu Pro Asp Pro Arg Asp
            755                 760                 765

Asp Leu Ser Gly Thr Asp Val Ala Arg Lys Val Ile Ile Leu Ala Arg
        770                 775                 780

Glu Cys Gly Leu Arg Leu Glu Leu Ser Asp Ile Pro Val Lys Ser Leu
785                 790                 795                 800

Val Pro Glu Pro Leu Thr Ser Cys Ser Ser Ala Asp Glu Phe Met Gln
                805                 810                 815

Lys Leu Pro Ser Phe Asp Gln Asp Trp Ala Arg Gln Arg His Glu Ala
            820                 825                 830

Glu Ala Ala Gly Glu Val Leu Arg Tyr Val Gly Val Val Asp Val Leu
        835                 840                 845

Asn Lys Lys Gly Arg Val Glu Leu Gln Arg Tyr Lys Lys Asp His Pro
850                 855                 860

Phe Ala Gln Leu Ser Gly Ser Asp Asn Ile Ile Ala Phe Thr Thr Ser
865                 870                 875                 880

Arg Tyr Lys Glu Gln Pro Leu Met Val Arg Gly Pro Gly Ala Gly Ala
                885                 890                 895

Glu Val Thr Ala Gly Gly Val Phe Cys Asp Ile Leu Arg Leu Ala Ser
            900                 905                 910

Tyr Leu Gly Ala Pro Ser
        915

<210> SEQ ID NO 15
<211> LENGTH: 917
<212> TYPE: PRT
<213> ORGANISM: Zea mays

<400> SEQUENCE: 15

Met Gln Gly Leu Ala Val Ser Cys Gln Leu Pro Pro Ala Ala Ala Ala
1               5                   10                  15

Ala Arg Trp Arg Pro Arg Ala Ser Ser Ser Asn Arg Glu Ala Val Leu
            20                  25                  30

Gln Cys Trp Lys Tyr Glu Leu Ser Gln Asp His Tyr Leu Gly Gly Pro
        35                  40                  45

Leu Arg Ile Gly Gln Ser Gln Gly Ser Leu His Arg His Arg Ser Thr
    50                  55                  60
```

-continued

```
Asn Phe Leu Arg Pro Ala Ala Ala Ile Ser Val Glu Gln Asp Glu
 65                  70                  75                  80

Val Asn Thr Tyr Leu Pro Lys Gly Asp Met Trp Ser Val His Lys Phe
             85                  90                  95

Gly Gly Thr Cys Met Gly Thr Pro Lys Arg Ile Gln Cys Val Ala Asn
            100                 105                 110

Ile Val Leu Gly Asp Ser Ser Glu Arg Lys Leu Ile Ile Val Ser Ala
        115                 120                 125

Met Ser Lys Val Thr Asp Met Met Tyr Asn Leu Val Gln Lys Ala Gln
    130                 135                 140

Ser Arg Asp Asp Ser Tyr Ala Ile Ala Leu Ala Glu Val Phe Glu Lys
145                 150                 155                 160

His Met Thr Ala Ala Lys Asp Leu Leu Asp Gly Glu Asp Leu Ala Arg
                165                 170                 175

Phe Leu Ser Gln Leu His Ser Asp Val Ser Asn Leu Arg Ala Met Leu
            180                 185                 190

Arg Ala Ile Tyr Ile Ala Gly His Ala Thr Glu Ser Phe Ser Asp Phe
        195                 200                 205

Val Val Gly His Gly Glu Leu Trp Ser Ala Gln Met Leu Ser Tyr Ala
    210                 215                 220

Ile Lys Lys Ser Gly Ala Pro Cys Ser Trp Met Asp Thr Arg Glu Val
225                 230                 235                 240

Leu Val Val Thr Pro Ser Gly Cys Asn Gln Val Asp Pro Asp Tyr Leu
                245                 250                 255

Glu Cys Glu Lys Arg Leu Gln Lys Trp Phe Ser Arg Gln Pro Ala Glu
            260                 265                 270

Ile Ile Val Ala Thr Gly Phe Ile Ala Ser Thr Ala Gly Asn Ile Pro
        275                 280                 285

Thr Thr Leu Lys Arg Asp Gly Ser Asp Phe Ser Ala Ile Val Gly
    290                 295                 300

Ser Leu Val Arg Ala Arg Gln Val Thr Ile Trp Thr Asp Val Asp Gly
305                 310                 315                 320

Val Phe Ser Ala Asp Pro Arg Lys Val Ser Glu Ala Val Ile Leu Ser
                325                 330                 335

Thr Leu Ser Tyr Gln Glu Ala Trp Glu Met Ser Tyr Phe Gly Ala Asn
            340                 345                 350

Val Leu His Pro Arg Thr Ile Ile Pro Val Met Lys Asp Asn Ile Pro
        355                 360                 365

Ile Val Ile Arg Asn Met Phe Asn Leu Ser Ala Pro Gly Thr Met Ile
    370                 375                 380

Cys Lys Gln Pro Ala Asn Glu Asn Gly Asp Leu Asp Ala Cys Val Lys
385                 390                 395                 400

Ser Phe Ala Thr Val Asp Asn Leu Ala Leu Val Asn Val Glu Gly Thr
                405                 410                 415

Gly Met Ala Gly Val Pro Gly Thr Ala Ser Ala Ile Phe Ser Ala Val
            420                 425                 430

Lys Asp Val Gly Ala Asn Val Ile Met Ile Ser Gln Ala Ser Ser Glu
        435                 440                 445

His Ser Val Cys Phe Ala Val Pro Glu Lys Glu Val Ala Val Val Ser
    450                 455                 460

Ala Glu Leu His Asp Arg Phe Arg Glu Ala Leu Ala Ala Gly Arg Leu
465                 470                 475                 480

Ser Lys Val Glu Val Ile Asn Gly Cys Ser Ile Leu Ala Ala Val Gly
```

```
                    485                 490                 495

Leu Arg Met Ala Ser Thr Pro Gly Val Ser Ala Ile Leu Phe Asp Ala
                500                 505                 510

Leu Ala Lys Ala Asn Ile Asn Val Arg Ala Ile Ala Gln Gly Cys Ser
                515                 520                 525

Glu Tyr Asn Ile Thr Val Val Leu Lys Gln Gln Asp Cys Val Arg Ala
            530                 535                 540

Leu Arg Ala Ala His Ser Arg Phe Phe Leu Ser Lys Thr Thr Leu Ala
545                 550                 555                 560

Val Gly Ile Ile Gly Pro Gly Leu Ile Gly Gly Ala Leu Leu Asn Gln
                565                 570                 575

Leu Lys Asn Gln Thr Ala Val Leu Lys Glu Asn Met Asn Ile Asp Leu
                580                 585                 590

Arg Val Ile Gly Ile Thr Gly Ser Ser Thr Met Leu Leu Ser Asp Thr
                595                 600                 605

Gly Ile Asp Leu Thr Gln Trp Lys Gln Leu Leu Gln Lys Glu Ala Glu
                610                 615                 620

Pro Ala Asp Ile Gly Ser Phe Val His His Leu Ser Asp Asn His Val
625                 630                 635                 640

Phe Pro Asn Lys Val Leu Val Asp Cys Thr Ala Asp Thr Ser Val Ala
                645                 650                 655

Ser His Tyr Tyr Asp Trp Leu Lys Lys Gly Ile His Val Ile Thr Pro
                660                 665                 670

Asn Lys Lys Ala Asn Ser Gly Pro Leu Asp Gln Tyr Leu Lys Leu Arg
                675                 680                 685

Thr Met Gln Arg Ala Ser Tyr Thr His Tyr Phe Tyr Glu Ala Thr Val
                690                 695                 700

Gly Ala Gly Leu Pro Ile Ile Ser Thr Leu Arg Gly Leu Leu Glu Thr
705                 710                 715                 720

Gly Asp Lys Ile Leu Arg Ile Glu Gly Ile Phe Ser Gly Thr Leu Ser
                725                 730                 735

Tyr Ile Phe Asn Asn Phe Glu Gly Thr Arg Ala Phe Ser Asp Val Val
                740                 745                 750

Ala Glu Ala Arg Glu Ala Gly Tyr Thr Glu Pro Asp Pro Arg Asp Asp
                755                 760                 765

Leu Ser Gly Thr Asp Val Ala Arg Lys Val Val Leu Ala Arg Glu
                770                 775                 780

Ser Gly Leu Arg Leu Glu Leu Ser Asp Ile Pro Val Lys Ser Leu Val
785                 790                 795                 800

Pro Glu Thr Leu Ala Ser Cys Ser Ser Ala Asp Glu Phe Met Gln Lys
                805                 810                 815

Leu Pro Ser Phe Asp Glu Asp Trp Ala Arg Gln Arg Ser Asp Ala Glu
                820                 825                 830

Ala Ala Gly Glu Val Leu Arg Tyr Val Gly Ala Leu Asp Ala Val Asn
                835                 840                 845

Arg Ser Gly Gln Val Glu Leu Arg Arg Tyr Arg Arg Asp His Pro Phe
                850                 855                 860

Ala Gln Leu Ser Gly Ser Asp Asn Ile Ile Ala Phe Thr Thr Ser Arg
865                 870                 875                 880

Tyr Lys Glu Gln Pro Leu Ile Val Arg Gly Pro Gly Ala Gly Ala Glu
                885                 890                 895

Val Thr Ala Gly Gly Val Phe Cys Asp Ile Leu Arg Leu Ala Ser Tyr
                900                 905                 910
```

Leu Gly Ala Pro Ser
        915

<210> SEQ ID NO 16
<211> LENGTH: 798
<212> TYPE: PRT
<213> ORGANISM: Zea mays

<400> SEQUENCE: 16

Met Gln Ser Leu Thr Val Ala Arg Ala Leu Pro Pro Ala Val Ala Thr
1               5                   10                  15

Ala Arg Arg Arg Pro Arg Ala Ser Ser Ser Arg Glu Ala Val Leu
            20                  25                  30

Gln Cys Trp Lys Tyr Glu Leu Ser Gln Asp Gln Tyr Leu Gly Gly Ser
        35                  40                  45

Leu Arg Ile Gly Ser Ser Gln Gly Ser Leu Asp Ile His Arg Ser Thr
    50                  55                  60

Asn Leu Leu Arg Pro Ala Ala Ala Ser Val Ser Val Glu Gln Asp Glu
65                  70                  75                  80

Val Asn Thr Tyr Leu Pro Lys Gly Asp Met Trp Ser Val His Lys Phe
                85                  90                  95

Gly Gly Thr Cys Met Gly Thr Ser Gln Arg Ile Gln Ser Val Ala Asn
            100                 105                 110

Ile Val Leu Gly Asp Ser Ser Glu Arg Lys Leu Ile Ile Val Ser Ala
        115                 120                 125

Met Ser Lys Val Thr Asp Met Met Tyr Asn Leu Val Gln Lys Ala Gln
    130                 135                 140

Ser Arg Asp Asp Ser Tyr Thr Ile Ala Leu Glu Glu Val Phe Glu Lys
145                 150                 155                 160

His Met Val Ala Ala Lys Asp Leu Ile Asp Gly Glu Asp Leu Ala Arg
                165                 170                 175

Phe Leu Ser Gln Leu His Ser Asp Val Ser Asn Leu Arg Ala Met Leu
            180                 185                 190

Arg Ala Ile Tyr Ile Ala Gly His Ala Thr Glu Ser Phe Ser Asp Phe
        195                 200                 205

Val Val Gly His Gly Glu Leu Trp Ser Ala Gln Met Leu Ser Tyr Ala
    210                 215                 220

Ile Lys Lys Ser Tyr Phe Gly Ala Asn Val Leu His Pro Arg Thr Ile
225                 230                 235                 240

Ile Pro Val Met Lys Asp Asn Ile Pro Ile Val Ile Arg Asn Met Phe
                245                 250                 255

Asn Leu Ser Ala Ser Gly Thr Met Ile Cys Lys Gln Pro Ala Asn Glu
            260                 265                 270

Asn Gly Asp Leu Asp Ala Cys Val Lys Ser Phe Ala Thr Ile Asp Asn
        275                 280                 285

Leu Ala Leu Val Asn Val Glu Gly Thr Gly Met Ala Gly Val Pro Gly
    290                 295                 300

Thr Ala Ser Ala Ile Phe Ser Thr Val Lys Asp Val Gly Ala Asn Val
305                 310                 315                 320

Ile Met Ile Ser Gln Ala Ser Ser Glu His Ser Val Cys Phe Ala Val
                325                 330                 335

Pro Glu Lys Glu Val Ala Ala Val Ser Ala Arg Leu His Asp Arg Phe
            340                 345                 350

His Glu Ala Leu Ala Ala Gly Arg Leu Ser Lys Val Glu Val Ile Asn

```
                    355                 360                 365
Gly Cys Ser Ile Leu Ala Ala Val Gly Leu Arg Met Ala Ser Thr Pro
    370                 375                 380

Gly Val Ser Ala Ile Leu Phe Asp Ala Leu Ala Lys Ala Asn Ile Asn
385                 390                 395                 400

Val Arg Ala Ile Ala Gln Gly Cys Ser Glu Tyr Asn Ile Thr Val Val
                405                 410                 415

Leu Lys Gln Glu Asp Cys Val Arg Ala Leu Arg Ala Ala His Ser Arg
            420                 425                 430

Phe Phe Leu Ser Lys Thr Thr Leu Ala Val Gly Ile Ile Gly Pro Gly
        435                 440                 445

Leu Ile Gly Arg Thr Leu Leu Asn Gln Leu Lys Asp Gln Val Ala Ala
    450                 455                 460

Leu Lys Glu Asn Met Asn Ile Asp Leu Arg Val Ile Gly Ile Thr Gly
465                 470                 475                 480

Ser Ser Thr Met Leu Leu Ser Asp Thr Gly Ile Asp Leu Thr Gln Trp
                485                 490                 495

Lys Gln Leu Leu Lys Lys Glu Ala Glu Pro Ala Asp Ile Asp Ser Phe
            500                 505                 510

Val His His Leu Ser Asp Asn His Val Phe Pro Asn Lys Val Leu Val
        515                 520                 525

Asp Cys Thr Ala Asp Thr Ser Val Ala Ser His Tyr Tyr Asn Trp Leu
    530                 535                 540

Lys Lys Gly Ile His Val Ile Thr Pro Asn Lys Lys Ala Asn Ser Gly
545                 550                 555                 560

Pro Leu Asp Gln Tyr Leu Lys Leu Arg Thr Leu Gln Arg Ala Ser Tyr
                565                 570                 575

Thr His Tyr Phe Tyr Glu Ala Thr Val Gly Ala Gly Leu Pro Ile Ile
            580                 585                 590

Ser Thr Leu Arg Gly Leu Leu Glu Thr Gly Asp Lys Ile Leu Arg Ile
        595                 600                 605

Glu Gly Ile Phe Ser Gly Thr Leu Ser Tyr Ile Phe Asn Asn Phe Glu
    610                 615                 620

Gly Thr Arg Ala Phe Ser Asp Val Val Ala Glu Ala Lys Glu Ala Gly
625                 630                 635                 640

Tyr Thr Glu Pro Asp Pro Arg Asp Asp Leu Ser Gly Thr Asp Val Ala
                645                 650                 655

Arg Lys Val Ile Ile Leu Ala Arg Glu Ser Gly Leu Arg Leu Glu Leu
            660                 665                 670

Ser Asp Ile Pro Val Lys Ser Leu Val Pro Glu Thr Leu Ala Ala Cys
        675                 680                 685

Ser Ser Ala Asp Glu Phe Met Gln Lys Leu Pro Ser Phe Asp Glu Asp
    690                 695                 700

Trp Ala Arg Gln Arg Ser Asp Ala Asp Ala Asp Glu Val Leu Arg
705                 710                 715                 720

Tyr Val Gly Val Val Asp Thr Val Asn Lys Arg Gly Gln Val Glu Leu
                725                 730                 735

Arg Arg Tyr Lys Arg Asp His Pro Phe Ala Gln Leu Ser Gly Ser Asp
            740                 745                 750

Asn Ile Ile Ala Phe Thr Thr Ser Arg Tyr Lys Glu Gln Pro Leu Ile
        755                 760                 765

Val Arg Gly Pro Gly Ala Gly Ala Glu Val Thr Ala Gly Gly Val Phe
    770                 775                 780
```

```
Cys Asp Ile Leu Arg Leu Ala Ser Tyr Leu Gly Ala Pro Ser
785                 790                 795
```

<210> SEQ ID NO 17
<211> LENGTH: 682
<212> TYPE: PRT
<213> ORGANISM: Hordeum vulgare

<400> SEQUENCE: 17

```
Met Ile Leu Leu Ser Pro Ser Asp Lys Ser Gly Ala Ser Cys Ser Trp
1               5                   10                  15

Met Asp Thr Arg Glu Val Leu Val Val Lys Pro Ser Gly Pro Asp Met
            20                  25                  30

Val Asp Pro Asp Tyr Val Glu Ser Glu Lys Arg Leu Glu Lys Trp Phe
        35                  40                  45

Ser Arg Gln Pro Ala Glu Ile Ile Val Ala Thr Gly Phe Ile Ala Ser
    50                  55                  60

Thr Ala Glu Asn Ile Pro Thr Thr Leu Lys Arg Asp Gly Ser Asp Phe
65                  70                  75                  80

Ser Ala Ala Ile Ile Gly Ser Leu Val Arg Ala Cys Gln Val Thr Ile
                85                  90                  95

Trp Thr Asp Val Asp Gly Val Phe Ser Ala Asp Pro Arg Lys Val Ser
            100                 105                 110

Glu Ala Val Ile Leu Ser Thr Leu Ser Tyr Gln Glu Ala Trp Glu Met
        115                 120                 125

Ser Tyr Phe Gly Ala Asn Val Leu His Pro Arg Thr Ile Ile Pro Val
    130                 135                 140

Met Lys Asp Asn Ile Pro Ile Val Ile Arg Asn Met Phe Asn Leu Ser
145                 150                 155                 160

Ala Pro Gly Thr Val Ile Cys Lys Gln Pro Ala Asn Glu Asp Ala Asp
                165                 170                 175

Leu Asp Ala Cys Val Lys Ser Phe Ala Thr Ile Asp Lys Leu Ala Leu
            180                 185                 190

Val Asn Val Glu Gly Thr Gly Met Ala Gly Val Pro Gly Thr Ser Ser
        195                 200                 205

Ala Ile Phe Ser Ala Val Lys Glu Val Gly Ala Asn Val Ile Met Ile
    210                 215                 220

Ser Gln Ala Ser Ser Glu His Ser Ile Cys Phe Ala Val Pro Glu Lys
225                 230                 235                 240

Glu Val Ala Ala Val Ser Ala Ala Leu His Val Arg Phe Arg Glu Ala
                245                 250                 255

Leu Ala Ala Gly Arg Leu Ser Lys Val Glu Val Ile His Asp Cys Ser
            260                 265                 270

Ile Leu Ala Ala Val Gly Leu Arg Met Ala Ser Thr Pro Gly Val Ser
        275                 280                 285

Ala Ile Leu Phe Asp Ala Leu Ala Lys Ala Asn Ile Asn Val Arg Ala
    290                 295                 300

Ile Ala Gln Gly Cys Ser Glu Tyr Asn Ile Thr Val Val Leu Lys Gln
305                 310                 315                 320

Glu Asp Cys Val Arg Ala Leu Arg Ala Ala His Ser Arg Phe Phe Leu
                325                 330                 335

Ser Lys Thr Thr Leu Ala Ile Gly Val Ile Gly Pro Gly Leu Ile Gly
            340                 345                 350

Ala Thr Leu Leu Asn Gln Leu Arg Asp Gln Val Ala Val Leu Lys Glu
```

```
                355                 360                 365
Asn Met Asn Ile Asp Val Arg Val Gly Ile Thr Gly Ala Ser Thr
    370                 375                 380
Met Leu Leu Ser Asp Thr Gly Val Asp Leu Thr Arg Trp Lys Glu Glu
385                 390                 395                 400
Met Gln Lys Glu Ala Lys Pro Ala Asp Leu Ala Asn Phe Val Arg His
                405                 410                 415
Leu Ser Glu Asp His Val Phe Pro Asn Lys Val Leu Val Asp Cys Thr
                420                 425                 430
Ala Asp Thr Asn Val Ala Ser His Tyr Tyr Asp Trp Leu Lys Lys Gly
            435                 440                 445
Ile His Val Ile Thr Pro Asn Lys Lys Ala Asn Ser Gly Pro Leu Asp
            450                 455                 460
Arg Tyr Leu Lys Leu Arg Thr Leu Gln Arg Ala Ser Tyr Thr His Tyr
465                 470                 475                 480
Phe Tyr Glu Ala Thr Val Gly Ala Gly Leu Pro Ile Ile Ser Thr Leu
                485                 490                 495
Arg Gly Leu Leu Glu Thr Gly Asp Lys Ile Leu Arg Ile Glu Gly Ile
            500                 505                 510
Phe Ser Gly Thr Leu Ser Tyr Ile Phe Asn Asn Phe Glu Gly Thr Arg
            515                 520                 525
Ser Phe Ser Asp Val Val Ala Glu Ala Lys Ala Gly Tyr Thr Glu
            530                 535                 540
Pro Asp Pro Arg Asp Asp Leu Ser Gly Thr Asp Val Ala Arg Lys Val
545                 550                 555                 560
Ile Ile Leu Ala Arg Glu Ser Gly Leu Arg Leu Glu Leu Ser Asp Ile
                565                 570                 575
Pro Val Gly Ser Leu Val Pro Glu Ala Leu Lys Asp Trp Ala Arg Gln
            580                 585                 590
Arg His Glu Ala Glu Ala Ala Gly Glu Val Leu Arg Tyr Val Gly Val
            595                 600                 605
Val Asp Val Leu Asn Gly Lys Gly Arg Val Glu Leu Gln Arg Tyr Lys
610                 615                 620
Arg Asp His Pro Phe Ala Gln Leu Ser Gly Ser Asp Asn Ile Ile Ala
625                 630                 635                 640
Phe Thr Thr Ser Arg Tyr Lys Glu Gln Pro Leu Ile Val Arg Gly Pro
                645                 650                 655
Gly Ala Gly Ala Glu Val Thr Ala Gly Gly Val Phe Cys Asp Ile Leu
            660                 665                 670
Arg Leu Ala Ser Tyr Leu Gly Ala Pro Ser
            675                 680

<210> SEQ ID NO 18
<211> LENGTH: 897
<212> TYPE: PRT
<213> ORGANISM: Hordeum vulgare

<400> SEQUENCE: 18

Met Arg Ser Leu Ala Val Ala Ser Pro Val Pro Pro Ala Ala His
1               5                   10                  15

Arg Arg Arg Leu Arg Pro Ser Ala Ser Gly Arg Glu Val Val Ser Gln
                20                  25                  30

Cys Leu Lys Cys Glu Ile Asn Gln Asp Arg Pro Met Gly Ala Leu Arg
            35                  40                  45
```

```
Ile Gly His Ser Gln Gly Asn Leu Pro Arg His Gly Ser Lys Asn Leu
 50                  55                  60
Leu Thr Pro Ala Ala Ile Ser Val Glu Gln Val Glu Val Ser Thr
 65                  70                  75                  80
Tyr Leu Pro Lys Gly Asp Met Trp Ser Val His Lys Phe Gly Gly Thr
                     85                  90                  95
Cys Met Gly Thr Pro Gln Arg Ile Gln Asn Val Ala Asp Val Val Leu
                100                 105                 110
Gly Asp Ser Ser Glu Arg Lys Leu Ile Ile Val Ser Ala Met Ser Lys
                115                 120                 125
Val Thr Asp Met Met Tyr Ser Leu Val His Lys Ala Gln Ser Arg Asp
130                 135                 140
Asp Ser Tyr Thr Glu Glu Leu Asp Lys Val Phe Glu Lys His Met Ala
145                 150                 155                 160
Ala Ala Lys Asp Leu Leu Asp Gly Glu Asn Leu Ala Arg Phe Leu Ser
                165                 170                 175
Glu Leu His Ser Asp Ile Ser Asn Leu Arg Ala Met Leu Arg Ala Ile
                180                 185                 190
Tyr Ile Ala Gly His Ala Thr Glu Ser Phe Ser Glu Phe Val Val Gly
                195                 200                 205
His Gly Glu Leu Trp Ser Ser Gln Met Leu Ser Tyr Ala Val Gln Lys
                210                 215                 220
Ser Gly Ala Ser Cys Ser Trp Met Asp Thr Arg Glu Val Leu Val Val
225                 230                 235                 240
Lys Pro Ser Gly Pro Asp Met Val Asp Pro Asp Tyr Glu Glu Ser Glu
                245                 250                 255
Lys Arg Leu Glu Lys Trp Phe Ser Arg Gln Pro Ala Glu Ile Ile Val
                260                 265                 270
Ala Thr Gly Phe Ile Ala Ser Thr Ala Glu Asn Ile Pro Thr Thr Leu
                275                 280                 285
Lys Arg Asp Gly Ser Asp Phe Ser Ala Ala Ile Ile Gly Ser Leu Val
                290                 295                 300
Arg Ala Arg Gln Val Thr Ile Trp Thr Asp Val Asp Gly Val Phe Ser
305                 310                 315                 320
Ala Asp Pro Arg Lys Val Ser Glu Ala Val Ile Leu Ser Thr Leu Ser
                325                 330                 335
Tyr Gln Glu Ala Trp Glu Met Ser Tyr Phe Gly Ala Asn Val Leu His
                340                 345                 350
Pro Arg Thr Ile Ile Pro Val Met Lys Asp Asn Ile Pro Ile Val Ile
                355                 360                 365
Arg Asn Met Phe Asn Leu Ser Ala Pro Gly Thr Val Ile Cys Lys Gln
370                 375                 380
Pro Ala Asn Glu Asp Ala Asp Leu Asp Ala Cys Val Lys Ser Phe Ala
385                 390                 395                 400
Thr Ile Asp Lys Leu Ala Leu Val Asn Val Glu Gly Thr Gly Met Ala
                405                 410                 415
Gly Val Pro Gly Thr Ser Ser Ala Ile Phe Ser Ala Val Lys Glu Val
                420                 425                 430
Gly Ala Asn Val Ile Met Ile Ser Gln Ala Ser Ser Glu His Ser Ile
                435                 440                 445
Cys Phe Ala Val Pro Glu Lys Glu Val Ala Ala Val Ser Ala Ala Leu
450                 455                 460
His Val Arg Phe Arg Glu Ala Leu Ala Ala Gly Arg Leu Ser Lys Val
```

```
                465                 470                 475                 480
        Glu Val Ile His Asp Cys Ser Ile Leu Ala Ala Val Gly Leu Arg Met
                            485                 490                 495
        Ala Ser Thr Pro Gly Val Ser Ala Ile Leu Phe Asp Ala Leu Ala Lys
                            500                 505                 510
        Ala Asn Ile Asn Val Arg Ala Ile Ala Gln Gly Cys Ser Glu Tyr Asn
                            515                 520                 525
        Ile Thr Val Val Leu Lys Gln Glu Asp Cys Val Arg Ala Leu Arg Ala
                            530                 535                 540
        Ala His Ser Arg Phe Phe Leu Ser Lys Thr Thr Leu Ala Ile Gly Val
        545                 550                 555                 560
        Ile Gly Pro Gly Leu Ile Gly Ala Thr Leu Leu Asn Gln Leu Arg Asp
                            565                 570                 575
        Gln Val Ala Ile Leu Lys Glu Asn Met Asn Ile Asp Val Arg Val Ile
                            580                 585                 590
        Gly Ile Thr Gly Ala Ser Thr Met Leu Leu Ser Glu Thr Gly Val Asp
                            595                 600                 605
        Leu Thr Arg Trp Lys Glu Met Gln Lys Glu Ala Lys Pro Ala Asp
                            610                 615                 620
        Leu Ala Asn Phe Val Arg His Leu Ser Glu Asp His Val Phe Pro Asn
        625                 630                 635                 640
        Lys Val Leu Val Asp Cys Thr Ala Asp Thr Asn Val Ala Ser His Tyr
                            645                 650                 655
        Tyr Asp Trp Leu Lys Lys Gly Ile His Val Ile Thr Pro Asn Lys Lys
                            660                 665                 670
        Ala Asn Ser Gly Pro Leu Asp Arg Tyr Leu Lys Leu Arg Thr Leu Gln
                            675                 680                 685
        Arg Ala Ser Tyr Thr His Tyr Phe Tyr Glu Ala Thr Val Gly Ala Gly
                            690                 695                 700
        Leu Pro Ile Ile Ser Thr Leu Arg Gly Leu Leu Glu Thr Gly Asp Lys
        705                 710                 715                 720
        Ile Leu Arg Ile Glu Gly Ile Phe Ser Gly Thr Leu Ser Tyr Ile Phe
                            725                 730                 735
        Asn Asn Phe Glu Gly Thr Arg Ser Phe Ser Asp Val Val Ala Glu Ala
                            740                 745                 750
        Lys Glu Ala Gly Tyr Thr Glu Pro Asp Pro Arg Asp Asp Leu Ser Gly
                            755                 760                 765
        Thr Asp Val Ala Arg Lys Val Ile Ile Leu Ala Arg Glu Ser Gly Leu
                            770                 775                 780
        Arg Leu Glu Leu Ser Asp Ile Pro Val Glu Ser Leu Val Pro Glu Ala
        785                 790                 795                 800
        Leu Lys Asp Trp Ala Arg Gln Arg His Glu Ala Glu Ala Ala Gly Glu
                            805                 810                 815
        Val Leu Arg Tyr Val Gly Ala Val Asp Val Leu Asn Gly Lys Gly Arg
                            820                 825                 830
        Val Glu Leu Gln Arg Tyr Lys Arg Asp His Pro Phe Ala Gln Leu Ser
                            835                 840                 845
        Gly Ser Asp Asn Ile Ile Ala Phe Thr Thr Ser Arg Tyr Lys Glu Gln
                            850                 855                 860
        Pro Leu Ile Val Arg Gly Pro Gly Ala Gly Ala Glu Val Thr Ala Gly
        865                 870                 875                 880
        Gly Val Phe Cys Asp Ile Leu Arg Leu Ala Ser Tyr Leu Gly Ala Pro
                            885                 890                 895
```

Ser

<210> SEQ ID NO 19
<211> LENGTH: 921
<212> TYPE: PRT
<213> ORGANISM: Oryza sativa

<400> SEQUENCE: 19

```
Met Trp Ser Leu Ala Val Ala Ser Pro His Pro Ala Ala Phe Ala
1               5                   10                  15

Ala Ala Arg Pro Arg Arg Gly Pro Arg Pro Ala Ala Pro Ser His
                20                  25                  30

Arg Gly Val Asn Pro Gln Arg Trp Arg Cys Glu Lys Thr Gln Ala Trp
            35                  40                  45

Ser Phe Trp Ser Ser Leu Trp Ala Ser Asp Leu Pro Gly Gly Leu Tyr
        50                  55                  60

Gly Asp Val Ser Lys Asn Met Leu Lys Pro Ala Ala Val Ser Val
65                  70                  75                  80

Glu Gln Ala Glu Ala Ser Ala His Leu Pro Lys Gly Asp Met Trp Ser
                85                  90                  95

Val His Lys Phe Gly Gly Thr Cys Met Gly Thr Ser Gln Arg Ile Gln
                100                 105                 110

Asn Val Ala Asp Ile Ile Leu Arg Asp Pro Ser Glu Arg Lys Leu Val
                115                 120                 125

Val Val Ser Ala Met Ser Lys Val Thr Asp Met Met Tyr Asn Leu Val
            130                 135                 140

Asn Lys Ala Gln Ser Arg Asp Asp Ser Tyr Ile Thr Ala Leu Asp Glu
145                 150                 155                 160

Val Phe Glu Lys His Met Ala Ala Lys Asp Leu Leu Gly Gly Glu
                165                 170                 175

Asp Leu Ala Arg Phe Leu Ser Gln Leu His Ala Asp Val Ser Asn Leu
            180                 185                 190

Lys Ala Met Leu Arg Ala Ile Cys Ile Ala Gly His Ala Thr Glu Ser
            195                 200                 205

Phe Ser Asp Phe Val Val Gly His Gly Glu Ile Trp Ser Ala Gln Leu
210                 215                 220

Leu Ser Phe Ala Ile Lys Lys Ser Gly Thr Pro Cys Ser Trp Met Asp
225                 230                 235                 240

Thr Arg Glu Val Leu Val Val Asn Pro Thr Gly Ser Asn Gln Val Asp
                245                 250                 255

Pro Asp Tyr Leu Glu Ser Glu Lys Arg Leu Glu Lys Trp Phe Ala Arg
            260                 265                 270

Gln Pro Ala Glu Thr Ile Ile Ala Thr Gly Phe Ile Ala Ser Thr Pro
            275                 280                 285

Glu Asn Ile Pro Thr Thr Leu Lys Arg Asp Gly Ser Asp Phe Ser Ala
            290                 295                 300

Ala Ile Ile Gly Ser Leu Val Lys Ala Gly Gln Val Thr Ile Trp Thr
305                 310                 315                 320

Asp Val Asp Gly Val Phe Ser Asp Pro Arg Lys Val Ser Glu Ala
                325                 330                 335

Val Ile Leu Ser Thr Leu Ser Tyr Gln Glu Ala Trp Glu Met Ser Tyr
            340                 345                 350

Phe Gly Ala Asn Val Leu His Pro Arg Thr Ile Ile Pro Val Met Lys
            355                 360                 365
```

```
Tyr Asn Ile Pro Ile Val Ile Arg Asn Met Phe Asn Ile Ser Ala Pro
    370                 375                 380

Gly Thr Met Ile Cys Gln Gln Pro Ala Asn Glu Ser Gly Asp Leu Glu
385                 390                 395                 400

Ala Cys Val Lys Ala Phe Ala Thr Ile Asp Lys Leu Ser Leu Val Asn
                405                 410                 415

Val Glu Gly Thr Gly Met Ala Gly Val Pro Gly Thr Ala Ser Ala Ile
            420                 425                 430

Phe Gly Ala Val Lys Asp Val Gly Ala Asn Val Ile Met Ile Ser Gln
        435                 440                 445

Ala Ser Ser Glu His Ser Val Cys Phe Ala Val Pro Glu Lys Glu Val
450                 455                 460

Ala Ala Val Ser Ala Ala Leu His Val Arg Phe Arg Glu Ala Leu Ser
465                 470                 475                 480

Ala Gly Arg Leu Ser Lys Val Glu Val Ile His Asn Cys Ser Ile Leu
                485                 490                 495

Ala Ala Val Gly Leu Lys Met Ala Ser Thr Pro Gly Val Ser Ala Thr
            500                 505                 510

Leu Phe Asp Ala Leu Ala Lys Ala Asn Ile Asn Val Arg Ala Ile Ala
        515                 520                 525

Gln Gly Cys Ser Glu Tyr Asn Ile Thr Val Val Leu Lys Gln Glu Asp
530                 535                 540

Cys Val Arg Ala Leu Arg Ala Ala His Ser Arg Phe Phe Leu Ser Lys
545                 550                 555                 560

Thr Thr Leu Ala Val Gly Ile Ile Gly Pro Gly Leu Ile Gly Arg Thr
                565                 570                 575

Leu Leu Asn Gln Leu Lys Asp Gln Ala Ala Val Leu Lys Glu Asn Met
            580                 585                 590

Asn Ile Asp Leu Arg Val Met Gly Ile Thr Gly Ser Arg Thr Met Val
        595                 600                 605

Leu Ser Asp Thr Gly Ile Asp Leu Ala His Trp Lys Glu Gln Leu Gln
610                 615                 620

Thr Glu Ala Glu Pro Ala Asn Leu Asp Lys Phe Val Asp His Leu Ser
625                 630                 635                 640

Glu Asn Gln Leu Phe Pro Asn Arg Val Leu Val Asp Cys Thr Ala Asp
                645                 650                 655

Thr Ser Val Ala Ser His Tyr Tyr Asp Trp Leu Lys Lys Gly Ile His
            660                 665                 670

Val Ile Thr Pro Asn Lys Lys Ala Asn Ser Gly Pro Leu Asp Lys Tyr
        675                 680                 685

Leu Lys Leu Arg Thr Leu Gln Arg Ala Ser Tyr Thr His Tyr Phe Tyr
690                 695                 700

Glu Ala Thr Val Gly Ala Gly Leu Pro Ile Ile Ser Thr Leu Arg Gly
705                 710                 715                 720

Leu Leu Glu Thr Gly Asp Lys Ile Leu Arg Ile Glu Gly Ile Phe Ser
                725                 730                 735

Gly Thr Leu Ser Tyr Ile Phe Asn Asn Phe Glu Gly Thr Arg Ala Phe
            740                 745                 750

Ser Asp Val Val Ser Glu Ala Lys Glu Ala Gly Tyr Thr Glu Pro Asp
        755                 760                 765

Pro Arg Asp Asp Leu Ser Gly Thr Asp Val Ala Arg Lys Val Ile Ile
770                 775                 780
```

```
Leu Ala Arg Glu Ser Gly Leu Lys Leu Glu Leu Ser Asp Ile Pro Val
785                 790                 795                 800

Arg Ser Leu Val Pro Glu Ala Leu Arg Ser Cys Ser Thr Ala Asp Glu
            805                 810                 815

Tyr Met Gln Lys Leu Pro Ser Phe Asp Gln Asp Trp Ala Arg Glu Ser
        820                 825                 830

Lys Asp Ala Glu Ala Gly Glu Val Leu Arg Tyr Val Gly Val Val
    835                 840                 845

Asp Leu Val Asn Lys Glu Gln Val Glu Leu Arg Arg Tyr Lys Lys
    850                 855                 860

Asp His Pro Phe Ala Gln Leu Ser Gly Ser Asp Asn Ile Ile Ala Phe
865                 870                 875                 880

Thr Thr Ser Arg Tyr Lys Glu Gln Pro Leu Ile Val Arg Gly Pro Gly
            885                 890                 895

Ala Gly Ala Glu Val Thr Ala Gly Gly Val Phe Ser Asp Ile Leu Arg
            900                 905                 910

Leu Ala Ser Tyr Leu Gly Ala Pro Ser
            915                 920

<210> SEQ ID NO 20
<211> LENGTH: 995
<212> TYPE: PRT
<213> ORGANISM: Triticum urartu

<400> SEQUENCE: 20

Met Lys Lys Val Gly Arg Ala Glu Lys Thr Asn Leu Ile Asn Lys Ile
1               5                   10                  15

Leu Pro Ser Tyr Glu Ser Met Val Glu His Pro Val Ser Leu Leu Ser
                20                  25                  30

Ile Arg Cys Met Ile Gly Trp Lys Ser Ser Ile Leu Ser Leu Gln Tyr
            35                  40                  45

Leu Arg Val Ala Pro Ser Arg Lys Thr Phe Asp Leu Phe Met Lys Cys
        50                  55                  60

His Gly Ser Thr Lys Asn Thr Lys Val Lys Asn Tyr Ile Gln Ile Arg
65                  70                  75                  80

Val Pro Ser Asn Asp Asp Tyr Lys His Cys Ser Glu Leu Lys Ala Arg
                85                  90                  95

Arg Arg Tyr Arg Pro Ser Leu Val Ala Gly Glu Val Ser Gln
            100                 105                 110

Cys Leu Lys Cys Glu Ile Asn Gln Asp Arg Pro Met Gly Ala Leu Arg
            115                 120                 125

Ile Gly His Ser Gln Gly Asn Leu Pro Arg His Gly Ser Lys Asn Leu
        130                 135                 140

Leu Thr Pro Ala Ala Ala Ile Ser Val Gln Val Glu Val Ser
145                 150                 155                 160

Thr Tyr Leu Pro Lys Gly Asp Met Trp Ser Val His Lys Phe Gly Gly
                165                 170                 175

Thr Cys Met Gly Thr Pro Gln Arg Ile Gln Asn Val Ala Asp Val Val
            180                 185                 190

Leu Gly Asp Ser Ser Glu Arg Lys Leu Ile Ile Val Ser Ala Met Ser
        195                 200                 205

Lys Val Thr Asp Met Met Tyr Ser Leu Val His Lys Ala Gln Ser Arg
    210                 215                 220

Asp Asp Ser Tyr Thr Glu Glu Leu Asp Lys Val Phe Glu Lys His Met
225                 230                 235                 240
```

```
Ala Ala Ala Lys Asp Leu Leu Asp Gly Glu Asn Leu Ala Arg Phe Leu
            245                 250                 255

Ser Gln Leu His Ser Asp Ile Ser Asn Leu Arg Ala Met Leu Arg Ala
            260                 265                 270

Ile Tyr Ile Ala Gly His Ala Thr Glu Ser Phe Ser Glu Phe Val Val
            275                 280                 285

Gly His Gly Glu Leu Trp Ser Ser Gln Met Leu Ser Tyr Ala Val Gln
            290                 295                 300

Lys Ser Gly Ala Ser Cys Ser Trp Met Asp Thr Arg Glu Val Leu Val
305                 310                 315                 320

Val Lys Pro Ser Gly Pro Asp Met Val Asp Pro Asp Tyr Glu Glu Ser
            325                 330                 335

Glu Lys Arg Leu Glu Lys Trp Phe Ser Arg Gln Pro Ala Glu Ile Ile
            340                 345                 350

Val Ala Thr Gly Phe Ile Ala Ser Thr Ala Glu Asn Ile Pro Thr Thr
            355                 360                 365

Leu Lys Arg Asp Gly Ser Asp Phe Ser Ala Ala Ile Ile Gly Ser Leu
            370                 375                 380

Val Arg Ala Arg Gln Val Thr Ile Trp Thr Asp Val Asp Gly Val Phe
385                 390                 395                 400

Ser Ala Asp Pro Arg Lys Val Ser Glu Ala Val Ile Leu Ser Thr Leu
            405                 410                 415

Ser Tyr Gln Glu Ala Trp Glu Met Ser Tyr Phe Gly Ala Asn Val Leu
            420                 425                 430

His Pro Arg Thr Ile Ile Pro Val Met Lys Asp Asn Ile Pro Ile Val
            435                 440                 445

Ile Arg Asn Met Phe Asn Leu Ser Ala Pro Gly Thr Val Ile Cys Lys
            450                 455                 460

Gln Pro Ala Asn Glu Asp Ala Asp Leu Asp Ala Cys Val Lys Ser Phe
465                 470                 475                 480

Ala Thr Ile Asp Lys Leu Ala Leu Val Asn Val Glu Gly Thr Gly Met
            485                 490                 495

Ala Gly Val Pro Gly Thr Ser Ser Ala Ile Phe Ser Ala Val Lys Glu
            500                 505                 510

Val Gly Ala Asn Val Ile Met Ile Ser Gln Ala Ser Ser Glu His Ser
            515                 520                 525

Ile Cys Phe Ala Val Pro Glu Lys Glu Val Ala Ala Val Ser Ala Ala
530                 535                 540

Leu His Val Arg Phe Arg Glu Ala Leu Ala Ala Gly Arg Leu Ser Lys
545                 550                 555                 560

Val Glu Val Ile His Asp Cys Ser Ile Leu Ala Ala Val Gly Leu Arg
            565                 570                 575

Met Ala Ser Thr Pro Gly Val Ser Ala Ile Leu Phe Asp Ala Leu Ala
            580                 585                 590

Lys Ala Asn Ile Asn Val Arg Ala Ile Ala Gln Gly Cys Ser Glu Tyr
            595                 600                 605

Asn Ile Thr Val Val Leu Lys Gln Glu Asp Cys Val Arg Ala Leu Arg
            610                 615                 620

Ala Ala His Ser Arg Phe Phe Leu Ser Lys Thr Thr Leu Ala Ile Gly
625                 630                 635                 640

Val Ile Gly Pro Gly Leu Ile Gly Ala Thr Leu Leu Asn Gln Leu Arg
            645                 650                 655
```

```
Asp Gln Val Ala Val Leu Lys Glu Asn Met Asn Ile Asp Val Arg Val
            660                 665                 670

Ile Gly Ile Thr Gly Ala Ser Thr Met Leu Ser Asp Thr Gly Val
        675                 680                 685

Asp Leu Thr Arg Trp Lys Glu Glu Met Gln Lys Glu Ala Lys Pro Ala
            690                 695                 700

Asp Leu Ala Asn Phe Val Arg His Leu Ser Glu Asp His Val Phe Pro
705                 710                 715                 720

Asn Lys Val Leu Val Asp Cys Thr Ala Asp Thr Asn Val Ala Ser His
                725                 730                 735

Tyr Tyr Asp Trp Leu Lys Lys Gly Ile His Val Ile Thr Pro Asn Lys
            740                 745                 750

Lys Ala Asn Ser Gly Pro Leu Asp Arg Tyr Leu Lys Leu Arg Thr Leu
        755                 760                 765

Gln Arg Ala Ser Tyr Thr His Tyr Phe Tyr Glu Ala Thr Val Gly Ala
        770                 775                 780

Gly Leu Pro Ile Ile Ser Thr Leu Arg Gly Leu Leu Glu Thr Gly Asp
785                 790                 795                 800

Lys Ile Leu Arg Ile Glu Gly Ile Phe Ser Gly Thr Leu Ser Tyr Ile
            805                 810                 815

Phe Asn Asn Phe Glu Gly Thr Arg Ser Phe Ser Asp Val Val Ala Glu
            820                 825                 830

Ala Lys Glu Ala Gly Tyr Thr Glu Pro Asp Pro Arg Asp Asp Leu Ser
        835                 840                 845

Gly Thr Asp Val Ala Arg Lys Val Ile Ile Leu Ala Arg Glu Ser Gly
850                 855                 860

Leu Arg Leu Glu Leu Ser Asp Ile Pro Val Glu Ser Leu Val Pro Glu
865                 870                 875                 880

Ala Leu Lys Ser Cys Ser Ser Pro Asn Glu Phe Met Gln Lys Leu Pro
            885                 890                 895

Ser Phe Asp Gln Asp Trp Ala Arg Gln Arg His Glu Ala Glu Ala Ala
            900                 905                 910

Gly Glu Val Leu Arg Tyr Val Gly Val Val Asp Val Leu Asn Gly Lys
        915                 920                 925

Gly Arg Val Glu Leu Gln Arg Tyr Lys Arg Asp His Pro Phe Ala Gln
        930                 935                 940

Leu Ser Gly Ser Asp Asn Ile Ile Ala Phe Thr Thr Ser Arg Tyr Lys
945                 950                 955                 960

Glu Gln Pro Leu Ile Val Arg Gly Pro Gly Ala Gly Ala Glu Val Thr
            965                 970                 975

Ala Gly Gly Val Phe Cys Asp Ile Leu Arg Leu Ala Ser Tyr Leu Gly
        980                 985                 990

Ala Pro Ser
    995

<210> SEQ ID NO 21
<211> LENGTH: 922
<212> TYPE: PRT
<213> ORGANISM: Aegilops tauschii

<400> SEQUENCE: 21

Met Ala His Met Phe Ile Val Ser Ser Asn Ser Lys Cys Leu Leu Trp
1               5                   10                  15

Glu His Ala Leu Lys Gly Arg Ile Asn Ser Gln Val Asn Leu Arg Cys
            20                  25                  30
```

-continued

```
Asp Leu Glu Val Val Ser Gln Cys Leu Lys Cys Glu Ile Asn Gln Asp
         35                  40                  45

Arg Pro Met Gly Ala Leu Arg Ile Gly His Ser Gln Gly Asn Leu Pro
 50                  55                  60

Arg His Gly Ser Lys Asn Leu Leu Thr Pro Ala Ala Ala Ile Ser
 65                  70                  75                  80

Val Glu Gln Val Glu Val Ser Thr Tyr Leu Pro Lys Gly Asp Met Trp
                 85                  90                  95

Ser Val His Lys Phe Gly Gly Thr Cys Met Gly Thr Pro Gln Arg Ile
                100                 105                 110

Gln Asn Val Ala Asp Val Val Leu Gly Asp Ser Ser Glu Arg Lys Leu
                115                 120                 125

Ile Ile Val Ser Ala Met Ser Lys Val Thr Asp Met Met Tyr Ser Leu
        130                 135                 140

Val His Lys Ala Gln Ser Arg Asp Asp Ser Tyr Thr Glu Glu Leu Asp
145                 150                 155                 160

Lys Val Phe Glu Lys His Met Ala Ala Lys Asp Leu Leu Asp Gly
                165                 170                 175

Glu Asn Leu Ala Arg Phe Leu Ser Glu Leu His Ser Asp Ile Ser Asn
                180                 185                 190

Leu Arg Ala Met Leu Arg Ala Ile Tyr Ile Ala Gly His Ala Thr Glu
        195                 200                 205

Ser Phe Ser Glu Phe Val Val Gly His Gly Glu Leu Trp Ser Ser Gln
        210                 215                 220

Met Leu Ser Tyr Ala Val Gln Lys Ser Gly Ala Ser Cys Ser Trp Met
225                 230                 235                 240

Asp Thr Arg Glu Val Leu Val Lys Pro Ser Gly Pro Asp Met Val
                245                 250                 255

Asp Pro Asp Tyr Glu Glu Ser Glu Lys Arg Leu Glu Lys Trp Phe Ser
                260                 265                 270

Arg Gln Pro Ala Glu Ile Ile Val Ala Thr Gly Phe Ile Ala Ser Thr
        275                 280                 285

Ala Glu Asn Ile Pro Thr Thr Leu Lys Arg Asp Gly Ser Asp Phe Ser
        290                 295                 300

Ala Ala Ile Ile Gly Ser Leu Val Arg Ala Arg Gln Val Thr Ile Trp
305                 310                 315                 320

Thr Asp Val Asp Gly Val Phe Ser Ala Asp Pro Arg Lys Val Ser Glu
                325                 330                 335

Ala Val Ile Leu Ser Thr Leu Ser Tyr Gln Glu Ala Trp Glu Met Ser
                340                 345                 350

Tyr Phe Gly Ala Asn Val Leu His Pro Arg Thr Ile Ile Pro Val Met
        355                 360                 365

Lys Asp Asn Ile Pro Ile Val Ile Arg Asn Met Phe Asn Leu Ser Ala
        370                 375                 380

Pro Gly Thr Val Ile Cys Lys Gln Pro Ala Asn Glu Ala Asp Leu
385                 390                 395                 400

Asp Ala Cys Val Lys Ser Phe Ala Thr Ile Asp Lys Leu Ala Leu Val
                405                 410                 415

Asn Val Glu Gly Thr Gly Met Ala Gly Val Pro Gly Thr Ser Ser Ala
                420                 425                 430

Ile Phe Ser Ala Val Lys Glu Val Gly Ala Asn Val Ile Met Ile Ser
        435                 440                 445
```

```
Gln Ala Ser Ser Glu His Ser Ile Cys Phe Ala Val Pro Glu Lys Glu
450                 455                 460
Val Ala Ala Val Ser Ala Ala Leu His Val Arg Phe Arg Glu Ala Leu
465                 470                 475                 480
Ala Ala Gly Arg Leu Ser Lys Val Glu Val Ile His Asp Cys Ser Ile
            485                 490                 495
Leu Ala Ala Val Gly Leu Arg Met Ala Ser Thr Pro Gly Val Ser Ala
            500                 505                 510
Ile Leu Phe Asp Ala Leu Ala Lys Ala Asn Ile Asn Val Arg Ala Ile
        515                 520                 525
Ala Gln Gly Cys Ser Glu Tyr Asn Ile Thr Val Val Leu Lys Gln Glu
530                 535                 540
Asp Cys Val Arg Ala Leu Arg Ala Ala His Ser Arg Phe Phe Leu Ser
545                 550                 555                 560
Lys Thr Thr Leu Ala Ile Gly Val Ile Gly Pro Gly Leu Ile Gly Ala
                565                 570                 575
Thr Leu Leu Asn Gln Leu Arg Asp Gln Val Ala Ile Leu Lys Glu Asn
            580                 585                 590
Met Asn Ile Asp Val Arg Val Ile Gly Ile Thr Gly Ala Ser Thr Met
        595                 600                 605
Leu Leu Ser Glu Thr Gly Val Asp Leu Thr Arg Trp Lys Glu Glu Met
610                 615                 620
Gln Lys Glu Ala Lys Pro Ala Asp Leu Ala Asn Phe Val Arg His Leu
625                 630                 635                 640
Ser Glu Asp His Val Phe Pro Asn Lys Val Leu Val Asp Cys Thr Ala
                645                 650                 655
Asp Thr Asn Val Ala Ser His Tyr Tyr Asp Trp Leu Lys Lys Gly Ile
            660                 665                 670
His Val Ile Thr Pro Asn Lys Lys Ala Asn Ser Gly Pro Leu Asp Arg
        675                 680                 685
Tyr Leu Lys Leu Arg Thr Leu Gln Arg Ala Ser Tyr Thr His Tyr Phe
690                 695                 700
Tyr Glu Ala Thr Val Gly Ala Gly Leu Pro Ile Ile Ser Thr Leu Arg
705                 710                 715                 720
Gly Leu Leu Glu Thr Gly Asp Lys Ile Leu Arg Ile Glu Gly Ile Phe
                725                 730                 735
Ser Gly Thr Leu Ser Tyr Ile Phe Asn Asn Phe Glu Gly Thr Arg Ser
            740                 745                 750
Phe Ser Asp Val Val Ala Glu Ala Lys Glu Ala Gly Tyr Thr Glu Pro
        755                 760                 765
Asp Pro Arg Asp Asp Leu Ser Gly Thr Asp Val Ala Arg Lys Val Ile
770                 775                 780
Ile Leu Ala Arg Glu Ser Gly Leu Arg Leu Glu Leu Ser Asp Ile Pro
785                 790                 795                 800
Val Glu Ser Leu Val Pro Glu Ala Leu Lys Ser Cys Ser Ser Pro Asn
                805                 810                 815
Glu Phe Met Gln Lys Leu Pro Ser Phe Asp Gln Asp Trp Ala Arg Gln
            820                 825                 830
Arg His Glu Ala Glu Ala Gly Glu Val Leu Arg Tyr Val Gly Ala
        835                 840                 845
Val Asp Val Leu Asn Gly Lys Gly Arg Val Glu Leu Gln Arg Tyr Lys
850                 855                 860
Arg Asp His Pro Phe Ala Gln Leu Ser Gly Ser Asp Asn Ile Ile Ala
```

```
                865                 870                 875                 880
          Phe Thr Thr Ser Arg Tyr Lys Glu Gln Pro Leu Ile Val Arg Gly Pro
                          885                 890                 895
          Gly Ala Gly Ala Glu Val Thr Ala Gly Gly Val Phe Cys Asp Ile Leu
                          900                 905                 910
          Arg Leu Ala Ser Tyr Leu Gly Ala Pro Ser
                          915                 920
```

<210> SEQ ID NO 22
<211> LENGTH: 4788
<212> TYPE: DNA
<213> ORGANISM: Artificial
<220> FEATURE:
<223> OTHER INFORMATION: construct of pBIOS10221

<400> SEQUENCE: 22

```
agatctcgac ctactcgatc taatacatgt tgacagcaag ctgaggatcg ggacatgtaa      60
taaggagtta ggagatgtgg tatggtacta aatgcaaggt caaaattcga tgcttttttcc   120
gtgctcaact attaactagt attattacct aattttttact tgtgatgaca actaatgcat   180
cgagccacaa ttcagtaaat acttacatta atttaagcat atgtatagta tatacatttc   240
caattcttct tttttgtgtg gagatccacg acgatgcaag ttgctcctcc caacccaaat   300
ccacctctct cttaaatccg cgtatcttca ccaccaccag ctgctacaca tcgtattgtc   360
caaatctgtg tcggcttgac ccagtgatgt gcgcgctaga tttggcagcg cctgaatgca   420
gtgcagccac ctgtatggta cccttggtag agtaacaaca cccttatccc tacggcagcc   480
atgtatgacc cttatcccta cggcagccat gtataccaat acctttcttt gaaccacaaa   540
attatagtcc atatccttaa ccacaagttc attttttgtt tcccggtctc ctaaggaaat   600
taagttctgt ttccacaatt tacatggata taggacatct atgttcctaa cattaacatt   660
actggataac aggcaccctc tcctccacac cctgcaaagc cttcctccag cgccatgcat   720
cctccgttgc taacagacac ctctctccac atcgcgtgca agcaaacctc caaattctac   780
cgatccccag aatccggcct tgactgcaaa cagacacccc tctccccatc ctgcaaaccc   840
atcagccaac cgaataacac aagaaggcag gtgagcagtg acaaagcacg tcaacagcag   900
caaagccaag ccaaaaacga tccaggagca aggtgcggcc gcagctctcc cggtcccctt   960
tgcggttacc actagctaag aatgaagatg gtactctaaa tgcatacttg cgcggttttt  1020
ctctagtcta acttaataaa ctaaataaac aatttctttc ttattttttt aatttagttc  1080
gtttagttag actagagaag aaccacgagg agttatttga agcatcgtcc ccatccttac  1140
cactagctag cactagcaga caccctctc cacgtcctgc aaacaggcaa tattagccag  1200
cggaataaca caagcaggca agtgcgcagt gacaaagtac gtccacagca gcgatcccag  1260
ccaaaagcag cgtagccaca gccgcgcgca gctctcggct acccttaccg ccgatcacat  1320
gcatgccttt ccaatcccgc gtgcacacgc cgaccacaca ctcgccaact ccccatccct  1380
atttgaagcc accggccggc gccctgcatt gatcaatcaa ctcgcagcag aggagcagca  1440
cgagcaacac gccgcgccgc gctccaacca tctccagctt cgttcgcgct tcccggccca  1500
ctccccggcc gccgccgtct ccaccatggc tcgtagtctc gctgtcgcca gcccactccc  1560
accggcggca gcggtcaggc gccgtccacg ggcatcggcc tccggacggg aggtcatcag  1620
ccagtgctgg aagtgcgaga tcaaccagga tcaaccactt ggcaatagcc tcagaattgg  1680
gcactctcaa gggtcactcc aacgccacgg cagtaggaac ttgctcgcgg ccgcggccgc  1740
```

```
tatctccatt gagcaagctg aggtttccac ctatttgcca aagggtgaca tgtggtccgt    1800
gcacaagttc gggggaactt gcatgggcac cccgcaacgc atccagaacg tggccgacat    1860
tgtcctcggc gatagctctg aaaggaagct cattatcgtc tcagctatgt ccaaggtgac    1920
ggacatgatg tttaacctcg ttcataaggc ccaatcgcgg gataactcct atgtcacagc    1980
actggacgag gtgttcaaca agcacatggc cgccgcaaag gaactcctcg atggggaaga    2040
cctcgccaga ttcctcgctc agttgcactc cgacatctcg aacctccggg ccatgttgag    2100
ggctatcttc attgccggac atgccaccga gtctttttcc gatttcgtgg tggggcatgg    2160
cgagctctgg tcagcgcaga tgctctccta cgctattaag aagtcgggcg tcccctgcag    2220
ctggatggac acgagggagg tgctggtggt gaagccatct ggaagtaatc aggtggaccc    2280
agattacctg gagtcagaga gcggctgcag aagtggtttt tcacgccagc ctgccgagat    2340
catcatcgct actggcttta tcgcgtcgac cgctgaaaac attccaacga ccctgaagcg    2400
cgacgggtct gacttcagtg catccatcat cggctcactt gttcgggcct gtcaggttac    2460
aatctggacc gacgtggatg cgtcttctc ggcagaccca cggaaggtca gtgaggctgt    2520
tatcttgagc acgctctcct accaagaagc atgggaaatg tcctactttg gtgccaacgt    2580
gctccatccc cggaccatca tcccagttat gaaggacaac atcccattg tcatcaggaa    2640 catgttcaat ctttcggcac cgggcaccac catttgcaag caaccagcaa acgagaatgc    2700
tgatctcgac gcctgtgtta agtctttcgc tacaatcgat aagcttgcac tggtgaatgt    2760
cgagggcacc ggcatggccg ggtccctgg caccgccagc gccatcttct ctgcagctaa    2820
ggatgtcgga gccaacgtga ttatgatttc tcaagccagt tcggagcact ccgtttgctt    2880
tgcggtgcca gagaaggagg ttgcggctgt cagcaccgcc ttgcacgtca ggttccggga    2940
ggccctcgcg gccggtagac tgtccaaggt cgaggtcatt cggggctgct cgatcctcgc    3000
cgccgtcggg ctgaggatgg cttctacccc aggcgtctcg gcgatcctgt tcgatgcctt    3060
ggcaaaggct aatatcaacg tgcgggcgat cgcgcaaggc tgctccgagt acaatatcac    3120
cgtggtgctc aagcaagagg actgtgttcg cgccctccgg gctgttcact caagattctt    3180
tctcagtaag acgaccctgg ccgtgggcat catcggcccc gggctcattg ggggaaccct    3240
cctggatcaa ctgaaggacc aggccgccgt gcttaaggag aacatgaata tcgatctgcg    3300
cgtgatcggc atctctggat cccgcacgat gcacctctcg gacatcggag tcgacctcaa    3360
tcagtggaag gagctgctca gaaaggaagc cgagccggcc gatctggact cgtttgtgcg    3420
tcatctgtcc gagaaccacg tgttcccaaa taaggtgctc gtggactgca ctgccgatac    3480
ctacgtggca tgccactact atgactggct gaagaagggc atccacgtta tcaccccaa    3540 caagaaggct aactccggcc cacttgatcg ctacctcaag ctccgtactc ttcaaagggc    3600
ttcttacaca cactacttct acgaggcgac cgtgggagcc gggctcccta tcatctccac    3660
cctccgcggc ctgctggaga ctggggacaa gatcctgcgg attgagggta tctttccgg    3720 taccctctcc tacatttta acaacttcga gggcacccgg acattctcta acgtggtggc    3780
cgaggcgaag gaggctggct acaccgagcc agacccacgc gacgacttgt cgggtacaga    3840 tgtgcgcgt aaggttatca tcttggcgcg cgagtctggt cttcgcctcg agctctcgga    3900
tattcctgtt aagagccttg tcccagaggc cctgaggagt tgcagttccg ccgacgaatt    3960
catgcagaag ttgccgtctt ttgaccaaga ctgggaccgc cagagggatg aagccgaggc    4020
cgccggagag gtgctccgct acgtcggcgt ggtggacgtc gccaacagga agggccgtgt    4080
tgaacttcaa cggtacaagc gcgatcatcc atttgcgcaa cttttcgggta gcgataatat    4140
```

| | |
|---|---|
| catcgccttt accacctcga gatacaagga gcaaccccttg atcgttagag gaccaggagc | 4200 |
| tggtgccgaa gttaccgcgg ggggagtctt ctgcgacatt ctgcgcctcg cgtcgtatct | 4260 |
| gggcgcaccg agttaaaacc taaatgctct taactgagct aattatgtaa tgcacataca | 4320 |
| catatttaca tagatatgca tatttatata tagcatgtat attgtactac atgcattgct | 4380 |
| tcttaataca tgtagtaaag atatatgcaa aaatagtcga aagatttgtt tacatataaa | 4440 |
| atcaccaata tttattgtta ttgtatttc atgaataaag taataagatt atttgtctaa | 4500 |
| tattttgatt tactagtact agaaatgaaa aggaatatgc acaatttcag cattatagtt | 4560 |
| tggtaggcaa aatggagtga gaatagagtt tcatagtata tactaaggtt cttaattgtg | 4620 |
| caaatagttg atacaagtca catgggccaa gtttgtaaat cttaaatcga aatatgcctt | 4680 |
| cttctttttt tgcatgaaaa tgctagtaat ttataagtgt gttttttcaat aagagatgct | 4740 |
| aaataccaaa attaacctag ttttcagtga gcgcttgcat tattgtgg | 4788 |

<210> SEQ ID NO 23
<211> LENGTH: 1517
<212> TYPE: DNA
<213> ORGANISM: Artificial
<220> FEATURE:
<223> OTHER INFORMATION: sorghum promoter SvPEPc_C4

<400> SEQUENCE: 23

| | |
|---|---|
| agatctcgac ctactcgatc taatacatgt tgacagcaag ctgaggatcg ggacatgtaa | 60 |
| taaggagtta ggagatgtgg tatggtacta aatgcaaggt caaaattcga tgcttttttcc | 120 |
| gtgctcaact attaactagt attattaccct aattttttact tgtgatgaca actaatgcat | 180 |
| cgagccacaa ttcagtaaat acttacatta atttaagcat atgtatagta tatacatttc | 240 |
| caattcttct tttttgtgtg gagatccacg acgatgcaag ttgctcctcc caacccaaat | 300 |
| ccacctctct cttaaatccg cgtatcttca ccaccaccag ctgctacaca tcgtattgtc | 360 |
| caaatctgtg tcggcttgac ccagtgatgt gcgcgctaga tttggcagcg cctgaatgca | 420 |
| gtgcagccac ctgtatggta cccttggtag agtaacaaca ccctattccc tacggcagcc | 480 |
| atgtatgacc cttatcccta cggcagccat gtataccaat acctttctt gaaccacaaa | 540 |
| attatagtcc atatccttaa ccacaagttc atttttttgtt tcccggtctc ctaaggaaat | 600 |
| taagttctgt ttccacaatt tacatggata taggacatct atgttcctaa cattaacatt | 660 |
| actggataac aggcaccctc tcctccacac cctgcaaagc cttcctccag cgccatgcat | 720 |
| cctccgttgc taacagacac ctctctccac atcgcgtgca agcaaacctc caaattctac | 780 |
| cgatccccag aatccggcct tgactgcaaa cagacacccc tctccccatc ctgcaaaccc | 840 |
| atcagccaac cgaataacac aagaaggcag gtgagcagtg acaaagcacg tcaacagcag | 900 |
| caaagccaag ccaaaaacga tccaggagca aggtgcggcc gcagctctcc cggtcccctt | 960 |
| tgcggttacc actagctaag aatgaagatg gtactctaaa tgcatacttg cgcggttttt | 1020 |
| ctctagtcta acttaataaa ctaaataaac aatttctttc ttattttttt aatttagttc | 1080 |
| gtttagttag actagagaag aaccacgagg agttatttga agcatcgtcc ccatccttac | 1140 |
| cactagctag cactagcaga caccccctctc cacgtcctgc aaacaggcaa tattagccag | 1200 |
| cggaataaca caagcaggca agtgcgcagt gacaaagtac gtccacagca gcgatcccag | 1260 |
| ccaaaagcag cgtagccaca gccgcgcgca gctctcggct accccttaccg ccgatcacat | 1320 |
| gcatgccttt ccaatcccgc gtgcacacgc cgaccacaca ctcgccaact ccccatccct | 1380 |

```
atttgaagcc accggccggc gccctgcatt gatcaatcaa ctcgcagcag aggagcagca    1440
cgagcaacac gccgcgccgc gctccaacca tctccagctt cgttcgcgct tcccggccca    1500
ctccccggcc gccgccg                                                   1517

<210> SEQ ID NO 24
<211> LENGTH: 509
<212> TYPE: DNA
<213> ORGANISM: Artificial
<220> FEATURE:
<223> OTHER INFORMATION: terAtSac66

<400> SEQUENCE: 24
ctaaatgctc ttaactgagc taattatgta atgcacatac acatatttac atagatatgc      60
atatttatat atagcatgta tattgtacta catgcattgc ttcttaatac atgtagtaaa     120
gatatatgca aaatagtcg  aaagatttgt ttacatataa aatcaccaat atttattgtt     180
attgtatttt catgaataaa gtaataagat tatttgtcta atattttgat ttactagtac     240
tagaaatgaa aaggaatatg cacaatttca gcattatagt ttggtaggca aaatggagtg     300
agaatagagt ttcatagtat atactaaggt tcttaattgt gcaaatagtt gatacaagtc     360
acatgggcca agtttgtaaa tcttaaatcg aaatatgcct tcttcttttt ttgcatgaaa     420
atgctagtaa tttataagtg tgtttttcaa taagagatgc taaataccaa aattaaccta     480
gttttcagtg agcgcttgca ttattgtgg                                       509

<210> SEQ ID NO 25
<211> LENGTH: 4676
<212> TYPE: DNA
<213> ORGANISM: Artificial
<220> FEATURE:
<223> OTHER INFORMATION: Construct of pBIOS10227

<400> SEQUENCE: 25
tcgaggtcat tcatatgctt gagaagagag tcgggatagt ccaaaataaa acaaaggtaa      60
gattacctgg tcaaaagtga aaacatcagt taaaaggtgg tataaagtaa aatatcggta     120
ataaaaggtg gcccaaagtg aaatttactc ttttctacta ttataaaaat tgaggatgtt     180
tttgtcggta ctttgatacg tcattttgt atgaattggt ttttaagttt attcgctttt      240
ggaaatgcat atctgtattt gagtcgggtt ttaagttcgt ttgcttttgt aaatacagag     300
ggatttgtat aagaaatatc tttaaaaaaa cccatatgct aatttgacat aattttttgag    360 aaaaatatat attcaggcga attctcacaa tgaacaataa taagattaaa atagctttcc     420
cccgttgcag cgcatgggta ttttttctag taaaaataaa agataaactt agactcaaaa     480
catttacaaa aacaacccct aaagttccta aagcccaaag tgctatccac gatccatagc     540
aagcccagcc caacccaacc caacccaacc caccccagtc cagccaactg gacaatagtc     600
tccacacccc cccactatca ccgtgagttg tccgcacgca ccgcacgtct cgcagccaaa     660
aaaaaaaaaa gaaagaaaaa aaagaaaaag aaaaacagc  aggtgggtcc gggtcgtggg    720
ggccggaaac gcgaggagga tcgcgagcca gcgacgaggc cggccctccc tccgcttcca     780
aagaaacgcc cccatcgcc  actatataca tacccccccc tctcctccca tcccccaac     840 cctaccacca ccaccaccac cacctccacc tcctccccc  tcgctgccgg acgacgagct    900 catccccccct cccctcccgc cgccgccgcg ccggtaacca cccgcccct  atcctctttc    960 tttctccgtt ttttttttcc gtctcggtct cgatctttgg ccttggtagt ttgggtgggc    1020
gagaggcggc ttcgtgcgcg cccagatcgg tgcgcggag  gggcgggatc tcgcggctgg   1080
```

```
ggctctcgcc ggcgtggatc cggcccggat ctcgcgggga atgggctct cggatgtaga    1140
tctgcgatcc gccgttgttg ggggagatga tggggggttt aaaatttccg ccatgctaaa    1200
caagatcagg aagagggaa aagggcacta tggtttatat ttttatatat ttctgctgct    1260
tcgtcaggct tagatgtgct agatctttct ttcttctttt tgtgggtaga atttgaatcc    1320
ctcagcattg ttcatcggta gttttctttt tcatgatttg tgacaaatgc agcctcgtgc    1380
ggagcttttt tgtaggtaga cgatatctcc accatggctc gtagtctcgc tgtcgccagc    1440
ccactcccac cggcggcagc ggtcaggcgc cgtccacggg catcggcctc cggacgggag    1500
gtcatcagcc agtgctggaa gtgcgagatc aaccaggatc aaccacttgg caatagcctc    1560
agaattgggc actctcaagg gtcactccaa cgccacggca gtaggaactt gctcgcggcc    1620
gcggccgcta tctccattga gcaagctgag gtttccacct atttgccaaa gggtgacatg    1680
tggtccgtgc acaagttcgg gggaacttgc atgggcaccc cgcaacgcat ccagaacgtg    1740
gccgacattg tcctcggcga tagctctgaa aggaagctca ttatcgtctc agctatgtcc    1800
aaggtgacgg acatgatgtt taacctcgtt cataaggccc aatcgcggga taactcctat    1860
gtcacagcac tggacgaggt gttcaacaag cacatggccg ccgcaaagga actcctcgat    1920
ggggaagacc tcgccagatt cctcgctcag ttgcactccg acatctcgaa cctccgggcc    1980
atgttgaggg ctatcttcat tgccggacat gccaccgagt cttttcccga tttcgtggtg    2040
gggcatggcg agctctggtc agcgcagatg ctctcctacg ctattaagaa gtcgggcgtc    2100
ccctgcagct ggatggacac gagggaggtg ctggtggtga agccatctgg aagtaatcag    2160
gtggacccag attacctgga gtcagagaag cggctgcaga agtggttttc acgccagcct    2220
gccgagatca tcatcgctac tggctttatc gcgtcgaccg ctgaaaacat tccaacgacc    2280
ctgaagcgcg acgggtctga cttcagtgca tccatcatcg gctcacttgt tcgggcctgt    2340
caggttacaa tctggaccga cgtggatggc gtcttctcgg cagacccacg gaaggtcagt    2400
gaggctgtta tcttgagcac gctctcctac caagaagcat gggaaatgtc ctactttggt    2460
gccaacgtgc tccatccccg gaccatcatc ccagttatga aggacaacat ccccattgtc    2520
atcaggaaca tgttcaatct ttcggcaccg ggcaccacca tttgcaagca accagcaaac    2580
gagaatgctg atctcgacgc ctgtgttaag tctttcgcta caatcgataa gcttgcactg    2640
gtgaatgtcg agggcaccgg catggccggg gtccctggca ccgccagcgc catcttctct    2700
gcagctaagg atgtcggagc caacgtgatt atgatttctc aagccagttc ggagcactcc    2760
gtttgctttg cggtgccaga aaggaggtt gcggctgtca gcaccgcctt gcacgtcagg    2820
ttccgggagg ccctcgcggc cggtagactg tccaaggtcg aggtcattcg gggctgctcg    2880
atcctcgccg ccgtcgggct gaggatggct tctaccccag gcgtctcggc gatcctgttc    2940
gatgccttgg caaaggctaa tatcaacgtg cgggcgatcg cgcaaggctg ctccgagtac    3000
aatatcaccg tggtgctcaa gcaagaggac tgtgttcgcg ccctccggc tgttcactca    3060
agattctttc tcagtaagac gaccctggcc gtgggcatca tcggccccgg gctcattggg    3120
ggaaccctcc tggatcaact gaaggaccag gccgccgtgc ttaaggagaa catgaatatc    3180
gatctgcgcg tgatcggcat ctctggatcc cgcacgatgc acctctcgga catcggagtc    3240
gacctcaatc agtggaagga gctgctcaga aaggaagccg agccggccga tctggactcg    3300
tttgtgcgtc atctgtccga gaaccacgtg ttcccaaata aggtgctcgt ggactgcact    3360
gccgatacct acgtggcatg ccactactat gactggctga agaagggcat ccacgttatc    3420
```

| | |
|---|---|
| accccccaaca agaaggctaa ctccggccca cttgatcgct acctcaagct ccgtactctt | 3480 |
| caaagggctt cttacacaca ctacttctac gaggcgaccg tgggagccgg gctccctatc | 3540 |
| atctccaccc tccgcggcct gctggagact ggggacaaga tcctgcggat tgagggtatc | 3600 |
| ttttccggta ccctctccta cattttaac aacttcgagg gcacccggac attctctaac | 3660 |
| gtggtggccg aggcgaagga ggctggctac accgagccag acccacgcga cgacttgtcg | 3720 |
| ggtacagatg tggcgcgtaa ggttatcatc ttggcgcgcg agtctggtct tcgcctcgag | 3780 |
| ctctcggata ttcctgttaa gagccttgtc ccagaggccc tgaggagttg cagttccgcc | 3840 |
| gacgaattca tgcagaagtt gccgtctttt gaccaagact gggaccgcca gagggatgaa | 3900 |
| gccgaggccg ccggagaggt gctccgctac gtcggcgtgg tggacgtcgc caacaggaag | 3960 |
| ggccgtgttg aacttcaacg gtacaagcgc gatcatccat ttgcgcaact ttcgggtagc | 4020 |
| gataatatca tcgcctttac cacctcgaga tacaaggagc aacccttgat cgttagagga | 4080 |
| ccaggagctg gtgccgaagt taccgcgggg ggagtcttct gcgacattct gcgcctcgcg | 4140 |
| tcgtatctgg gcgcaccgag ttaaaaccta aatgctctta actgagctaa ttatgtaatg | 4200 |
| cacatacaca tatttacata gatatgcata tttatatata gcatgtatat tgtactacat | 4260 |
| gcattgcttc ttaatacatg tagtaaagat atatgcaaaa atagtcgaaa gatttgttta | 4320 |
| catataaaat caccaatatt tattgttatt gtattttcat gaataaagta ataagattat | 4380 |
| ttgtctaata ttttgattta ctagtactag aaatgaaaag gaatatgcac aatttcagca | 4440 |
| ttatagtttg gtaggcaaaa tggagtgaga atagagtttc atagtatata ctaaggttct | 4500 |
| taattgtgca aatagttgat acaagtcaca tgggccaagt tgtaaatct taaatcgaaa | 4560 |
| tatgccttct tcttttttg catgaaaatg ctagtaattt ataagtgtgt ttttcaataa | 4620 |
| gagatgctaa ataccaaaat taacctagtt ttcagtgagc gcttgcatta ttgtgg | 4676 |

<210> SEQ ID NO 26
<211> LENGTH: 1395
<212> TYPE: DNA
<213> ORGANISM: Artificial
<220> FEATURE:
<223> OTHER INFORMATION: modified proOsActin

<400> SEQUENCE: 26

| | |
|---|---|
| tcgaggtcat tcatatgctt gagaagagag tcgggatagt ccaaaataaa acaaaggtaa | 60 |
| gattacctgg tcaaaagtga aaacatcagt taaaaggtgg tataaagtaa aatatcggta | 120 |
| ataaaaggtg gcccaaagtg aaatttactc ttttctacta ttataaaaat tgaggatgtt | 180 |
| tttgtcggta ctttgatacg tcattttgt atgaattggt ttttaagttt attcgctttt | 240 |
| ggaaatgcat atctgtattt gagtcgggtt ttaagttcgt ttgcttttgt aaatacagag | 300 |
| ggatttgtat aagaaatatc tttaaaaaaa cccatatgct aatttgacat aattttgag | 360 |
| aaaaatatat attcaggcga attctcacaa tgaacaataa taagattaaa atagctttcc | 420 |
| cccgttgcag cgcatgggta ttttttctag taaaaataaa agataaactt agactcaaaa | 480 |
| catttacaaa aacaacccct aaagttccta agcccaaag tgctatccac gatccatagc | 540 |
| aagcccagcc caacccaacc caacccaacc caccccagtc cagccaactg gacaatagtc | 600 |
| tccacacccc cccactatca ccgtgagttg tccgcacgca ccgcacgtct cgcagccaaa | 660 |
| aaaaaaaaaa gaaagaaaaa aagaaaaaag aaaaacagc aggtgggtcc gggtcgtggg | 720 |
| ggccggaaac gcgaggagga tcgcgagcca gcgacgaggc cggccctccc tccgcttcca | 780 |
| aagaaacgcc ccccatcgcc actatataca taccccccccc tctcctccca tccccccaac | 840 |

```
cctaccacca ccaccaccac cacctccacc tcctccccccc tcgctgccgg acgacgagct      900 catccccct ccccctccgc cgccgccgcg ccggtaacca ccccgcccct atcctctttc        960
tttctccgtt ttttttttcc gtctcggtct cgatctttgg ccttggtagt ttgggtgggc      1020
gagaggcggc ttcgtgcgcg cccagatcgg tgcgcgggag gggcgggatc tcgcggctgg      1080
ggctctcgcc ggcgtggatc cggcccggat ctcgcgggga atgggctct cggatgtaga       1140 tctgcgatcc gccgttgttg ggggagatga tgggggtttt aaaatttccg ccatgctaaa      1200
caagatcagg aagaggggaa aagggcacta tggtttatat ttttatatat ttctgctgct     1260
tcgtcaggct tagatgtgct agatctttct ttcttctttt tgtgggtaga atttgaatcc      1320
ctcagcattg ttcatcggta gttttttcttt tcatgatttg tgacaaatgc agcctcgtgc    1380
ggagcttttt tgtag                                                       1395
```

<210> SEQ ID NO 27
<211> LENGTH: 4358
<212> TYPE: DNA
<213> ORGANISM: Artificial
<220> FEATURE:
<223> OTHER INFORMATION: Construct of pBIOS10233

<400> SEQUENCE: 27

```
tcgaggtcat tcatatgctt gagaagagag tcgggatagt ccaaaataaa acaaaggtaa        60
gattacctgg tcaaaagtga aaacatcagt taaaaggtgg tataaagtaa aatatcggta       120
ataaaaggtg gcccaaagtg aaatttactc ttttctacta ttataaaaat tgaggatgtt      180
tttgtcggta ctttgatacg tcattttttgt atgaattggt ttttaagttt attcgctttt     240
ggaaatgcat atctgtattt gagtcgggtt ttaagttcgt ttgcttttgt aaatacagag      300
ggatttgtat aagaaatatc tttaaaaaaa cccatatgct aatttgacat aattttttgag     360 aaaaatatat attcaggcga attctcacaa tgaacaataa taagattaaa atagctttcc    420
cccgttgcag cgcatgggta ttttttctag taaaaataaa agataaactt agactcaaaa      480
catttacaaa aacaaccccct aaagttccta aagcccaaag tgctatccac gatccatagc     540
aagcccagcc caacccaacc caacccaacc caccccagtc cagccaactg gacaatagtc     600
tccacacccc cccactatca ccgtgagttg tccgcacgca ccgcacgtct cgcagccaaa     660
aaaaaaaaaa gaaagaaaaa aaagaaaaag aaaaacagc aggtgggtcc gggtcgtggg      720
ggccggaaac gcgaggagga tcgcgagcca gcgacgaggc cggccctccc tccgcttcca    780
aagaaacgcc cccatcgcc actatataca tacccccccc tctcctccca tcccccaac    840 cctaccacca ccaccaccac cacctccacc tcctccccccc tcgctgccgg acgacgagct    900 catccccct ccccctccgc cgccgccgcg ccggtaacca ccccgcccct atcctctttc     960
tttctccgtt ttttttttcc gtctcggtct cgatctttgg ccttggtagt ttgggtgggc   1020
gagaggcggc ttcgtgcgcg cccagatcgg tgcgcgggag gggcgggatc tcgcggctgg   1080
ggctctcgcc ggcgtggatc cggcccggat ctcgcgggga atgggctct cggatgtaga    1140 tctgcgatcc gccgttgttg ggggagatga tgggggtttt aaaatttccg ccatgctaaa   1200
caagatcagg aagaggggaa aagggcacta tggtttatat ttttatatat ttctgctgct   1260
tcgtcaggct tagatgtgct agatctttct ttcttctttt tgtgggtaga atttgaatcc   1320
ctcagcattg ttcatcggta gttttttcttt tcatgatttg tgacaaatgc agcctcgtgc 1380
ggagcttttt tgtaggtaga cgatatctcc accatgtccg ttatcgctca agctgggcc    1440
```

-continued

```
aagggcaggc aactccacaa gttcggcggc tcctcgctcg ctgatgtcaa gtgctacctc    1500
agagtggctg ggatcatggc ggagtacagc caaccggacg acatgatggt ggtttctgcg    1560
gcgggctcga cgaccaacca actgatcaac tggctgaagc tgagccaaac cgatcgcctc    1620
agcgcgcatc aggtgcaaca aaccctcagg agataccagt gcgatctcat ctctgggctc    1680
ctgccggctg aggaggcgga ctccctgatc tccgcgttcg tgtcggacct ggagaggctg    1740
gccgctctcc tggattcagg catcaacgac gcggtgtacg ctgaggtcgt cgggcatggc    1800
gaggtctgga gcgcgagact gatgtctgcc gttctgaacc agcaaggcct cccagccgcg    1860
tggctggatg cgcgggagtt cctgagggcc gagcgcgcgg cccagccaca ggtcgacgag    1920
ggcctgtcat accctctgct ccaacaactg ctcgtgcaac acccaggcaa gcgcctcgtt    1980
gtcaccgggt tcatcagccg gaacaacgct ggggagaccg tgctcctcgg gaggaacggg    2040
agcgactaca gcgccacgca aatcggggct ctggccgggg tttccagagt tacgatctgg    2100
tcagatgttg ccggcgtcta cagcgccgac ccaaggaagg ttaaggatgc ttgcctcctc    2160
ccgctgctgc gcctcgacga ggcttcagag ctcgcgcgcc tcgctgcccc agtgctgcat    2220
gcgcggacgc tgcaaccagt gtcgggcagc gagatcgatc tgcaactgcg gtgcagctac    2280
acgcccgatc aggggtccac cagaatcgag agggtgctgg cctccggcac cggggcgagg    2340
atcgtgacgt cgcacgatga tgtgtgcctc atcgagttcc aagttccaac cagccaagac    2400
ttcaagctgg cccacaagga gatcgaccag atcctgaaga gagcccaagt gaggccactc    2460
gctgttggcg tccacaacga taggcagctg ctccagttct gctacacgag cgaggtcgcg    2520
gattccgccc tcaagatcct cgatgaggcg ggcctcccag gggagctcag actgcgccaa    2580
ggcctcgctc tggtggcgat ggtcggggcg ggcgtgacca gaaacccact ccattgccac    2640
agattctggc aacagctcaa ggggcaaccg gttgagttca cctggcaaag cgacgacggc    2700
atctccctgg ttgccgttct gcgcacgggc ccaaccgagt cactcatcca agggctccac    2760
caatccgttt tcagagcgga gaagagaatc ggcctggtcc tgttcggcaa ggggaacatc    2820
gggtctaggt ggctggagct gttcgctagg gagcaatcta ccctctcggc ccgcaccggg    2880
ttcgagttcg ttctcgccgg ggtggtggat agccggagat ccctgctctc ctacgatggg    2940
ctcgacgcct ctagggctct ggcgttcttc aacgacgagg ccgttgagca agacgaggag    3000
tcactcttcc tgtggatgag agctcaccca tacgatgacc tcgttgtcct ggacgtgacg    3060
gcctcccaac agctcgcgga ccaataccctc gatttcgcct cgcatgggtt ccacgtcatc    3120
agcgctaaca agctggctgg ggcgtcagac tcgaacaagt accgccaaat ccatgacgct    3180
ttcgagaaga cgggcaggca ctggctctac aacgccacgg tgggcgcggg gctcccgatc    3240
aaccacacgg ttagagacct catcgattcc ggcgacacga tcctctctat cagcggcatc    3300
ttctcaggga ccctctcatg gctgttcctc cagttcgatg ggtccgttcc gttcaccgag    3360
ctggtggacc aagcttggca gcaagggctc accgagccgg atccaagaga tgacctgtcc    3420
gggaaggatg tcatgcggaa gctcgtgatc ctggctagaa aggctgggta caacatcgag    3480
cccgatcaag tcagagtcga gtcactcgtc ccagcccact gcgagggcgg cagcatcgat    3540
cacttcttcg agaacggcga cgagctcaac gagcaaatgg tgcagaggct ggaggctgcc    3600
agagagatgg gcctcgtcct gagatacgtg gcgagattcg acgccaacgg caaggcccgg    3660
gtcggggtgg aggctgtgag ggaggaccac ccgctcgcct ccctgctgcc atgcgacaac    3720
gtcttcgcta tcgagtccag atggtacaga gacaaccccc tggttatcag ggggccgggc    3780
gccgggagag acgtgaccgc tggggctatc caatcggaca tcaaccgcct cgctcaactg    3840
```

| | |
|---|---|
| ctgtgaaacc taaatgctct taactgagct aattatgtaa tgcacataca catatttaca | 3900 |
| tagatatgca tatttatata tagcatgtat attgtactac atgcattgct tcttaataca | 3960 |
| tgtagtaaag atatatgcaa aaatagtcga aagatttgtt tacatataaa atcaccaata | 4020 |
| tttattgtta ttgtattttc atgaataaag taataagatt atttgtctaa tattttgatt | 4080 |
| tactagtact agaaatgaaa aggaatatgc acaatttcag cattatagtt tggtaggcaa | 4140 |
| aatggagtga aatagagtt tcatagtata tactaaggtt cttaattgtg caaatagttg | 4200 |
| atacaagtca catgggccaa gtttgtaaat cttaaatcga aatatgcctt cttctttttt | 4260 |
| tgcatgaaaa tgctagtaat ttataagtgt gtttttcaat aagagatgct aaataccaaa | 4320 |
| attaacctag ttttcagtga gcgcttgcat tattgtgg | 4358 |

<210> SEQ ID NO 28
<211> LENGTH: 6167
<212> TYPE: DNA
<213> ORGANISM: Artificial
<220> FEATURE:
<223> OTHER INFORMATION: Construct of pBIOS10249

<400> SEQUENCE: 28

| | |
|---|---|
| agctggtgcg gcggcgcggg ggtcagccgc cgagccggcg gcgacggagg agcagggcgg | 60 |
| cgtggacgcg aacttccgat cggttggtca gagtgcgcga gttgggctta gccaattagg | 120 |
| tctcaacaat ctattgggcc gtaaaattca tgggccctgg tttgtctagg cccaatatcc | 180 |
| cgttcatttc agcccacaaa tatttcccca gaggattatt aaggcccaca cgcagcttat | 240 |
| agcagatcaa gtacgatgtt tcctgatcgt tggatcggaa acgtacggtc ttgatcaggc | 300 |
| atgccgactt cgtcaaagag aggcggcatg acctgacgcg gagttggttc cgggcaccgt | 360 |
| ctggatggtc gtaccgggac cggacacgtg tcgcgcctcc aactacatgg acacgtgtgg | 420 |
| tgctgccatt gggccgtacg cgtggcggtg accgcaccgg atgctgcctc gcaccgcctt | 480 |
| gcccacgctt tatatagaga ggttttctct ccattaatcg catagcgagt cgaatcgacc | 540 |
| gaagggagg gggagcgaag ctttgcgttc tctaatcgcc tcgtcaaggt aactaatcaa | 600 |
| tcacctcgtc ctaatcctcg aatctctcgt ggtgcccgtc taatctcgcg attttgatgc | 660 |
| tcgtggtgga aagcgtagga ggatcccgtg cgagttagtc tcaatctctc agggtttcgt | 720 |
| gcgattttag ggtgatccac ctcttaatcg agttacggtt tcgtgcgatt ttagggtaat | 780 |
| cctcttaatc tctcattgat ttagggtttc gtgagaatcg aggtagggat ctgtgttatt | 840 |
| tatatcgatc taatagatgg attggttttg agattgttct gtcagatggg gattgtttcg | 900 |
| atatattacc ctaatgatgt gtcagatggg gattgtttcg atatattacc ctaatgatgt | 960 |
| gtcagatggg gattgtttcg atatattacc ctaatgatgg ataataagag tagttcacag | 1020 |
| ttatgttttg atcctgccac atagtttgag ttttgtgatc agatttagtt ttacttattt | 1080 |
| gtgcttagtt cggatgggat tgttctgata ttgttccaat agatgaatag ctcgttaggt | 1140 |
| taaaatcttt aggttgagtt aggcgacaca tagtttattt cctctggatt tggattggaa | 1200 |
| ttgtgttctt agttttttc ccctggattt ggattggaat tgtgtggagc tgggttagag | 1260 |
| aattacatct gtatcgtgta cacctacttg aactgtagag cttgggttct aaggtcaatt | 1320 |
| taatctgtat tgtatctggc tctttgccta gttgaactgt agtgctgatg ttgtactgtg | 1380 |
| ttttttacc cgttttattt gctttactcg tgcaaatcaa atctgtcaga tgctagaact | 1440 |
| aggtggcttt attctgtgtt cttacataga tctgttgtcc tgtagttact tatgtcagtt | 1500 |

```
ttgttattat ctgaagatat ttttggttgt tgcttgttga tgtggtgtga gctgtgagca   1560
gcgctcttat gattaatgat gctgtccaat tgtagtgtag tatgatgtga ttgatatgtt   1620
catctatttt gagctgacag taccgatatc gtaggatctg gtgccaactt attctccagc   1680
tgcttttttt tacctatgtt aattccaatc ctttcttgcc tcttccagat ccagatattc   1740
gttatctcca ccatggctcg tagtctcgct gtcgccagcc cactcccacc ggcggcagcg   1800
gtcaggcgcc gtccacgggc atcggcctcc ggacgggagg tcatcagcca gtgctggaag   1860
tgcgagatca accaggatca accacttggc aatagcctca gaattgggca ctctcaaggg   1920
tcactccaac gccacggcag taggaacttg ctcgcggccg cggccgctat ctccattgag   1980
caagctgagg tttccaccta tttgccaaag ggtgacatgt ggtccgtgca caagttcggg   2040
ggaacttgca tgggcacccc gcaacgcatc cagaacgtgg ccgacattgt cctcggcgat   2100
agctctgaaa ggaagctcat tatcgtctca gctatgtcca aggtgacgga catgatgttt   2160
aacctcgttc ataaggccca atcgcgggat aactcctatg tcacagcact ggacgaggtg   2220
ttcaacaagc acatggccgc cgcaaaggaa ctcctcgatg gggaagacct cgccagattc   2280
ctcgctcagt tgcactccga catctcgaac ctccgggcca tgttgagggc tatcttcatt   2340
gccggacatg ccaccgagtc ttttttccgat ttcgtggtgg ggcatggcga gctctggtca   2400
gcgcagatgc tctcctacgc tattaagaag tcgggcgtcc cctgcagctg gatggacacg   2460
agggaggtgc tggtggtgaa gccatctgga agtaatcagg tggacccaga ttacctggag   2520
tcagagaagc ggctgcagaa gtggttttca cgccagcctg ccgagatcat catcgctact   2580
ggctttatcg cgtcgaccgc tgaaaacatt ccaacgaccc tgaagcgcga cgggtctgac   2640
ttcagtgcat ccatcatcgg ctcacttgtt cgggcctgtc aggttacaat ctggaccgac   2700
gtggatggcg tcttctcggc agacccacgg aaggtcagtg aggctgttat cttgagcacg   2760
ctctcctacc aagaagcatg ggaaatgtcc tactttggtg ccaacgtgct ccatccccgg   2820
accatcatcc cagttatgaa ggacaacatc cccattgtca tcaggaacat gttcaatctt   2880
tcggcaccgg gcaccaccat ttgcaagcaa ccagcaaacg agaatgctga tctcgacgcc   2940
tgtgttaagt ctttcgctac aatcgataag cttgcactgg tgaatgtcga gggcaccggc   3000
atggccgggg tccctggcac cgccagcgcc atcttctctg cagctaagga tgtcggagcc   3060
aacgtgatta tgatttctca agccagttcg gagcactccg tttgctttgc ggtgccagag   3120
aaggaggttg cggctgtcag caccgccttg cacgtcaggt tccgggaggc cctcgcggcc   3180
ggtagactgt ccaaggtcga ggtcattcgg ggctgctcga tcctcgccgc cgtcgggctg   3240
aggatggctt ctaccccagg cgtctcggcg atcctgttcg atgccttggc aaaggctaat   3300
atcaacgtgc gggcgatcgc gcaaggctgc tccgagtaca atatcaccgt ggtgctcaag   3360
caagaggact gtgttcgcgc cctccgggct gttcactcaa gattctttct cagtaagacg   3420
accctggccg tgggcatcat cggccccggg ctcattgggg gaaccctcct ggatcaactg   3480
aaggaccagg ccgccgtgct taaggagaac atgaatatcg atctgcgcgt gatcggcatc   3540
tctggatccc gcacgatgca cctctcggac atcggagtcg acctcaatca gtggaaggag   3600
ctgctcagaa aggaagccga gccggccgat ctggactcgt tgtgcgtca tctgtccgag   3660
aaccacgtgt tcccaaataa ggtgctcgtg gactgcactg ccgatacccta cgtggcatgc   3720
cactactatg actggctgaa gaagggcatc cacgttatca cccccaacaa gaaggctaac   3780
tccgcccac ttgatcgcta cctcaagctc cgtactcttc aaagggcttc ttacacacac   3840
tacttctacg aggcgaccgt gggagccggg ctccctatca tctccaccct ccgcggcctg   3900
```

```
ctggagactg gggacaagat cctgcggatt gagggtatct tttccggtac cctctcctac    3960 attttaaca acttcgaggg cacccggaca ttctctaacg tggtggccga ggcgaaggag    4020
gctggctaca ccgagccaga cccacgcgac gacttgtcgg gtacagatgt ggcgcgtaag    4080
gttatcatct tggcgcgcga gtctggtctt cgcctcgagc tctcggatat tcctgttaag    4140
agccttgtcc cagaggccct gaggagttgc agttccgccg acgaattcat gcagaagttg    4200
ccgtcttttg accaagactg ggaccgccag agggatgaag ccgaggccgc cggagaggtg    4260
ctccgctacg tcggcgtggt ggacgtcgcc aacaggaagg gccgtgttga acttcaacgg    4320
tacaagcgcg atcatccatt tgcgcaactt tcgggtagcg ataatatcat cgcctttacc    4380
acctcgagat acaaggagca accccttgatc gttagaggac caggagctgg tgccgaagtt    4440
accgcggggg gagtcttctg cgacattctg cgcctcgcgt cgtatctggg cgcaccgagt    4500
taaaactcct gggccatgaa gctgtccttc caggttcaca agtctggtgc cttcttctgt    4560
ccctccgatg gagattatct gcatgtcgtg gtcgtgtcct gatcgaatcc tcgttgaatc    4620
cctatgtttt tcttcaagaa atgtgagtcc tatgtcagtc tggttgcgtt tgtgaacatt    4680
tctgctgctg aggagcactt tggctggaac tgtgcaatga aataaatgga accctggttt    4740
ctggttatgt gtgtgttagc taatgttttt gaagtggaag ctctaatctt ctatcgcgtt    4800
gctactacaa ttctgcttgt gttttgatgt tcttggtttc tgttagttgg ttcagaggaa    4860
gttttgcttc cacagactaa gatgcagttg aactttggtt gccctggttt ctagatttca    4920
tttgtgctgg ttgagtgata gtaagaaaca accggtgttc acatataatc aggttttgtg    4980
ctgctcgagt gatcgtcaaa aaccaccggt gttcacatct aaaaaggttt cgatccccag    5040
gtttagatct cccgtttaat tccaaaaaaa aagttctgtg tacttgcatt tagttgggtg    5100
gttgatgctg gaaagagtaa cttttcaagag taataatctt tggtgactac tctgtttcaa    5160
ctgatcaatc cctaggaaag gtacaccttt acttagggaa gaaattctta gaaccttgca    5220
ctttgtttca actgataata gtatacttta ttagataaaa atatattcaga tatattagac    5280 accggatgtc atccactcat ccttacaaac ctctgtcatg gtcctgcaga aatgtttgcc    5340
agctccagtg gcttcctgat aaatctgtgg agtgcctgtt aatcggctgc caattttttgc    5400 tgagcactgt atatatgtta gtaagtacta ttgggccacc aattcgattt tgacacagca    5460
ctattggtcc accaattcga ttctgacaca gcactgcata atttgaaacg tgttgctcca    5520
ttttgcaagg ctacaaattt agatcatgtt tagcattctg tgggatacaa tatatggata    5580
tcgaacaaac ttggtatgtc agagaaaaaa tagtttattt tcaaaactaa catttttaaa    5640
gccttctatg aactttaaac cttcagcatt tgggatcaag atgagtgctc gaacaagagt    5700 gcacttttc tccaaaataa tctactacag agttcttttt tatatataaa aaacttata    5760 cttaacagat aaatcagact ttttctgctc catatcacct tgacaaatca agaagcagc    5820 accagcgaag ggtattatta ttgaggtaaa tataagatct cgtttactga aaagaccgc    5880 gtgtttacct aaactaccat tttgctttga tagcagcata catgtgatag aattgcggat    5940
cctaccgtgc tgactgtgaa ggtggtaggg gtgagagatt ggtgggcgag gtctgaacga    6000
gcgagaacag tactgcattt actgttcaca aggaggcggc ttaggttttg ggtctcccag    6060
ctctctaagg gaagctgaga attatgattc tcttgcttaa ttatttctta accaaagtta    6120
taaatatata gcctatgaga tcctaattta tggaaataac taaacta                  6167
```

<210> SEQ ID NO 29
<211> LENGTH: 1744
<212> TYPE: DNA
<213> ORGANISM: Artificial
<220> FEATURE:
<223> OTHER INFORMATION: rice ubi3 promoter

<400> SEQUENCE: 29

```
agctggtgcg gcggcgcggg ggtcagccgc cgagccggcg gcgacggagg agcagggcgg     60
cgtggacgcg aacttccgat cggttggtca gagtgcgcga gttgggctta gccaattagg    120
tctcaacaat ctattgggcc gtaaaattca tgggccctgg tttgtctagg cccaatatcc    180
cgttcatttc agcccacaaa tatttcccca gaggattatt aaggcccaca cgcagcttat    240
agcagatcaa gtacgatgtt tcctgatcgt tggatcggaa acgtacggtc ttgatcaggc    300
atgccgactt cgtcaaagag aggcggcatg acctgacgcg gagttggttc cgggcaccgt    360
ctggatggtc gtaccgggac cggacacgtg tcgcgcctcc aactacatgg acacgtgtgg    420
tgctgccatt gggccgtacg cgtggcggtg accgcaccgg atgctgcctc gcaccgcctt    480
gcccacgctt tatatagaga ggttttctct ccattaatcg catagcgagt cgaatcgacc    540
gaaggggagg gggagcgaag ctttgcgttc tctaatcgcc tcgtcaaggt aactaatcaa    600
tcacctcgtc ctaatcctcg aatctctcgt ggtgcccgtc taatctcgcg attttgatgc    660
tcgtggtgga aagcgtagga ggatcccgtg cgagttagtc tcaatctctc agggtttcgt    720
gcgattttag ggtgatccac ctcttaatcg agttacggtt tcgtgcgatt ttagggtaat    780
cctcttaatc tctcattgat ttagggtttc gtgagaatcg aggtagggat ctgtgttatt    840
tatatcgatc taatagatgg attggttttg agattgttct gtcagatggg gattgtttcg    900
atatattacc ctaatgatgt gtcagatggg gattgtttcg atatattacc ctaatgatgt    960
gtcagatggg gattgtttcg atatattacc ctaatgatgg ataataagag tagttcacag   1020
ttatgttttg atcctgccac atagtttgag ttttgtgatc agatttagtt ttacttatttt   1080
gtgcttagtt cggatgggat tgttctgata ttgttccaat agatgaatag ctcgttaggt   1140
taaaatcttt aggttgagtt aggcgacaca tagtttattt cctctggatt tggattggaa   1200
ttgtgttctt agttttttc ccctggattt ggattggaat tgtgtggagc tgggttagag   1260
aattacatct gtatcgtgta cacctacttg aactgtagag cttgggttct aaggtcaatt   1320
taatctgtat tgtatctggc tctttgccta gttgaactgt agtgctgatg ttgtactgtg   1380
ttttttttacc cgtttttattt gctttactcg tgcaaatcaa atctgtcaga tgctagaact   1440
aggtggcttt attctgtgtt cttacataga tctgttgtcc tgtagttact tatgtcagtt   1500
ttgttattat ctgaagatat ttttggttgt tgcttgttga tgtggtgtga gctgtgagca   1560
gcgctcttat gattaatgat gctgtccaat tgtagtgtag tatgatgtga ttgatatgtt   1620
catctatttt gagctgacag taccgatatc gtaggatctg gtgccaactt attctccagc   1680
tgctttttt taccctatgtt aattccaatc ctttcttgcc tcttccagat ccagatattc   1740
gtta                                                                 1744
```

<210> SEQ ID NO 30
<211> LENGTH: 1661
<212> TYPE: DNA
<213> ORGANISM: Artificial
<220> FEATURE:
<223> OTHER INFORMATION: sugarcane terminator SoUbi4

-continued

```
<400> SEQUENCE: 30
tcctgggcca tgaagctgtc cttccaggtt cacaagtctg gtgccttctt ctgtccctcc    60
gatggagatt atctgcatgt cgtggtcgtg tcctgatcga atcctcgttg aatccctatg   120
tttttcttca agaaatgtga gtcctatgtc agtctggttg cgtttgtgaa catttctgct   180
gctgaggagc actttggctg gaactgtgca atgaaataaa tggaaccctg gtttctggtt   240
atgtgtgtgt tagctaatgt ttttgaagtg gaagctctaa tcttctatcg cgttgctact   300
acaattctgc ttgtgttttg atgttcttgg tttctgttag ttggttcaga ggaagttttg   360
cttccacaga ctaagatgca gttgaacttt ggttgccctg gtttctagat ttcatttgtg   420
ctggttgagt gatagtaaga aacaaccggt gttcacatat aatcaggttt tgtgctgctc   480
gagtgatcgt caaaaaccac cggtgttcac atctaaaaag gtttcgatcc ccaggtttag   540
atctcccgtt taattccaaa aaaaaagttc tgtgtacttg catttagttg ggtggttgat   600
gctggaaaga gtaactttca agagtaataa tctttggtga ctactctgtt tcaactgatc   660
aatccctagg aaaggtacac ctttacttag ggaagaaatt cttagaacct tgcactttgt   720
ttcaactgat aatagtatac tttattagat aaaaaatatt cagatatatt agacaccgga   780
tgtcatccac tcatccttac aaacctctgt catggtcctg cagaaatgtt tgccagctcc   840
agtggcttcc tgataaatct gtggagtgcc tgttaatcgg ctgccaattt ttgctgagca   900
ctgtatatat gttagtaagt actattgggc caccaattcg attttgacac agcactattg   960
gtccaccaat tcgattctga cacagcactg cataatttga aacgtgttgc tccattttgc  1020
aaggctacaa atttagatca tgtttagcat tctgtgggat acaatatatg gatatcgaac  1080
aaacttggta tgtcagagaa aaaatagttt attttcaaaa ctaacatttt taaagccttc  1140
tatgaacttt aaaccttcag catttgggat caagatgagt gctcgaacaa gagtgcactt  1200
tttctccaaa ataatctact acagagttct ttttatata taaaaaaact tatacttaac  1260
agataaatca gactttttct gctccatatc accttgacaa atcaaagaag cagcaccagc  1320
gaagggtatt attattgagg taaatataag atctcgttta ctgaaaaaga ccgcgtgttt  1380
acctaaacta ccatttttgct ttgatagcag catacatgtg atagaattgc ggatcctacc  1440
gtgctgactg tgaaggtggt aggggtgaga gattggtggg cgaggtctga acgagcgaga  1500
acagtactgc atttactgtt cacaaggagg cggcttaggt tttgggtctc ccagctctct  1560
aagggaagct gagaattatg attctcttgc ttaattattt cttaaccaaa gttataaata  1620
tatagcctat gagatcctaa tttatggaaa taactaaact a                      1661
```